United States Patent [19]
Lardy et al.

[11] Patent Number: 5,387,709
[45] Date of Patent: Feb. 7, 1995

[54] SUBSTITUTED SULFONAMIDES, PROCESS OF PREPARATION AND MEDICINES CONTAINING SAME

[75] Inventors: Claude Lardy, Lyons; Daniel Guerrier, Saint Genis Laval; Gilles Chavernac, La Mulatiere; François Collonges, Beynost Miribel, all of France

[73] Assignee: Lipha Lyonnaise Industrielle Pharmaceutique, Lyon Cedex, France

[21] Appl. No.: 134,731

[22] Filed: Oct. 12, 1993

Related U.S. Application Data

[63] Continuation of Ser. No. 736,240, Jul. 26, 1991, abandoned.

[30] Foreign Application Priority Data

Jul. 31, 1990 [FR] France ................. 9009737

[51] Int. Cl.$^6$ .................. C07C 255/00; C07D 233/54
[52] U.S. Cl. ...................... 558/388; 564/85; 560/10; 560/12; 562/6; 562/5; 562/11; 548/311.1; 548/315.4; 548/315.7; 548/323.5; 548/112; 546/152; 544/106
[58] Field of Search ............. 558/388; 564/85; 560/10, 12; 562/65, 11; 548/335; 546/152; 544/106

[56] References Cited

U.S. PATENT DOCUMENTS

| | | | |
|---|---|---|---|
| 4,350,685 | 9/1982 | Ali et al. | 564/79 X |
| 4,948,810 | 8/1990 | Iwakuma et al. | 514/539 |
| 4,981,873 | 1/1991 | Witte et al. | 514/562 |
| 4,999,345 | 3/1991 | Schmied et al. | 514/117 |
| 5,006,542 | 4/1991 | Hall et al. | 514/381 |

FOREIGN PATENT DOCUMENTS

| | | |
|---|---|---|
| 0312906 | 4/1989 | European Pat. Off. . |
| 0358398 | 3/1990 | European Pat. Off. . |
| 0361113 | 4/1990 | European Pat. Off. . |

*Primary Examiner*—José G. Dees
*Assistant Examiner*—Joseph M. Conrad
*Attorney, Agent, or Firm*—Oblon, Spivak, McClelland, Maier & Neustadt

[57] ABSTRACT

The present invention concerns new substituted sulfonamides, and the physiologically acceptable salts possibly in the form of complexes, esters and amides thereof, represented by the formula:

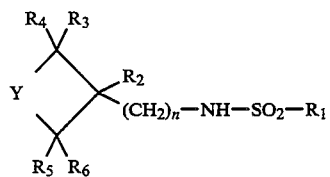

12 Claims, No Drawings

SUBSTITUTED SULFONAMIDES, PROCESS OF PREPARATION AND MEDICINES CONTAINING SAME

This application is a continuation of application Ser. No. 07/736,240, filed on Jul. 26, 1991, now abandoned.

BACKGROUND OF INVENTION (a) Field of the Invention

The present invention relates to new substituted sulfonamides, their preparation and use as medicines and such as for the treatment of diseases where the involvement of thromboxane $A_2$ is recognized.

(b) Description of Prior Art

Arachidonic acid which is exogeneous or released by phospholipids by the action of phospholipase $A_2$ is converted into endoperoxides (prostaglandine $G_2$ ($PGG_2$) and into prostaglandine $H_2$ ($PGH_2$)) by means of cyclooxygenase. The thromboxane synthetase thereafter catalyzes the conversion of $PGH_2$ into thromboxane $A_2$ ($TXA_2$). The latter is capable, at very low concentrations, to induce serious biological disorders, such as platelet aggregation, vasoconstriction, bronchoconstriction, participating in the loss of integrity of the vascular membrane, thus making it responsible for certain diseases of the circulatory system and the respiratory system. These pathophysiological actions pass through the intermediary of receptors which can collect thromboxane $A_2$ as well as the endoperoxides $PGG_2/PGH_2$.

A method of inhibiting the effects of thromboxane $A_2$ is to use selective antagonists of the receptors $TXA_2/PGH_2$ and many products acting according to this mechanism are described in the art: see for example U.S. Pat. Nos. 4,443,477 and 4,861,913.

U.S. Pat. No. 4,443,477 describes sulfonamidobenzenecarboxylic acids which inhibit platelet aggregation, lower seric lipids and which have a general structure:

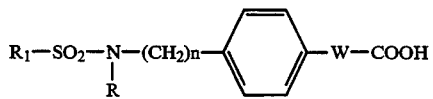

where R is an hydrogen atom or a lower alkyl radical, $R_1$ is an alkyl or aryl or aralkyl or aralkenyl radical, where the aryl group may possibly be in each case substituted by one or more of the following groups: hydroxyl, halogen, trifluoromethyl, lower alkyl or alkoxy or acyl, carboxy or alkoxycarbonyl; n is 1, 2 or 3 and W is a bond or an aliphatic hydrocarbon chain which is linear or not linear, containing a double or saturated bond, as well as the physiologically acceptable salts, esters and physiologically acceptable amides.

U.S. Pat. No. 4,861,913 describes bicyclic derivatives of sulfonamides which are inhibitors of platelet aggregation induced by thromboxane $A_2$, inhibitors of vasoconstriction and of bronchoconstriction and which have the following general structure:

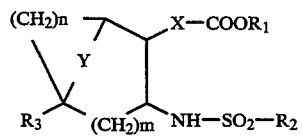

where $R_1$ is a hydrogen atom or a lower alkyl group; $R_2$ is an alkyl radical or an aryl residue which is possibly substituted or an aralkyl group or a heterocycle; $R_3$ represents an hydrogen atom or a methyl group; X is an alkylene chain or an alkenylene chain which is possibly substituted by a fluorine atom and may contain oxygen or sulfur and/or a phenylene group in the chain; Y represents an alkylene or alkenylene chain or an atom of oxygen or sulfur; m is 0 or 1; n is 0, 1 or 2.

SUMMARY OF INVENTION

The products of the present invention, their salts, complexes, esters and amides which are physiologically acceptable have the following general formula (I):

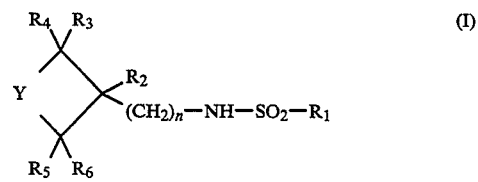

in which $R_1$ is an aryl radical or a heterocycle, possibly substituted by one or more of the following groups: halogen, trifluoromethyl, trifluoromethoxy, lower alkyl which is possibly substituted by a primary, secondary or tertiary alcohol function, cycloalkyl, lower alkoxy, alkoxycarbonyl, carboxylic, lower alkylthio, lower alkylsulfinyl, lower alkylsulfonyl, lower acyl, lower thioacyl, hydroxyl, amine which is possibly (poly)substituted with a lower alkyl radical, acetamide, nitro, nitrile, azide, aryle;

$R_2$ and $R_3$ are different; one of the two represents W, the other is hydrogen, halogen, trifluoromethyl, lower alkyl, cycloalkyl, lower alkoxy, lower alkylthio, lower alkylsulfinyl, lower alkylsulfonyl, lower acyl, lower thioacyl, hydroxyl, amine possibly (poly)substituted by a lower alkyl radical, acetamide, nitro, nitrile, azide, aryl; W represents a —Z—Ar—$(CH_2)_q$—A chain, in which A is $CO_2H$ or a group which is hydrolyzable into $CO_2H$, $SO_3H$, $PO_3H$, a heterocycle, a lower acyl radical, an oxoalkylcarboxylic radical or a primary alcohol; q represents 0, 1, 2, 3 or 4; Ar is an aryl radical or an aromatic heterocycle, possibly substituted by a radical $R_7$. The chain —$(CH_2)_q$—A is in ortho, meta or para position when Ar represents a phenyl radical. Z is an oxygen atom, a methylene group or a bond;

when $R_3$ is W, $R_2$ is always different than W and the products formed could have the cis or trans configuration or be in racemic form;

$R_4$, $R_5$, $R_6$ and $R_7$ may simultaneously, or independently from one another, be hydrogen, halogen, trifluoromethyl, trifluoromethoxy, lower alkyl, cycloalkyl, lower alkoxy, lower alkylthio, lower alkylsulfinyl, lower alkylsulfonyl, lower acyl, lower thioacyl, hydroxyl, thiol, amine possibly substituted or polysubstituted by a lower alkyl radical, acetyl, acetamide, nitro, nitrile, azide or aryl;

Y is a group —$(CH_2)_s$—B—$(CH_2)_t$— in which s represents 0, 1 or 2, t is 0, 1 or 2; ,B is either a bond, or a heteroatom, oxygen, oxidized or non oxidized sulfur, or nitrogen possibly substituted by a lower alkyl radical, a lower acyl radical or an aryl radical, or a carbonyl or thiocarbonyl function, or a heterocycle or a cycle

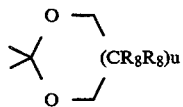

where $R_8$ is hydrogen, halogen, or lower alkyl, u being equal to 0 or 1, or an alkene residue —CH=CH—,

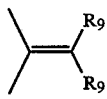

in which $R_9$ is hydrogen, halogen or lower alkyl, or a group —$(CR_{10}R_{11})_v$— or —O—$(CR_{10}R_{11})_v$—O— in which $R_{10}$ and $R_{11}$ are identical or different and represent hydrogen, halogen, trifluoromethyl, lower alkyl, cycloalkyl, lower alkoxy, lower alkylthio, lower alkylsulfinyl, lower alkylsulfonyl, lower acyl, lower thioacyl, hydroxyl, amine possibly (poly)substituted by a lower alkyl radical, acetamide, nitro, nitrile, azide or aryl, v being equal to 0, 1 or 2. When s and t represent 0 and B is a bond, the group —$(CR_3R_4)$— is directly bonded to —$(CR_5R_6)$—;

n is 0 or 1.

The physiologically acceptable salts of the compounds of formula (I) comprise the salts formed with metals (such as sodium, potassium, calcium, magnesium), or with bases such as ammonia or substituted amines (such as diethylamine, triethylamine, piperidine, piperazine, morpholine), or with basic amino acids (such as lysine, arginine) or with osamines (such as meglumine).

The physiologically acceptable complexes of the compounds of formula (I) are prepared from compounds of formula (I) or their salts land a non substituted or substituted α-, β- or γ-cyclodextrine, which is hydrated or non hydrated, and more particularly β-cyclodextrine.

The term "aryl" represents a mono or bicyclic aromatic group comprising 6 to 10 carbon atoms, such as phenyl or naphthyl.

The term "heterocycle" designates a cycle with aromatic or non aromatic character, comprising 3 to 10 atoms including 1 to 4 heteroatoms which are the same or different and are taken from oxygen, sulfur and nitrogen, such as for example, the radicals aziridinyl, oxiranyl, oxazolyl, furyl, tetrahydrofuranyl, thienyl, imidazolyl, pyridyl, pyrazinyl, benzopyranyl, benzofuranyl, piperonyl, pyrimidinyl, pyridazinyl, piperidinyl, quinolyl, tetrahydroquinolyl, tetrazolyl, 4,5-dihydro-3(2H)-pyridazinonyl, phthalazinyl, purinyl, indolyl, chromenyl, chromanyl, isochromanyl, pyrrolyl.

The term "cycloalkyl" represents saturated hydrocarbon groups containing 3 to 12 carbon atoms, preferably 3 to 8, selected from cyclopropyl, cyclobutyl, cyclopentyl, cyclohexyl, cycloheptyl, cyclooctyl, cyclononyl, cyclodecyl, cycloundecyl and cyctododecyl.

The term "halogen" represents an atom of fluor, chlorine, bromine or iodine.

The term "lower" applied to an alkyl radical, means that the radical may be linear or branched and may comprise from 1 to 7 carbon atoms, such as methyl, ethyl, propyl, isopropyl, butyl, tert-butyl, isobutyl, pentyl, hexyl, heptyl.

The term "lower alkoxy" represents a lower alkyl group bonded to an oxygen atom, such as the radicals methoxy, ethoxy, butoxy, hexyloxy.

The terms "lower alkylthio", "lower alkylsutfinyl" and "lower alkylsulfonyl" represent a lower alkyl group bonded to an atom of sulfur which is respectively non oxidized, mono-oxidized or di-oxidized, such as methylthio, methylsulfinyl or methylsulfonyl.

The terms "lower acyl" and "lower thioacyl" represent a lower alkyl group respectively bonded to a carbonyl or thiocarbonyl function, such as the radicals acetyl, propionyl, thioacetyl.

The term "oxoalkylcarboxylic" represents a lower acyl group carrying a carboxylic acid function, such as the radical 4-(4-oxobutanoic).

The term "hydrolyzable group" used in the definition of A means that the organic acid may be in the form of salt with a metal (such as Na, K, Li, Ca or Mg) or in the form of ester with a lower alkoxy radical, with lower alkoxy amino radicals such as N,N-diethylaminoethoxy, N,N-dimethylaminoethoxy, or in the form of amide with amines such as ammonia, morpholine, piperidine, piperazine or with amino acids such as glycine, β-alanine.

The term "trans" used for the compounds carrying asymmetrical carbon atoms in the cycloalkyl group is applied when the 2 substituents are on either part of the plane formed by the cycle.

The term "cis" for the compounds carrying asymmetrical carbon atoms in the cycloalkyl group is applied when the 2 substituents are on the same side of the plane formed by the cycle.

DESCRIPTION OF PREFERRED EMBODIMENTS

A preferred family of compounds according to the invention, in which $R_3$ is the group W and $R_2$ is different than W, is represented by the general formula (Ia).

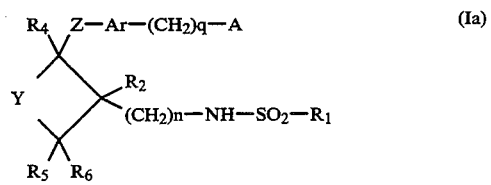

Another preferred family, of compounds according to the invention, in which $R_2$ is the group W and $R_3$ is different from W, is represented by general formula (Ib).

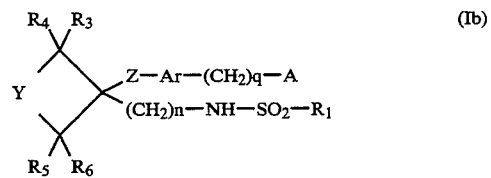

The substituents $R_{1-6}$, the parameters A, Y, Z, Ar, n and q have the values mentioned in formula (I).

In these two formulae, (Ia) and (Ib), the preferred products are those for which Ar is a phenyl radical, and A is a carboxylic acid function or a tetrazolyl radical.

In these structures of the type (Ia), there are many preferred families, in particular when n is equal to 0 and Z is CH$_2$, when n is 0 and Z is a bond and when n is 0 and Z is an oxygen atom.

In the structures of the type (Ib), there are may preferred families, in particular when n is equal to 0 and Z is a bond, when n is 0 and Z is CH$_2$, when n is equal to 1 and Z is a bond, when n is 1 and Z is CH$_2$ and when n is 1 and Z is an oxygen atom.

Among the preferred compounds of the invention there should be mentioned:

trans-4-[[2-[[(4-chlorophenyl)sulfonyl]amino]cyclopentyl]methyl]benzeneacetic acid,
sodium trans-4-[[2-[[(4-chlorophenyl)sulfonyl]amino]cyclopentyl]methyl]benzeneacetate,
cis-4-[[2-[[(4-chlorophenyl)sulfonyl]amino]cyclopentyl]methyl]benzeneacetic acid,
trans-4-[[2-[[(4-fluorophenyl)sulfonyl]amino]cyclopentyl]methyl]-benzeneacetic acid,
trans-4-[[2-[[(phenyl)sulfonyl]amino]cyclopentyl]methyl]benzeneacetic acid,
trans-4-[[2-[[(4-methylphenyl)sulfonyl]amino]cyclopentyl]methyl]benzeneacetic acid,
ethyl trans-4-[[2-[[(4-chlorophenyl)sulfonyl]amino]cyclopentyl]methyl]benzeneacetate,
4-[2-[[(4-chlorophenyl)sulfonyl]amino]cyclopentYloxY]benzeneacetic acid,
trans-4-[2-[[(4-chlorophenyl)sulfonyl]amino]cyclohexyl]benzeneacetic acid,
trans-4-[[2-[[(4-chlorophenyl)sulfonyl]amino]cyclohexyl]methyl]benzeneacetic acid,
4-[1-[[[(4-chlorophenyl)sulfonyl]amino]methyl]cyclopropyl]benzeneacetic acid,
4-[1[[[(4-chlorophenyl)sulfonyl]amino]methyl]cyclobutyl]benzeneacetic acid,
4-[1-[[[(4-chlorophenyl)sulfonyl]amino]methyl]cyclopentyl]benzeneacetic acid,
4-[[1-[[[(phenyl)sulfonyl]amino]methyl]cyclopentyl]methyl]benzeneacetic acid,
4-[[1-[[[(4-fluorophenyl)sulfonyl]amino]methyl]cyclopentyl]methyl]benzeneacetic acid,
N-[[1-[(4-acetylphenyl)methyl]cyclopentyl]methyl]-4-chlorobenzenesulfonamide,
methyl 4-[[1-[[[(4-chlorophenyl)sulfonyl]amino]methyl]cyclopentyl]methyl]benzeneacetate,
4-[[1-[[[(4-chlorophenyl)sulfonyl]amino]methyl]cyclopentyl]methyl]benzeneacetic acid,
sodium 4-[[1-[[[(4-chlorophenyl)sulfonyl]amino]methyl]-cyclopentyl]methyl]benzeneacetate,
sodium trans -4-[[2-[[(4-chlorophenyl)sulfonyl]amino]cyclopentyl]methyl]benzeneacetate and β-cyclodextrine (1:1) complex,
sodium 4-[[1-[[[(4-chlorophenyl)sulfonyl]amino]methyl]cyclopentyl]methyl]benzeneacetate and β-cyclodextrine (1:1) complex,
4-[[1-[[[(4-methylphenyl)sulfonyl]amino]methyl]cyclopentyl]methyl)benzeneacetic acid,
4-[[1-[[[(4-chlorophenyl)sulfonyl]amino]methyl]cyclopentyl]methyl]benzoic acid,
4-[[1-[[[(3,4-dichlorophenyl)sulfonyl]amino]methyl]cyclopentyl]methyl]benzeneacetic acid,
4-[[1-[[[(4-chlorophenyl)sulfonyl]amino]methyl]cyclobutyl]methyl]benzeneacetic acid,
4-chloro-N-[[1-[[4-(2-hydroxyethyl)phenyl]methyl]cyclopentyl]methyl]benzenesulfonamide,
4-[4-[1-[[[(4-chlorophenyl)sulfonyl]amino]methyl]cyclopentyl]methyl]phenyl]-4-oxobutanoic acid,
4-[[1-[[[(2-chlorophenyl)sulfonyl]amino]methyl]cyclopentyl]methyl]benzeneacetic acid,
3-chloro-N-[[1-[[4-(2-hydroxyethyl)phenyl]methyl]cyclopentyl]methyl]benzenesulfonamide,
4-acetyl-N-[[1-[[4-(2-hydroxyethyl)phenyl]methyl]cyclopentyl]methyl]benzenesulfonamide,
N-[[1-[[4-(2-hydroxyethyl)phenyl]methyl]cyclopentyl]methyl]-4-(methylsulfonyl)benzenesulfonamide,
N-[[1- [[4-(2-hydroxyethyl)phenyl]methyl]cyclopentyl]methyl]-4-(trifluoromethoxy)benzenesulfonamide,
4-[[1- [[[(4-bromophenyl)sulfonyl]amino]methyl]cyclopentyl]methyl]benzeneacetic acid,
4-[[1- [[[(4-iodophenyl)sulfonyl]amino]methyl]cyclopentyl]methyl]benzeneacetic acid,
4-[[1-[[[(4-trifluoromethylphenyl)sulfonyl]amino]methyl]cyclopentyl]methyl]benzeneacetic acid,
4-[[1- [[[(4-cyanophenyl)sulfonyl]amino]methyl]cyclopentyl]methyl]benzeneacetic acid,
4-[[1- [[[(2,4-dichlorophenyl)sulfonyl]amino]methyl]cyclopentyl]methyl]benzeneacetic acid,
4-[[1-[[[(4-trifluoromethoxyphenyl)sulfonyl]amino]methyl]cyclopentyl]methyl]benzeneacetic acid,
4-[[1-[[[(4-methoxyphenyl)sulfonyl]amino]methyl]cyclopentyl]methyl]benzeneacetic acid,
4-[[1-[[[(thien-2-yl)sulfonyl]amino]methyl]cyclopentyl]methyl]benzeneacetic acid,
4-[[1-[[[(5-chlorothien-2-yl)sulfonyl]amino]methyl]cyclopentyl]methyl]benzeneacetic acid,
4-[[1- [[[(4-hydroxyphenyl)sulfonyl]amino]methyl]cyclopentyl]methyl]benzeneacetic acid,
4-[[1-[[[(4-chlorophenyl)sulfonyl]amino]methyl]cyclopropyl]methyl]benzeneacetic acid,
4-[[1-[[[(4-chlorophenyl)sulfonyl]amino]methyl]cycloheptyl]methyl]benzeneacetic acid,
3-[[2-[4-[[1-[[[(4-chlorophenyl)sulfonyl]amino]methyl]cyclopentyl]methyl]phenyl]-1-oxoethyl]amino]propionic acid,
ethyl 4-[[1-[[[(4-chlorophenyl)sulfonyl]amino]methyl]cyclopentyl]methyl]benzeneacetate,
2-(diethylamino)ethyl 4-[[1-[[[(4-chlorophenyl)sulfonyl]amino]methyl]cyclopentyl]methyl]benzeneacetate,
4-[[1-[[[(4-chlorophenyl)sulfonyl]amino]methyl]cyclopentyl]methyl]benzenemethanesulfonic acid,
4-chloro-N-[1-[[[4-[(1H-tetrazol-5-yl)methyl]phenyl)methyl]cyclopentyl]methyl]-benzenesulfonamide,
4-[[1-[[[(4-chlorophenyl)sulfonyl]amino]methyl]cyclopentyl]methyl]phenylmethanephosphonic acid,
4-[[1-[[[(4-acetamidophenyl)sulfonyl]amino]methyl]cyclopentyl]methyl]benzeneacetic acid,
4-[[1-[[[(4-aminophenyl)sulfonyl]amino]methyl]cyclopentyl]methyl]benzeneacetic acid,
4-[[1-[[[(4-chlorophenyl)sulfonyl]amino]methyl]cyclohexyl]methyl]benzeneacetic acid,
4-[[4- [[[(4-chlorophenyl)sulfonyl]amino]methyl]-2,3,5,6-tetrahydropyran-4-yl]methyl]benzeneacetic acid,
4-[[1- [[[(4-chlorophenyl)sulfonyl]amino]methyl]-3,3-dimethylcyclobutyl]methyl]benzeneacetic acid,
2-[[1- [[[(4-chlorophenyl)sulfonyl]amino]methyl]cyclopentyl]methyl]benzeneacetic acid,
3-[[1- [[[(4-chlorophenyl)sulfonyl]amino]methyl]cyclopentyl]methyl]benzeneacetic acid,
4-[[1- [[[(4-nitrophenyl)sulfonyl]amino]methyl]cyclopentyl]methyl]benzeneacetic acid,
4-[[1-[[[(4-bromophenyl)sulfonyl]amino]methyl]cyclobutyl]methyl]benzeneacetic acid,
4-[[1-[[[(2-fluorophenyl)sulfonyl]amino]methyl]cyclopentyl]methyl]benzeneacetic acid, 4-[[1-[[[(naphthalen-2-yl)sulfonyl]amino]methyl]cyclopentyl]methyl]benzeneacetic acid, 4-[[1-[[[(4-chloro-2-fluorophenyl)sulfonyl]amino]methyl]cyclopentyl]methyl]benzeneacetic acid, 4-[[1-[[[(quinol-8-yl)sulfonyl]amino]methyl]cyclopentyl)methyl]benzeneacetic acid.

The invention also aims at a process of preparation of the compounds of formula (I). It relates to a sulfonation process described hereinbelow:

the product of formula (I) are prepared from the amine (II) which is reacted with an arylsulfonyl or heteroarylsulfonyl chloride in the molar proportions (II)/R$_1$—SO$_2$Cl 1:0.5 to 1:5, preferably 1:0.95 to 1:1.05 to give (I).

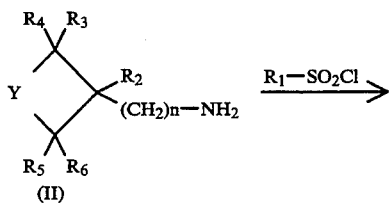

In the structures (II) and (I), W represented by R$_2$ or R$_3$ have the meanings previously defined and may also represent —Z—Ar, or more specifically Ar, —CH$_2$—Ar or —O—Ar. The substituents R$_{1-6}$ and the parameters Y, Z, Ar and n have the meanings defined previously. When W contains A representing CO$_2$H, the carboxyl function is possibly protected in a form of ester with a lower alkoxy radical. When W contains A representing a lower acyl radical, q being equal to 0, the carbonyl function is blocked by a known protecting group, such as dimethylacetal, 1,3-dioxane, 5,5-dimethyl-1,3-dioxane.

The sulfonation reaction is carried out in the presence of a base such as triethylamine, pyridine, potassium carbonate, sodium hydroxide, potassium hydroxide or butyllithium, in molar proportions (II)/base 1:1 to 1:5, more particularly 1:1.2 to 1:2.2 in a solvent which is inert towards the reaction, such as water, benzene, tetrahydrofuran, ethyl ether or dichloromethane or a mixture of ether/dichloromethane in the proportions v/v 1:1 to 1:30 and more particularly from 1:2 to 1:15. The reaction temperature is between −78° C. and the reflux temperature of the solvent or of the mixture of solvents and preferably between −20° C. and the reflux temperature of the solvent or the mixture of solvents, for a time between 2 and 72 hours, preferably between 2 and 16 hours.

The amines used in the general process for the synthesis of the compounds (I) may be formed by many processes depending of the substituents already present in the molecule:

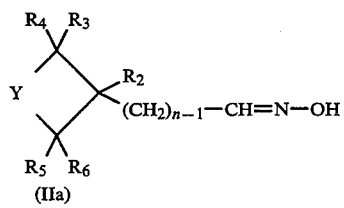
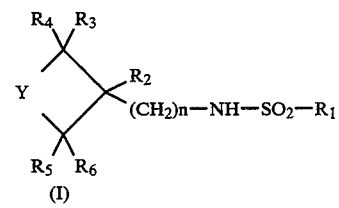

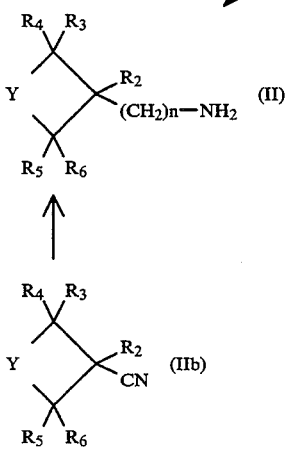

either by reduction of the oxime (IIa), for example during a catalytic hydrogenation under pressure in an ethanol-ammonium hydroxide mixture; or by breaking of the sulfonamide bond of the compound of formula (I), for example by means of a base such as sodium containing naphthalene in a solvent of the type 1,2-dimethoxyethane; or by reduction of the nitrile (IIb), for example by catalytic hydrogenation under pressure in a methanol-ammonium hydroxide mixture or by reduction with LiAlH$_4$ in ether, tetrahydrofuran or toluene at a temperature between −30° C. and the reflux temperature of the solvent and more particularly between 0° C. and the reflux temperature of the solvent. In

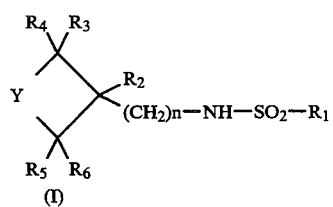

the formulae, (I), (II), (IIa) and (IIb), W represented by R$_2$ or R$_3$ have the meanings given previously and may additionally mean —Z—Ar. The substituents R$_{1-6}$ and the parameters Y, Z, Ar and n have the meanings given previously,.

The nitriles of formula (IIb) are obtained after alkylation of a nitrile (IIc) with a halogenated compound R$_2$-X.

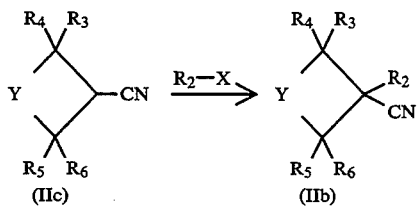

in which X is a halogen atom, R$_2$-X being more specifically X—CH$_2$—Ar or X—CH$_2$—Ar—(CH$_2$)$_q$—A; the substituents R$_{2-6}$ and the parameters Y, Ar, A and q have the meanings indicated above. The reaction is carried out in the presence of a base, such as butyllithium, lithium diisopropylamide or sodium amide in a solvent such as diethyl ether or tetrahydrofuran in the presence of hexamethylphosphoramide or N,N-dimethylimidazolidinone, at a temperature between −78° C. and the reflux temperature of the solvent or the mixture of solvents, for a period of time between 4 hours and 24 hours.

For the compounds of formula (IIb) where W, represented by R$_2$, contains a primary alcohol, the latter is protected by a group enabling to carry out the alkylation reaction, such as for example a labile protecting group such as silyl radicals, in particular —SiMe$_3$. The protecting group is thereafter removed by an acid treatment in an aqueous medium or by the use of a fluoride (for example tetrabutylammonium fluoride) in tetrahydrofuran, at a temperature between −20° and 150°, preferably at 25° C. The nitrile-alcohol (IIb) obtained is then reduced into an amino-alcohol compound (II) which may be used in the general process of sulfonation. After sulfonation, there is then obtained compound (I) carrying a primary alcohol function.

All the compounds of formula (I), (Ia) and (Ib), which carry a primary alcohol function may be converted into compounds (I) which carry a carboxylic acid function,

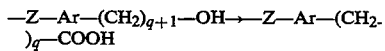

by oxidation of the alcoholic function, for example by the method of Jones (CrO$_3$/H$_2$SO$_4$) in a solvent such as acetone, at temperatures between −78° C. and 30° C., more particularly between −20° C. and 20° C., for a period of 1 to 96 hours, preferably between 2 and 16 hours.

Among the products of formula (I), and more specifically among those corresponding to formula (Ia), for which R$_3$ represents W, the stereochemically pure isomers, cis or trans, are obtained either by reaction with a stereochemically pure amine, cis or trans, or by reaction with a racemic amine, mixture of cis and trans isomers, followed by separation of the isomers by selective recrystallizations or by a chromatographic method (such as for example preparative high performance liquid chromatography liquid chromatography, flash chromatography, thin layer preparative chromatography). The mixtures of isomers and the pure products are analyzed by high performance liquid chromatography (H.P.L.C.), by ultra-violet detection.

Another possibility to directly and solely produce pure trans isomers, is the stereoselective synthesis, which is possible for the products of formula (I), and more specifically those of formula (Ia), in which R$_3$ is W and n=0. Starting from the aziridine of formula (III) by reaction with an organometallic derivative of a halide W-Cl, such as benzyl chloride, there is obtained a trans isomeric product, of structure (IV) in which W is Ar or —CH$_2$—Ar; R$_{1-2}$, R$_{4-6}$, Ar, Y have the meanings indicated above.

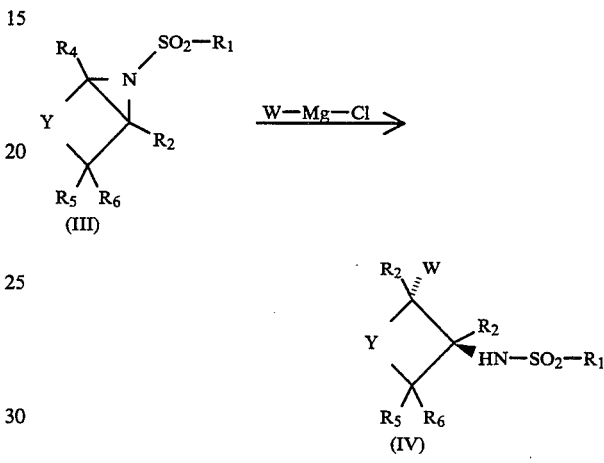

This reaction is carried out in a solvent such as diethyl ether, dibutyl ether, tetrahydrofuran or dioxane, at a temperature between −78° C. and the reflux temperature of the solvent, and more particularly between 0° C. and the reflux temperature of the solvent, by utilizing a molar ratio (III)/halide of 1:0.25 to 1:5, preferably 1:1 to 1:4. The metal required for the production of the organometallic compound is preferably magnesium. The time of reaction is generally comprised between 2 and 96 hours and more particularly between 16 and 48 hours.

The aziridines of formula (III) used in the stereospecific synthesis of the trans isomers are prepared from arylsulfonamides or heterocyclic sulfonamides (IIIa) according to the principle described by Ueno Y. et al., Chem. Pharm. Bull. (1967) 15, 1193–7. The sulfonamide derivatives (IIIa) converted into N,N-dibromosulfonamide derivatives (IIIb) by the action of bromine in the presence of a base, such as aqueous sodium hydroxide, react spontaneously with unsaturated compounds, such as alkenes of formula (IIIc) in molar excess, in a solvent, generally chloroform, at a temperature between −30° C. and the reflux temperature of the solvent, and more particularly between 0° C. and 50° C., for a period of time between 5 and 72 hours, and more specifically between 16 and 24 hours. The brominated intermediates (V) are thereafter cyclized by the action of a base in excess, such as sodium hydroxide or potassium hydroxide, in solvents such as methanol, ethanol, acetone, which are pure or mixed with water, at a temperature between −20° C. and the reflux temperature of the solvent, and preferably at 20° C. for a period of time between 5 and 48 hours, preferably between 14 to 16 hours, to give the aziridine (III). The substituents, R$_1$, R$_2$, R$_{4-6}$ and the parameter Y, mentioned in formulae (IIIa), (IIIb), (IIIc), (III) and (V) have the meanings defined previously.

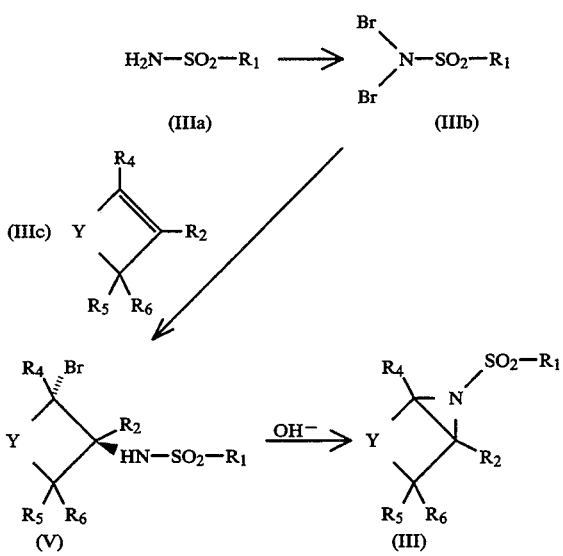

The brominated intermediates of formula (V) may also be used as starting reactants for the synthesis of the compounds of formula (I) and more specifically of formula (Ia) in which $R_3$ represents W, and Z which is comprised within W is an atom of oxygen. The brominated compounds of formula (V),

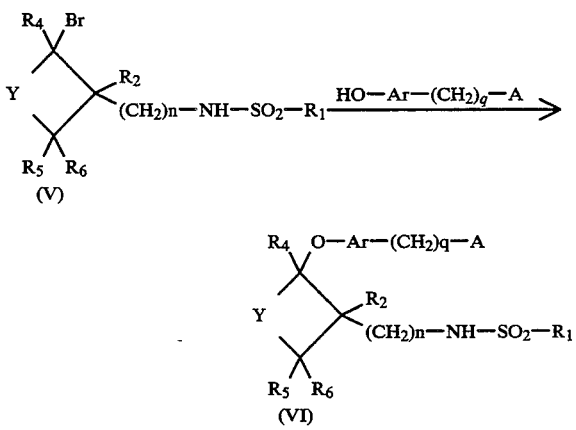

by O-alkylation of a phenol directly give compounds of formula (VI). In the structures (V) and (VI), the substituents $R_1$, $R_2$, $R_{4-6}$ and the parameters Y, Ar, A, n and q have the meanings defined previously. In formula (VI), when A is $CO_2H$, the carboxylic function is protected in the form of ester with a lower alkoxy radical. The reaction takes place with a molar excess of a phenolic derivative, in a known solvent for reactions of alkylation such as N,N-dimethylformamide, in the presence of a base such as potassium carbonate, sodium hydroxide, potassium hydroxide, in molar proportions phenol/base 1:0.5 to 1:10, preferably 1:2. The reaction is heated at a temperature between 40° and 200° C., preferably at 80° C. for a period of time between ½ hour and 16 hours, preferably from 3 to 6 hours.

The intermediate compounds for the preparation of the compounds of formula (I), (Ia) and (Ib), in particular those of formula (I), (IIb) or (IV), in which W is represented by $R_2$ or $R_3$ is a radical Ar or —$CH_2$—Ar, and more particularly when Ar represents the phenyl radical, may be converted into compounds of type (I) where W contains a carboxylic acid function. By a Friedel-Crafts acylation, there are obtained para-acylated derivatives which will be oxidized into esters (case where A is a group hydrolyzable into $CO_2H$) followed by saponification to give carboxylic acids (I). The Friedel-Crafts reaction is carried out by reacting acyl halides, such as acetyl chloride, ethyl 3-chloroformylpropionate, or anhydrides such as succinic anhydride, in the presence of a Lewis acid such as $SnCl_4$, $TiCl_4$ or $AlCl_3$, in a solvent such as

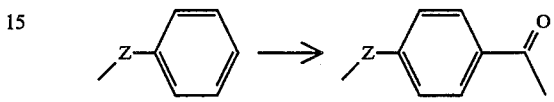

dichloromethane or 1,2-dichloroethane, at a temperature between —78° C. and the reflux temperature of the solvent and preferably between —30° C. and the reflux temperature of the solvent, for 4 to 30 hours. A molar excess of Lewis acid of 1.1 to 11 equivalents is used and more particularly from 3.3 to 7 equivalents as well as a molar excess of acyl halide or anhydride, from 1.1 to 4 equivalents, and preferably 1.2 to 2.2 equivalents.

All the acylated compounds may be converted into esters by oxidation with thallium nitrate ($Tl(NO_3)_3$) or lead tetraacetate in the presence of methanol and a Lewis acid such as perchloric acid or boron trifluoride etherate,

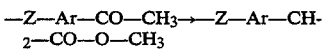

in a solvent such as dichloromethane, benzene, toluene or directly in methanol, between —50° C. and the reflux temperature of the solvent and more particularly between 20° C. and the reflux temperature of the solvent, for 5 to 40 hours. A molar excess of Lewis acid is used, from 1.1 to 11 equivalents. The thallium nitrate-montmorillonite K-10 complex has also been used to replace $Tl(NO_3)_3$ under the same conditions and in the same proportions, but in the absence of perchloric acid.

All the methyl esters are saponified under known conditions, with an equivalent or a molar excess of a base (sodium hydroxide, potassium hydroxide, lithium hydroxide or sodium bicarbonate)

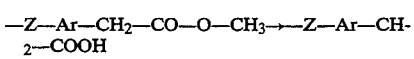

in water or in hydroalcoholic mixture (methanol or ethanol), in the presence or without tetrahydrofuran, at a temperature between 0° C. and the reflux temperature of the solvent or the mixture of solvents, preferably between 30° C. and the reflux temperature of the solvent or the mixture of solvents.

The compounds (I) carrying a carboxylic acid function may also be prepared from acylated derivatives by conversion into thiomorpholide derivatives (by reflux in morpholine in the presence of an excess of sulfur according to the so-called Willgerodt method), followed by a known basic hydrolysis.

The compounds of the invention have for example excellent antithrombotic and antiasthmatic properties in mammals, and particularly man, cat, dog, due to their effect on the $TXA_2$ receptors.

The antagonist activity $TXA_2$ has been demonstrated by the platelet antiaggregating effect and by the vascular spasmolytic effect.

(A) Inhibition of the platelet aggregation induced by U46619, a stable analogue of $TXA_2$ (9,11-dideoxy-11α,-9α-epoxymethanoprostaglandine $F_2α$):

the antagonist activity of $TXA_2$ is demonstrated in the platelet aggregation test described by BORN G. V. R. (Nature (1962) 194, 927–9), on platelets of guinea-pig. The tests determine a concentration of compound which inhibits at 50% ($CI_{50}$) a liminar aggregation induced by U46619. The activities of the compounds of the present invention are given in example 108.

(B) Inhibition of the U46619 induced rat aorta vasoconstriction:

male rats weighing about 300 g are put to death by euthanasia; the thoracic aorta is rapidly taken out. A sample of about 1 cm is cut into a spiral, and placed in a vat containing 20 ml of nutrient medium (Krebs-Henseleit) kept a 37° C. and oxygenated ($O_2$ 95%, $CO_2$ 5%). The contractions are recorded with an isotonic strain gauge. After a rest of 45 mn, supramaximum contractions are provoked by the addition of an analogue of $TXA_2$ (U46619: 142 nM) to the survival medium. A plateau is generally reached after 10 mn of contact, the latter not exceeding 25 mn. A rest of 30 mn and a plurality of rinses take place after each contraction. The products are added 10 mn after U46619 and allowed to rest 15 mn, after which delay the inhibition is measured. The inhibitory concentration 50 (IC) is determined for each compound studied and on a minimum of 3 aortas. The activities of the compounds of the present invention are described in example 108.

The products of this invention also possess a hypocholesterolemia activity, by action on the biosynthesis of cholesterol, by inhibiting for example the HMG CoA reductase.

The products of this invention also possess an activity against the complications associated with diabetic pathology, such as neuropathies, nephropathies, retinopathies, cataracts due to the accumulation of sorbitol. The products of the invention prevent the synthesis of sorbitol, by inhibition of the aldose reductase.

The compounds of this invention are characterized by their absence of toxicity. By way of illustration, for the compound described in example 20, the lethal dose 50 determined on the rat, by intravenous injection is higher than 150 mg/kg.

The products of the invention are characterized, in that they can be used with compositions containing an efficient quantity of at least one compound of formula (I), in association with a pharmaceutically acceptable carrier. These pharmaceutical compositions which can be administered to mammals, are used by oral, intravenous, intraarterial, cutaneous, intestinal or aerosol administration. Moreover, these new products have an extended lifetime, notwithstanding the mode of administration.

The products of general formula (I) are associated in pharmaceutical form to adequate carriers, aromas and dyes to constitute for example tablets, in addition in liposome form, microcapsules or nanocapsules, pellicular tablets, capsules, solutions, injectable aqueous solutions, suppositories, aerosols or creams. The carriers used can for example consist of microcrystalline cellulose, lactose, polyvidone, sodium glycolate of starch, talc, magnesium stearate. The carriers for the liposome forms, microcapsules and nanocapsules may be polyalkylcyanoacrylates, phospholipids. The coating of the tablets may be carried out with additives such as hydroxypropylmethylcellulose, various acrylic polymers, propyleneglycol and titane dioxide. The preparations for oral administration may contain artificial aromas and sweeteners such as sugar, aspartam. The preparations for injectable aqueous solutions are made with water which contains stabilization, solubilization agents, such as sodium chloride, mannitol and sorbitol and/or buffers which are necessary for the injectable solutions. The preparations for suppositories may use carriers such as semi-synthetic glycerides. The cream preparations will be carried out inter alia by the addition of non ionic tensio-active agents. The preparations for administration by aerosol will be carried out from the micronized active agent, associated to a tensio-active agent such as sorbitan trioleate, in a carrier gas such as CFC 11 and 12.

The products of this invention strongly inhibit the biological activities of $TXA_2$, by antagonist effect on the receptors $TXA_2$. They may be used for the treatment or the prophylaxy of ischemic diseases (such as myocardial infarction, angina pectoris, thrombosis), cerebrovascular diseases (such as transitory ischemic attack, migraine, cerebral hemorrhage, cerebral infarction), peripheric vascular diseases and diseases caused by lipidic unbalances (such as atherosclerosis, capillar convulsion, disorders of peripheric circulation, hypertension, abortion and uterine growth delay, diabetic nephropathy, retinopathy, troubles of menstruation, pulmonary embolism), allergic and inflammatory diseases (such as bronchial asthma, bronchitis, pneumonia, respiratory distress syndrome, allergic shock, gastric ulcer, glomerular nephritis, hydronephritis, lupus erythematosus). They are used against the formation of thrombus for example in the extrabody blood circulation, in prophylaxy or in treatment of peri and post-surgery thrombotic complications following transplantation of organs and the nephrotoxicity of cyclosporine, aorto-coronary bypasses, angioplasty, endarterectomy, thrombolysis and the secondary effects of the neutralization of heparine with protamine.

The products of this invention may also be used in association with any other substance used in therapeutics, for example thrombolytic substances (streptokinase, urokinase, activators of plasminogen . . . ), inhibitors of phosphodiesterases, stable analogues of protacycline, inhibitors of cyclooxygenase, inhibitors of the thromboxane synthetase, anticoagulants (antivitaminic K agents, heparines, heparines of low molecular weight), peripheric and central vasodilators, antagonists of receptors $S_2$ of serotonine, antihistamine agents, antagonists of PAF-acether, activators of potassium channels.

The daily doses of active agent, administered in one or more times, should be between 0.01 and 100 mg/kg of body weight, preferably between 0.1 and 50 mg/kg.

The following examples illustrate the invention without limitation. In the data of nuclear magnetic resonance (N.M.R.), the following abbreviations have been used: s for singulet, d for doublet, t for triplet, q for quadruplet and m for complex massive, the chemical displacements δ are expressed in ppm. The analyses by high performance liquid chromatography (H.P.L.C.), have been carried out on a Spherisorb column 5 μm, length=15 cm, diameter=0,46 cm, whose nature is specified by the following abbreviations: Si for silica and ODS-2 for C-18 reverse phase "end-capped". The mobile phase used on the column of silica is a mixture of hexane and ethyl acetate, in the proportions mentioned each time; on an ODS-2 column, a methanol-water-acetic acid mixture [57:43:0.01] is used. The flow used is of 1 ml/mn and the detection is realized by spectrophotometry at 254 nm. The retention times, $t_R$, are indicated in minutes.

EXAMPLE 1

Trans-4-[[2-[[(4-chlorophenyl)sulfonyl]amino]cyclopentyl]methyl]-benzeneacetic acid a) Ethyl 4-[(2-hydroxyiminocyclopentyl)methyl]benzene acetate A suspension of 10g (0.04 mole) of 4-[(2-hydroxyiminocyclopentyl)methyl]benzeneacetic acid (prepared according to Terada A. et al., J. Med. Chem. (1984) 27, 212–6) in 70 ml of anhydrous ethanol is saturated with gaseous HCl, while keeping the temperature of the reaction mixture at about 10° C. by means of a bath of ice and salt. After saturation, the solution obtained is stirred at room temperature during 1 hour, before being concentrated to dryness under vacuum. The residue is dissolved in ethyl acetate, successively washed with a saturated solution of NaHCO$_3$ and H$_2$O. The organic phase dried on Na$_2$SO$_4$ is evaporated, gives 11.05 g (yield=99.5%) of a brown thick oil which is partially crystallized and is used without any other purification.

I.R. (film): $\nu$ (N—OH)=3250 cm$^{-1}$; (C=O)=1725 cm$^{-1}$. N.M.R. (CDCl$_3$): $\delta$=1.2 (3H,t, J=6.75 Hz); 1.6–3.2 (9H, m); 3.5 (2H,s); 4.1 (2H,q, J=6.75 Hz); 7.1 (4H,s); 9.0 (1H,s wide, exchangeable with CF$_3$COOD).

Another method is also possible: a mixture of 5.8 g of 4-[(2-hydroxyiminocylcopentyl)methyl]-benzeneacetic acid, 4.1 ml of ethanol 98° and 2 drops of concentrated H$_2$SO$_4$ in 20 ml of toluene is refluxed for 6 hours, in a reactor above which there is a Dean-Stark separator. After cooling, the toluene is washed with a solution of NaHCO$_3$, then with H$_2$O. The organic phase is dried over Na$_2$SO$_4$ and is concentrated. The product obtained is in the form of a yellow oil.

b) Ethyl 4-[(2-aminocyclopentyl)methyl]benzeneacetate (cis+trans)

In an autoclave, a solution of 75.1 g (0.27 mole) of ethyl 4-[(2-hydroxyiminocyclopentyl)methyl]benzeneacetate in 800 ml of anhydrous ethanol saturated with NH$_3$ is combined with about 37.5 g of Raney Nickel in water. The mixture is stirred under 80 atmospheres of hydrogen, at 80° C. during 4 hours. After cooling, the catalyst is filtered and rinsed with ethanol. The concentrated filtrate under reduced pressure, gives 69.3 g (yield=98.3%) of an orange oil which crystallizes but which is used without any other purification.

I.R. (film): $\nu$ (NH$_2$)=3300 cm$^{-1}$; (C=O)=1715 cm$^{-1}$. N.M.R. (CDCl$_3$): $\delta$=1.2 (3H,t, J=6.75 Hz); 1.5 (2H,m); 1.6–3.25 (10H,m, including 2H exchangeable with CF$_3$CO$_2$D); 3.55 (2H,s); 4.1 (2H,q, J=6.75 Hz); 7.1 (4H,s).

This compound may also be obtained by hydrogenation under low pressure of hydrogen (3 atmospheres) at 25° C.

c) Ethyl 4-[2-[[(4-chlorophenyl)sulfonyl]amino]cyclopentyl]methyl]benzeneacetate (cis+trans)

A mixture of 2.25 g (8.6 mmoles) of the amine prepared in example 1b, of 1.45 ml (10.3 mmoles) of triethylamine and 70 ml of CH$_2$Cl$_2$, is brought to 10° C. with a bath of ice and water. A solution of 1.9 g (9 mmoles) of 4-chlorobenzenesulfonyl chloride in 5 ml of ether is added dropwise during 3 mn. The mixture is allowed to reach room temperature and is stirred for 2 hours. It is thereafter poured on 150 g of ice and water and is acidified at pH 1 while stirring with HCl 6N. CH$_2$Cl$_2$ is decanted and an extraction is again carried out with 100 ml of CH$_2$Cl$_2$. The combined organic phases are washed with H$_2$O, followed by drying over Na$_2$SO$_4$ before being concentrated. The yellow oil obtained is purified by flash chromatography on a column of silica with a mixture of hexane and ethyl acetate 5/1, to give 3.35 g (yield=89.3%) of a very pale yellow oil, which slowly crystallizes.

I.R. (film): $\nu$ (NH)=3250 cm$^{-1}$; (C=O)=1725 cm$^{-1}$; (SO$_2$)=1320 cm$^{-1}$; (SO$_2$)=1150 cm$^{-1}$. N.M.R. (CDCl$_3$): $\delta$=1.2 (3H,t, J=6.75 Hz); 1.15–1.9 (6H,m); 1.9–3.9 (4H,m); 3.6 (2H,s); 4.15 (2H,q, J=6.75 Hz); 5,4 (1H, dd, J=8.25 Hz, exchangeable in D$_2$O); 7.0 (4H,m); 7.4 (2H,m); 7.8 (2H,m). H.P.L.C. (Si; hexane-ethyl acetate 8:1): $t_R$=14.1 (42%); 16.0 (58%).

d) Trans-4-[[2-[[(4-chlorophenyl)sulfonyl]amino]cyclopentyl]methyl]benzeneacetic acid To a solution of 95.25 g (0.218 mole) of ethyl ester prepared in example 1c, and 1200 ml of ethanol 98°, are added 24.4 g (0.435 mole) of KOH dissolved in 360 ml of water. The mixture is stirred 3 hours at 40° C. Ethanol is evaporated under reduced pressure. The residue, dissolved in water, is washed with ethyl acetate. The aqeuous phase is acidified while cold, at pH 1, with HCl 6N. The precipitate formed is dissolved with ethyl acetate. This organic phase washed with H$_2$O until neutrality, is dried over Na$_2$SO$_4$, and concentrated under vacuum. There is obtained 75.9 g of a solid cream which is recrystallized four times in ethyl acetate to give 11 g of white flakes-trans isomer-(yield=12.4%). M.P.=164°–5° C. The treatment of the mother liquors enables to recover 1.2 g of a products of the same purity (total yield=13.9%).

| Percentage analysis: C$_{20}$H$_{22}$ClNO$_4$S (MW = 407.912) | | | | | |
|---|---|---|---|---|---|
| | C % | H % | Cl % | N % | S % |
| Calculated | 58.89 | 5.44 | 8.69 | 3.43 | 7.86 |
| Found | 58.75 | 5.30 | 8.74 | 3.47 | 7.73 |

I.R. (KBr): $\nu$ (NH)=3250 cm$^{-1}$; (C=O)=1690 $^{-1}$; (SO$_2$)=1320 cm$^{-1}$; (SO$_2$)=1150 cm$^{-1}$. N.M.R. (acetone-d$_6$): $\delta$=1.15–1.9 (6H,m); 1.9–2.05 (1H,m); 2.3 (1H,m, J$_{H-H}$gem=13 Hz); 2.8 (1H,m, J$_{H-H}$gem=13 Hz); 3.3 (1H,m, J$_{CH-NH}$=7.8 Hz); 3.6 (2H,s); 6.7 (1H,d, J$_{NH-CH}$=7.8 Hz, exchangeable with CF$_3$COOD); 7.0–7.1 (2H,m); 7.15–7.25 (2H,m); 7.55–7.65 (2H,m); 7.8–7.9 (2H,m); 10.55 (1H,s, exchangeable with CF$_3$COOD). H.P.L.C. (ODS-2): $t_R$=30.15 (100%). Before recrystallization $t_R$=27.0; 30.0; these two peaks of equal intensity correspond to the cis and trans isomers.

EXAMPLE 2

Sodium trans-4-[[2-[[(4-chlorophenyl)sulfonyl]amino]-cyclopentyl]methyl]benzene-acetate To a suspension of 3.9 g (9.6 mmoles) of trans-4-[[2-[[(4-chlorophenyl)sulfonyl]amino]cyclopentyl]methyl]-benzeneacetic acid in 50 ml of distilled water are added 0.38 g (9.6 mmoles) of NaOH dissolved in 30 ml of distilled water. The mixture is heated on a water-bath at 50° C. until complete solubilization, before being filtered, and left a few hours in a refrigerator. The white precipitate obtained is filtered, rinsed with distilled water. The residual water is removed by azeotropic distillation with toluene. The product obtained is recrystallized in distilled water. White solid. (Yield=57.0.%). M.P.=212°–4° C.

| Percentage analysis: $C_{20}H_{21}ClNNaO_4S$ (MW = 429.894) | | | | | |
|---|---|---|---|---|---|
| | C % | H % | Cl % | N % | Na % | S % |
| Calculated | 55.88 | 4.92 | 8.25 | 3.26 | 5.35 | 7.46 |
| Found | 55.67 | 5.02 | 8.31 | 3.16 | 5.50 | 6.99 |

I.R. (KBr): $\nu$ (NH)=3260 cm$^{-1}$; (SO$_2$)=1315 cm$^{-1}$; (SO$_2$)=1140 cm$^{-1}$. N.M.R. (DMSO d$_6$): $\delta$=0.7–1.6 (6H,m); 1.6–2.4 (3H,m); 2.6–3.7 (2H,m, 1H exchangeable with CF$_3$COOD); 3.2 (2H,s); 6.7–7.35 (4H,m); 7.6–8.1(4H,m). H.P.L.C. (ODS-2): 1 single peak having one $t_R$ identical to the product of example 1d.

EXAMPLE 3

Cis-4-[[2-[[(4-chlorophenyl)sulfonyl]amino]cyclopentyl]methyl]benzeneacetic acid Starting from the mother liquors of the first recrystallization of the product for example 1d and by salting out the trans isomer in a mixture of ethyl acetate-hexane, 1.1 g of pure cis isomer is isolated. White solid. M.P.=142°–5° C.

| Percentage analysis: $C_{20}H_{22}ClNO_4S$ (MW = 407.912) | | | | | |
|---|---|---|---|---|---|
| | C % | H % | Cl % | N % | S % |
| Calculated | 58.89 | 5.44 | 8.69 | 3.43 | 7.86 |
| Found | 58.80 | 5.56 | 8.90 | 3.41 | 7.70 |

I.R. (KBr): $\nu$ (NH)=3230 cm$^{-1}$; (C=O)=1690 cm$^{-1}$; (SO$_2$)=1315 cm$^{-1}$; (SO$_2$)=1150 cm$^{-1}$. N.M.R. (acetone d$_6$): $\delta$=1.15–1.85 (6H,m); 2.05–2.25 (1H,m); 2.35 (1H,m); 2.8 (1H,m); 3.6 (2H,s); 3.7 (1H,m, $J_{CH\text{-}NH}$=8.7 Hz); 6.6 (1H,d, $J_{NH\text{-}CH}$=8.7 Hz, exchangeable with CF$_3$COOD); 7.0–7.1 (2H,m); 7.15–7.25 (2H,m); 7.6–7.7 (2H,m); 7.85–7.95 (2H,m); 9.5 to 10.4 (1H,s wide, exchangeable with CF$_3$COOD). H.P.L.C. (ODS-2): $t_R$=25.2 (99.4% - cis isomer); 28.2 (0.6% -trans isomer).

EXAMPLE 4

Trans-4-[[2-[[(4-fluorophenyl)sulfonyl]amino]cyclopentyl]methyl]benzeneacetic acid a) Ethyl 4-[[2-[[(4-fluorophenyl)sulfonyl]amino]cyclopentyl]methyl]benzeneacetate (cis+trans)

Obtained by operating as in example 1c from 5.9 g (22.6 mmoles) of ethyl 4-[(2-aminocyclopentyl)methyl]benzeneacetate prepared in example 1b, and 4.6 g (23.6 mmoles) of 4-fluorobenzenesulfonyl chloride in the presence of 3.7 ml (26.7 mmoles) of triethylamine in 190 ml of a dichloromethane-ether mixture (8.5:1); stirring is carried out 16 hours at room temperature. Purification by chromatography on a column of silica with a hexane-ethyl acetate mixture (4:1) to give 5.1 g (yield=53.7%) of a yellow oil.

I.R. (film): $\nu$ (NH)=3250 cm$^{-1}$; (C=O)=1715 cm$^{-1}$; (SO$_2$)=1325 cm$^{-1}$; (SO$_2$)=1150 cm$^{-1}$. N.M.R. (CDCl$_3$): $\delta$=1.3 (3H,t, J=6.75 Hz); 1.0–1.9 (6H,m); 1.9–3.5 (4H,m); 3.6 (2H,d); 4.15 (2H,q, J=6.75 Hz); 5.2 (1H,dd, J=8.25 Hz, exchangeable with CF$_3$COOD); 6.8–7.4 (4H,m); 7.5–8.0 (4H,m). H.P.L.C. (Si, hexane-ethyl acetate 4:1): $t_R$=6.05 (41.8%); 6.6 (58.2%).

b) Trans-4-[[2-[[(4-fluorophenyl)sulfonyl]amino]cyclopentyl]methyl]benzeneacetic acid Obtained by operating as in example 1d from 4.5 g (10.7 mmoles) of ethyl ester obtained as in example 4a and from 1.2 g (21.4 mmoles) of KOH in an ethanol-water mixture. After many recrystallizations in hexane-ethyl acetate, there is obtained 0.3 g (yield =7.1%) of a white solid. M.P.=145°–8° C.

| Percentage analysis: $C_{20}H_{22}FNO_4S$ (MW = 391.457) | | | | | |
|---|---|---|---|---|---|
| | C% | H % | F % | N % | S % |
| Calculated | 61.37 | 5.66 | 4.85 | 3.58 | 8.19 |
| Found | 61.37 | 5.67 | 4.93 | 3.57 | 8.24 |

I.R. (KBr): $\nu$ (NH)=3250 cm$^{-1}$; (C=O)=1685 cm$^{-1}$; (SO$_2$)=1320 cm$^{-1}$; (SO$_2$)=1150 cm$^{-1}$. N.M.R. (DMSO d$_6$): $\delta$=0.8–1.6 (6H,m); 1.6–2.4 (3H,m); 2.4–3.7 (2H,m, 1H exchangeable with CF$_3$CO$_2$D); 3.5 (2H,s); 6.8–7.3 (4H,m); 7.4–8.1 (5H,m, with 1H exchangeable by CF$_3$CO$_2$D). H.P.L.C. (ODS-2): $t_R$=17.1 (0.9% -cis isomer); 18.8 (99.1% -trans isomer).

EXAMPLE 5

Trans-4-[[2-[[(4-chlorophenyl)sulfonyl]amino]cyclopentyl]methyl]-benzeneacetic acid a) N-(2-Bromocyclopentyl)-4-chlorobenzenesulfonamide A solution of 20 % caustic soda (270 ml, 1.80 mole) is poured dropwise during 30 minutes on a mixture of 128 g (0.67 mole) of 4-chlorobenzenesulfonamide and 400 g (2.5 moles) of bromine under high stirring. During the addition the temperature is kept at 5° C. by means of a bath of ice and water. The reaction mixture is thereafter stirred 30 minutes at room temperature, before filtering the yellow orange precipitate formed. After washing with water, there is obtained a yellow solid, melting at 104°–8° C. (M.P.=102° C. according to Baxter R. R. and Chattaway F. D., J. Chem. Soc. (1915) 1814–23) which is recaptured with 600 ml of warm chloroform. The residual water is decanted. This chloroformic phase is added dropwise during 45 minutes to 235 ml (2.67 moles) of cyclopentene maintained at a temperature of 5° C. The solution obtained is thereafter stirred 22 hours at room temperature, before being washed with H$_2$O, dried over Na$_2$SO$_4$ and concentrated under reduced pressure. The residue is purified by recrystallization in a mixture of ethyl acetate and hexane. There is obtained 140.2 g of a white solid. (Yield=62%). M.P.=113°–8° C.

I.R. (KBr): $\nu$ (NH)=3240 cm$^{-1}$. N.M.R. (CDCl$_3$): $\delta$=1.25–2.5 (6H,m); 3.7 (1H,m); 4.1 (1H,m); 5.3 (1H,d, J=6.75 Hz, exchangeable with CF$_3$COOD); 7.35–7.7 (2H,m); 7.7–8.05 (2H,m).

b) 6-[(4-Chlorophenyl)sulfonyl]-6-azabicyclo[3.1.0]hexane

A suspension of 140 g (0.413 mole) of the product prepared in example 5a, in 670 ml of ethanol is heated until solubilization. A solution of NaOH 20% (80.5 ml, 0.537 mole) is then rapidly added. The reaction mixture is allowed to return to room temperature, under stirring, before concentrating same to dryness under reduced pressure. The residue captured with ethyl acetate is washed with water, dried over sodium sulfate and concentrated under vacuum. The residue is purified by chromatography on a column of silica (eluting agent:

hexane-ethyl acetate 9/1) to give 54 g of a white solid (yield=50.8%). M.P.=75°-6° C.

I.R. (KBr): $\nu$ (SO$_2$)=1310 cm$^{-1}$; (SO$_2$)=1150 cm$^{-1}$. N.M.R. (CDCl$_3$): $\delta$=1.3-2.3 (6H,m); 3.4 (2H,s); 7.3-7.6 (2H,m); 7.7-8.0 (2H,m).

c) Trans-4-chloro-N-[2-(phenyl)methyl]cyclopentyl]-benzenesulfonamide

To a solution of 0.27 mole of phenylmethylmagnesium chloride (prepared from 6.7 g of magnesium turnings and 31.5 ml of chloromethylbenzene in 105 ml of anhydrous ether) under a flow of nitrogen, kept at 0° C., there is added dropwise 35.3 g (0.137 mole) of the compound prepared in example 5b dissolved in 300 ml of anhydrous ether. The reaction mixture is stirred 20 hours at 20° C. After cooling at 0° C., the magnesium complex in excess is destroyed by the addition of 210 ml of a saturated solution of ammonium chloride. After dissolution of the inorganic white precipitate formed with water saturated with NaCl, the mixture is extracted twice with ethyl acetate. The organic phase washed with H$_2$O, dried over Na$_2$SO$_4$ and concentrated, gives an oil which, after grinding in hexane, gives 30.5 g (yield=63.7%) of a white solid used without any other purification. M.P.=66°-8° C.

I.R. (KBr): $\nu$ (NH)=3260 cm$^{-1}$; (SO$_2$)=1320 cm$^{-1}$; (SO$_2$)=1150 cm$^{-1}$. N.M.R. (CDCl$_3$): $\delta$=0.9-2.3 (7H,m); 2.35-2.95 (2H,m); 3.2 (1H,m); 4.9 (1H,d, J=6.75 Hz, exchangeable with CF$_3$COOD); 6.8-7.5 (7H,m); 7.6-7.9 (2H,m).

d) Trans-N-[2-[(4-acetylphenyl)methyl]cylcopentyl]-4-chlorobenzenesulfonamide

To a mixture of 30.5 g (87 mmoles) of the compound prepared in example 5c and 690 ml of dichloromethane maintained between $-30°$ and $-20°$ C., there is added 15 g (191 mmoles) of acetyl chloride, then by portions during 1 hour, 46.4 g (348 mmoles) of anhydrous aluminum chloride. The orange reaction mixture is maintained at $-30°$ C. during 3.5 hours before being poured over a mixture of ice+concentrated hydrochloric acid, and is extracted with dichloromethane. The organic phase is washed with water, dried over Na$_2$SO$_4$ and concentrated. The residue obtained is purified by chromatography on a column of silica (eluant: hexane-ethyl acetate 10/1 then 2/1) to give 14.8 g (yield=43.5%) of a brown orange oil.

I.R. (film): $\nu$ (NH)=3250 cm$^{-1}$; (C=O)=1660 cm$^{-1}$; (SO$_2$)=1320 cm$^{-1}$; (SO$_2$)=1150 cm$^{-1}$. N.M.R. (CDCl$_3$): $\delta$=0.8-2.1 (7H,m); 2.1-2.95 (2H,m); 2.55 (3H,s); 3.2 (1H,m); 5.2 (1H,d, J=8.25 Hz, exchangeable with CF$_3$COOD); 6.8-8.0 (8H,m).

e) Methyl trans-4-[[2-[[(4-chlorophenyl)sulfonyl]amino]cyclopentyl]methyl]benzeneacetate To a mixture of 14.8 g (38 mmoles) of the compound prepared in example 5d, 18 ml of methanol and 90 ml of dichloromethane, under a flow of nitrogen, and maintained at 0° C., there is added dropwise 18.7 ml (152 mmoles) of boron trifluoride etherate. This mixture is stirred 15 minutes at room temperature before being poured, all at once in a suspension of 17.5 g (39.5 mmoles) of lead tetraacetate in 105 ml of benzene, under nitrogen, maintained at 10° C. The orange-colored reaction mixture is stirred 22 hours at room temperature before being poured over ice, and extracted with dichloromethane. The organic phase washed with H$_2$O, dried on Na$_2$SO$_4$ and concentrated gives an oil which after grinding in hexane gives 13.2 g (yield=82.5%) of a beige solid used without any other purification. M.P.=80° C.

I.R. (KBr): $\nu$ (NH)=3200 cm$^{-1}$; (C=O)=1690 cm$^{-1}$; (SO$_2$)=1320 cm$^{-1}$; (SO$_2$)=1150 cm$^{-1}$. N.M.R. (CDCl$_3$): $\delta$=0.9-2.2 (7H,m); 2.3-2.9 (2H,m); 3.0-3.4 (1H,m); 3.6 (2H,s); 3.65 (3H,s); 5.0 (1H,d, J=8.25 Hz, exchangeable with CF$_3$COOD); 6.8-7.25 (4H,m); 7.3-7.5 (2H,m); 7.6-7.9 (2H,m). H.P.L.C. (Si, hexane-ethyl acetate 8:1): $t_R$=19.0 (1 single peak).

f) Trans-4-[[2-[[(4-chlorophenyl)sulfonyl]amino]cyclopentyl]methyl]benzeneacetic acid A mixture of 3.5 g (62.5 mmoles) of KOH in pellets form in 120 ml of water and of 13.2 g (31 mmoles) of the compound prepared in example 5e dissolved in 300 ml of ethanol is stirred at 40° C. during 2 hours. The ethanol is thereafter concentrated under reduced pressure and the residual aqueous phase is washed with ether. The acidification of the aqueous phase enables to give a beige precipitate, which after bleaching with carbon black and recrystallization in toluene, then in ethyl acetate gives 4.6 g (yield=36.5%) of white flakes having all the physical, spectral and chromatographic characteristics of the product described in example 1d.

EXAMPLE 6

Trans-4-[[2-[[(phenyl)sulfonyl]amino]cyclopentyl]methyl]benzeneacetic acid a) 6-(Phenylsulfonyl)-6-azabicyclo[3.1.0]hexane A solution of 93 g (0.306 mole) of N-(DL-trans-2-bromocyclopentyl)-benzenesulfonamide (prepared according to Ueno Y. et al., Chem. Pharm. Bull. (1967) 15, 1328-30), of 610 ml of acetone and 61 ml of NaOH 30% is refluxed 2 mn, then stirred 16 hours at room temperature. After concentration under reduced pressure, the residue is captured by water and extracted with ether. The organic phase washed with water is dried over Na$_2$SO$_4$ and concentrated under vacuum to give 67.5 g (yield=99.0%) of a clear yellow oil, used without other purification. A fraction of this product is purified by chromatography over silica (hexane-ethyl acetate 2/1 mixture) to give a colorless oil. b.p.$_{0.5}$=137°-9° C.

| Percentage analysis: C$_{11}$H$_{13}$NO$_2$S (MW = 223,29) | | | | |
|---|---|---|---|---|
| | C % | H % | N % | S % |
| Calculated | 59.17 | 5.87 | 6.27 | 14.36 |
| Found | 59.47 | 5.88 | 6.16 | 14.37 |

I.R. (film): $\nu$ (SO$_2$)=1310 cm$^{-1}$; (SO$_2$)=1150 cm$^{-1}$. N.M.R. (CDCl$_3$): $\delta$=1.0-2.35 (6H,m); 3.4 (2H,s); 7.25-7.75 (3H,m); 7.75-8.2 (2H,m).

b) Trans-N-[2-[(phenyl)methyl]cyclopentyl]-benzenesulfonamide

Obtained by operating as in example 5c from 1.65 mole of phenylmethylmagnesium chloride and 184.3 g (0.825 mole) of the compound prepared in example 6a, in 2250 ml of anhydrous ether. There are obtained 249.8 g (yield=96.0%) of a white solid used without any other purification. M.P. 89°-91° C. A portion of this product was recrystallized twice in a hexane-ethyl acetate mixture to give a white solid. M.P.=96°-98° C.

| Percentage analysis: C$_{18}$H$_{21}$NO$_2$S (MW = 315.43) | | | | |
|---|---|---|---|---|
| | C % | H % | N % | S % |
| Calculated | 68.54 | 6.71 | 4.44 | 10.16 |
| Found | 68.69 | 6.74 | 4.33 | 10.13 |

I.R. (KBr): ν (NH)=3210 cm$^{-1}$; (SO$_2$)=1310 cm$^{-1}$; (SO$_2$)=1140 cm$^{-1}$. N.M.R. (CDCl$_3$): δ=1.0–2.3 (7H,m); 2.3–2.8 (2H,m); 3.1–3.5 (1H,m); 4.9 (1H,d, J=7.5 Hz, exchangeable with CF$_3$COOD); 6.85–7.35 (5H,m); 7.4–7.65 (3H,m); 7.7–8.0 (2H,m).

c) Trans-N-[2-[(4-acetylphenyl)methyl]cyclopentyl]-benzenesulfonamide

Obtained by operating as in example 5d from 13.2 g (41.8 mmoles) of the compound prepared in example 6b, 6.5 ml (91.9 mmoles) of acetyl chloride, 22.3 g (167 mmoles) of anhydrous aluminum chloride in 330 ml of 1,2-dichloroethane. Stirring 4.5 hours at −20° C. The purification by chromatography on a column of silica (eluant=hexane-ethyl acetate 2/1) gives 13.2 g (yield=88.6%) of a pale yellow solid, M.P.=78° C., used without any other purification. A sample recrystallized in a hexane-ethyl acetate mixture gives a white solid with yellow reflections melting at 90°–2° C.

| Percentage analysis: C$_{20}$H$_{23}$NO$_3$S (MW = 357.468) | | | | |
|---|---|---|---|---|
| | C % | H % | N % | S % |
| Calculated | 67.20 | 6.49 | 3.92 | 8.97 |
| Found | 67.40 | 6.34 | 3.97 | 9.29 |

I.R. (film): ν (NH)=3250 cm$^{-1}$; (C=O)=1660 cm$^{-1}$; (SO$_2$)=1315 cm$^{-1}$; (SO$_2$)=1150 cm$^{-1}$. N.M.R. (CDCl$_3$): δ=0.75–1.9 (7H,m); 1.9–2.9 (2H,m); 2.5 (3H,s); 2.95–3.4 (1H,m); 5.35 (1H,d, J =8.25 Hz, exchangeable with CF$_3$COOD); 6.7–7.25 (2H,m); 7.35–8.1 (7H,m).

d) Methyl trans-4-[[2-[[(phenyl)sulfonyl]amino]cyclopentyl]methyl]benzeneacetate To a mixture of 12.9 g (36 mmoles) of the compound prepared in example 6c, 110 ml of methanol and 18 ml of 70% perchloric acid, there is added by portions 19.2 g (43.2 mmoles) of thallium nitrate trihydrate. After stirring 25 hours at room temperature, the precipitate formed is filtered and rinsed with methanol. The filtrate diluted with water is extracted with dichloromethane. The organic phase rinsed with water, dried over Na$_2$SO$_4$ is concentrated under reduced pressure. The residue purified by chromatography on a column of silica (eluant:hexane-ethyl acetate 2/1) gives 7.4 g (yield=53.2%) of a beige solid. M.P.=88°–90° C.

I.R. (KBr): ν (NH)=3205 cm$^{-1}$; (C=O)=1695 cm$^{-1}$; (SO$_2$)=1320 cm$^{-1}$; (SO$_2$)=1150 cm$^{-1}$. N.M.R. (CDCl$_3$): δ=1.0–2.2 (7H,m); 2.2–2.9 (2H,m); 3.0–3.4 (1H,m); 3.5 (2H,s); 3.6 (3H,s); 5.05 (1H,d, J=7.5 Hz, exchangeable with CF$_3$COOD); 6.75–7.25 (4H,m); 7.3–7.6 (3H,m); 7.65–7.9 (2H, m).

There is obtained an identical product by oxidation of the compound of example 6c with lead tetraacetate under the conditions described in example 5e, followed by a purification by chromatography on a column of silica. An additional recrystallization in a hexane-ethyl acetate mixture gives a white solid. M.P.=91°–3° C.

| Percentage analysis: C$_{21}$H$_{25}$NO$_4$S (MW = 387.494) | | | | |
|---|---|---|---|---|
| | C % | H % | N % | S % |
| Calculated | 65.09 | 6.50 | 3.61 | 8.27 |
| Found | 65.18 | 6.53 | 3.58 | 8.20 | e) Trans-4-[[2-[[(phenyl)sulfonyl]amino]cyclopentyl]-methylbenzeneacetic acid

Obtained by operating as in example 5f from 4.6 g (11.9 mmoles) of the compound prepared in example 6d and 1.3 g (23.2 mmoles) of KOH in an ethanol-water mixture. After recrystallization in toluene, there is obtained 3.4 g (yield =77.3%) of an off-white solid. M.P.=118°–20° C.

| Percentage analysis: C$_{20}$H$_{23}$NO$_4$S (MW = 373.467) | | | | |
|---|---|---|---|---|
| | C % | H % | N % | S % |
| Calculated | 64.32 | 6.21 | 3.75 | 8.58 |
| Found | 64.67 | 6.18 | 3.74 | 8.69 |

I.R. (KBr): ν (NH)=3250 cm$^{-1}$; (C=O)=1680 cm$^{-1}$; (SO$_2$)=1315 cm$^{-1}$; (SO$_2$)=1145 cm$^{-1}$. N.M.R. (DMSO d$_6$): δ=0.75–1.7 (7H,m); 1.7–2.3 (2H,m); 3.1–3.35 (1H,m); 3.5 (2H,s); 6.65–7.4 (4H,m); 7.4–8.1 (6H,m, 1H exchangeable with CF$_3$COOD), 12.2 (1H,s, exchangeable with CF$_3$COOD). H.P.L.C. (ODS-2): t$_R$=17.65 (1 single peak).

EXAMPLE 7

Trans-4-[[2-[[(4-methylphenyl)sulfonyl]amino]cyclopentyl]methyl]-benzeneacetic acid a) Trans-4-methyl-N-[2-[(phenyl)methyl]cyclopentyl]-benzenesulfonamide Obtained by operating as in example 5c from 0.3 mole of phenylmethylmagnesium chloride and 35 g (0.147 mole) of 6-[(4-methylphenyl)sulfonyl]-6-azabicyclo[3.1.0]hexane (prepared according to Hegedus L. S. and McKearin J. M., J. Am. Chem. Soc. (1982) 104, 2444–51, but obtained as a solid. Yield =70.2% -M.P.=70° C.) in 500 ml of anhydrous ether. 40.1 g (yield=83.0%) of a white solid used without any other purification is obtained. M.P.=73°–8° C.

I.R. (KBr): ν (NH)=3240 cm$^{-1}$; (SO$_2$)=1320 cm$^{-1}$; (SO$_2$)=1140 cm$^{-1}$. N.M.R. (CDCl$_3$): δ=0.75–2.85 (9H,m); 2.4 (3H,s); 3.0–3.45 (1H,m); 5.1 (1H,d, J=7.5 Hz, exchangeable with CF$_3$COOD); 6.75–7.4 (7H,m); 7.55–7.9 (2H,m).

b) Trans-N-[2-[(4-acetylphenyl)methyl]cyclopentyl]-4-methylbenzenesulfonamide

Obtained by operating as in example 5d from 10 g (30.3 mmoles) of the compound prepared in example 7a, 4.7 ml (66 mmoles) of acetyl chloride, 16.2 g (122 mmoles) of anhydrous aluminum chloride, in 240 ml of dichloromethane. Stirring 5 h at −30°–20° C. The purification by chromatography on a column of silica (eluant=hexane-ethyl acetate 4/1) gives 4.7 g (yield=42.0%) of an oil which crystallizes partially.

I.R. (film): ν (NH)=3250 cm$^{-1}$; (C=O)=1660 cm$^{-1}$; (SO$_2$)=1320 cm$^{-1}$; (SO$_2$)=1140 cm$^{-1}$. N.M.R. (CDCl$_3$): δ=0.65–3.6 (10H,m); 2.4 (3H,s); 2.55 (3H,s); 5.3 (1H,d, J=7.5 Hz, exchangeable with CF$_3$COOD); 6.9–7.4 (4H,m); 7.55–8.05 (4H,m).

c) Methyl trans-4-[[2-[[(4-methylphenyl)sulfonyl]amino]cyclopentyl]methyl]benzeneacetate Obtained by operating as in example 5e from 4.7 g (12.6 mmoles) of the compound prepared in example 7b, 6 ml of methanol, 6.2 ml (50.4 mmoles) of boron trifluoride etherate in 30 ml of dichloromethane, then 5.8 g (13.1 mmoles) of lead tetraacetate in 35 ml of benzene. The purification by chromatography on a column of silica (eluant=hexane-ethyl acetate 4/1) gives 2.7 g (yield=54.0%) of a clear yellow oil.

I.R. (film): ν (NH)=3240 cm$^{-1}$; (C=O)=1710 cm$^{-1}$; (SO$_2$)=1310 cm$^{-1}$; (SO)=1140 cm$^{-1}$. N.M.R. (CDCl$_3$): =0.9–3.4 (10H,m); 2.4 (3H,s); 3.6 (2H,s); 3.7

(3H,s); 4.8 (1H,d, J=7 Hz, exchangeable with $CF_3COOD$); 6.8–7.4 (6H,m); 7.6–7.85 (2H,m).

d) Trans-4-[[2-[[(4-methylphenyl)sulfonyl]amino]cyclopentyl]methyl]benzeneacetic acid Obtained by operating as in example 5f from 2.7 g (6.7 mmoles) of the compound prepared in example 7c and 0.75 g (13.4 mmoles) of KOH pellets in an ethanol-water mixture. By recrystallization in toluene there is obtained 0.6 g (yield=23.1%) of a white solid. M.P.=134°–5° C.

| Percentage analysis: $C_{21}H_{25}NO_4S$ (MW = 387.494) | | | | |
|---|---|---|---|---|
| | C % | H % | N % | S % |
| Calculated | 65.09 | 6.50 | 3.61 | 8.27 |
| Found | 65.53 | 6.55 | 3.61 | 8.17 |

I.R. (KBr): $\nu$ (NH)=3250 $cm^{-1}$; (C=O)=1690 $cm^{-1}$; ($SO_2$)=1320 $cm^{-1}$; ($SO_2$)=1145 $cm^{-1}$. N.M.R. (DMSO $d_6$): $\delta$=1.0–2.25 (8H,m); 2.4 (3H,s); 2.75–3.4 (2H,m); 3.5 (2H,s); 6.8–8.0 (6H,m); 8.0–8.5 (3H,m, 1H exchangeable with $CF_3COOD$); 12.3 (1H,s wide, exchangeable with $CF_3COOD$). H.P.L.C. (ODS-2): $t_R$=33.5 (1 single peak).

EXAMPLE 8

Ethyl trans-4-[[2-[[(4-chlorophenyl)sulfonyl]amino]cyclopentyl]methyl]benzeneacetate a) Ethyl trans-4-[(2-aminocyclopentyl)methyl]benzeneacetate 0.5 g (21 mmoles) of sodium is added to a mixture of 2.6 g (21 mmoles) of naphthalene and 20 ml of 1,2-dimethoxyethane, under a flow of nitrogen. After stirring 1 hour at 20° C., a solution of 2 g (5.2 mmoles) of methyl trans-4-[[2-[[(phenyl)sulfonyl]amino]cyclopentyl]methyl]benzeneacetate in 20 ml of 1,2-dimethoxyethane is added dropwise during 1 hour, at room temperature. After stirring 1 hour at 20° C., 40 ml of water are added dropwise, before washing with ethyl acetate. The aqueous phase acidified with diluted HCl is washed with ethyl acetate, before being concentrated to dryness under reduced pressure. The residue is captured by 50 ml of absolute ethanol and the white suspension obtained is saturated at 0° C. with gaseous HCl. After stirring 16 h at 20° C., the reaction mixture is concentrated under reduced pressure, captured with $H_2O$, made basic with $NH_4OH$ and extracted with ethyl acetate. This organic phase after washing with $H_2O$ saturated with NaCl is dried over $Na_2SO_4$, concentrated, to give 0.5 g (yield=39.3%) of a partially crystallized brown oil, which is used without any other purification.

I.R. (film): $\nu$ ($NH_2$)=3330 $cm^{-1}$; (C=O)=1710 $cm^{-1}$. N.M.R. ($CDCl_3$): $\delta$=1.2 (3H,t, J=6.75 Hz); 1.4–3.2 (12H,m, 2H exchangeable with $D_2O$); 3.55 (2H,s); 4.1 (2H,q, J=6.75 Hz); 7.1 (4H,s).

b) Ethyl trans-4-[[2-[[(4-chlorophenyl)sulfonyl]amino]cyclopentyl]methyl]benzeneacetate Obtained by operating as in example 1c from 0.5 g (1.9 mmole) of the compound prepared in example 8a, 0.25 g (2.5 mmoles) of triethylamine in 20 ml of dichloromethane and 0.4 g (1.9 mmole) of 4-chlorobenzenesulfonyl chloride in 15 ml of ether. Stirring during 20 hours at 20° C. 0.6 g (yield=72.3%) of a thick oil is obtained.

I.R. (film): $\nu$ (NH)=3260 $cm^{-1}$; (C=O)=1720 $cm^{-1}$; ($SO_2$) 1325 $cm^{-1}$; ($SO_2$)=1150 $cm^{-1}$. N.M.R. ($CDCl_3$): $\delta$=1.2 (3H,t, J=6.75 Hz); 1.2–3.4 (10H,m); 3.55 (2H,s); 4.1 (2H,q, J=6.75 Hz); 4.9 (1H,d, J=7.5 Hz, exchangeable with $D_2O$); 6.8–7.25 (4H,m); 7.3–7.5 (2H,m); 7.6–7.85 (2H,m).

EXAMPLE 9

4-[2-[[(4-chlorophenyl)sulfonyl]amino]cyclopentyloxy]benzeneacetic acid a) Ethyl 4-[2-[[(4-chlorophenyl)sulfonyl]amino]cyclopentyloxy]benzeneacetate A mixture of 2.5 g (15 mmoles) of methyl 4-hydroxybenzeneacetate, 4 g (30 mmoles) of $K_2CO_3$ and 30 ml of DMF is heated to 80° C. A solution of 5 g (14.8 mmoles) of N-(2-bromocyclopentyl)-4-chlorobenzenesulfonamide as in example 5a is added dropwise thereto, in 50 ml of DMF. The mixture is stirred 5 h at 80° C. After cooling, the solid which is present is filtered and rinsed with ethyl acetate. The filtrate which is diluted with water is extracted with ethyl acetate. The organic phase is washed with water, dried over $Na_2SO_4$ and concentrated under reduced pressure. The residue which is purified by chromatography on a column of silica (eluant:hexane-ethyl acetate 1/1) gives 6.2 g (yield=99.5%) of a yellow liquid.

I.R. (film): $\nu$ (NH)=3250 $cm^{-1}$; (C=O)=1710 $cm^{-1}$; ($SO_2$)=1320 $cm^{-1}$; ($SO_2$)=1150 $cm^{-1}$. N.M.R. ($CDCl_3$): $\delta$=1.0–2.35 (6H,m); 2.75–3.4 (1H,m); 3.55 (2H,s); 3.7 (3H,s); 4.5–4.9 (1H,m); 5.2–5.7 (1H,m, exchangeable with $CF_3COOD$); 6.5–7.6 (6H,m); 7.6–7.95 (2H,m).

b) 4-[2-[[(4-Chlorophenyl]sulfonyl]amino]cyclopentyloxy]benzeneacetic acid

Obtained by operating as in example 1d, from 6.2 g (14.6 mmoles) of the compound prepared in example 9a in 60 ml of ethanol and 1.6 g (28.6 mmoles) of KOH in 15 ml of water. After recrystallization in toluene, there is obtained 1.6 g (yield=27.1%) of an off-white solid. M.P.=136°–9° C.

| Percentage analysis: $C_{19}H_{20}ClNO_5S$ (MW = 409.884) | | | | | |
|---|---|---|---|---|---|
| | C % | H % | Cl % | N % | S % |
| Calculated | 55.68 | 4.92 | 8.65 | 3.42 | 7.82 |
| Found | 55.80 | 5.01 | 8.95 | 3.37 | 7.94 |

I.R. (KBr): $\nu$ (NH)=3280 $cm^{-1}$; (C=O)=1690 $cm^{-1}$; ($SO_2$)=1315 $cm^{-1}$; ($SO_2$)=1140 $cm^{-1}$. N.M.R. (acetone $d_6$): $\delta$=1.1–2.35 (6H,m); 3.2–3.8 (1H,m); 3.5 (2H,s); 4.3–4.65 (1H,m); 6.0–6.9 (3H,m, in which 1H is exchangeable in $CF_3COOD$); 7.0–7.25 (2H,m); 7.3–7.6 (2H,m); 7.7–7.9 (2H,m); 10.0–10.9 (1H,s wide, exchangeable with $CF_3COOD$). H.P.L.C. (ODS-2): $t_R$=24.8 (1 single peak).

EXAMPLE 10

Trans-4-[2-[[(4-chlorophenyl)sulfonyl]amino]cyclohexyl]benzeneacetic acid a) Trans-N-[2-(4-acetylphenyl)cyclohexyl]-4-chlorobenzenesulfonamide To a mixture maintained at 0° C. of 4.0 g (12 mmoles) of trans-4-chloro-N-(2-phenylcyclohexyl)-benzenesulfonamide (prepared according to Das P. C. et al., Indian J. Chem. (1974), 12, 1139–40), 80 ml of anhydrous dichloromethane and 2.4 g (31 mmoles) of acetyl chloride, 5.3 g (40 mmoles) of aluminum chloride are added by fractions. After 4 hours at 0° C., the reaction mixture is thrown onto an ice-HCl mixture before being extracted with dichloromethane. The organic phase is washed with water to neutrality, dried over Na₂SO₄ and concentrated. The residue is purified by chromatography on a column of silica (eluant:hexane-ethyl acetate 4/1) to give 2 g of a colorless oil (yield:42.5%).

I.R. (film): ν (NH)=3260 cm⁻¹; (C=O)=1665 cm⁻¹; (SO₂)=1315 cm⁻¹; (SO₂)=1150 cm⁻¹. N.M.R. (CDCl₃): δ=0.7-2.45 (8H,m); 2.6 (3H,s); 2.75-3.75 (2H,m); 4.8 (1H,d, J=7.5 Hz, exchangeable with CF₃COOD); 6.8-7.1 (2H,m); 7.1-7.4 (4H,m); 7.5-7.8 (2H,m).

b) Methyl trans-4-[2-[[(4-chlorophenyl)sulfonyl]amino]-cyclohexyl]benzeneacetate To a mixture of 4.7 g (12 mmoles) of trans-N-[2-(4-acetylphenyl)cyclohexyl]-4-chlorobenzenesulfonamide and 40 ml of methanol, are added dropwise at room temperature 6.1 ml (100 mmoles) of 70% perchloric acid and 6.4 g (14.4 mmoles) of thallium nitrate (III) by portions. The reaction mixture obtained is stirred 48 hours at room temperature. After filtration and washing with methanol of the white precipitate formed, the filtrate is thrown into water and is extracted with dichloromethane. The organic phase is rinsed with water, dried over Na₂SO₄ and concentrated to give 4 g of a colorless oil (yield=79.0%). This oil crystallizes in ether after grinding, to give white crystals. M.P.=107°-110° C.

I.R. (KBr): ν (NH)=3260 cm⁻¹; (C=O)=1705 cm⁻¹; (SO₂)=1315 cm⁻¹; (SO₂)=1150 cm⁻¹. N.M.R. (CDCl₃): δ=1.0-3.4 (10H,m); 3.55 (2H,s); 3.7 (3H,s); 4.15-4.5 (1H,m, exchangeable with CF₃COOD); 6.6-7.15 (4H,m); 7.2 (4H,s).

c) Trans-4-[2-[[(4-chlorophenyl)sulfonyl]amino]cyclohexyl]benzeneacetic acid

A mixture of 1.8 g (4.3 mmoles) of methyl trans-4-[2-[[(4-chlorophenyl)sulfonyl]amino]cyclohexyl]benzeneacetate, 18 ml ethanol, 18 ml water and 0.5 g (8.5 mmoles) of KOH pellets is heated 4 hours at 40° C. under stirring. The ethanol is thereafter removed under reduced pressure. The residue which is diluted with H₂O is washed with ether and acidified under cold condition with 5 ml of concentrated hydrochloric acid. The precipitate formed is filtered, rinsed with H₂O and dried in an oven overnight at 50° C. The product is purified by means of 2 recrystallizations in a hexane-ethyl acetate mixture to give 0.8 g (yield=47.0%) of a white solid. M.P.=147°-9° C.

| Percentage analysis: C₂₀H₂₂ClNO₄S (MW = 407.91) | | | | | |
|---|---|---|---|---|---|
| | C % | H % | Cl % | N % | S % |
| Calculated | 58.89 | 5.44 | 8.69 | 3.43 | 7.86 |
| Found | 59.12 | 5.35 | 8.86 | 3.36 | 8.20 |

I.R. (KBr): ν (NH)=3170 cm⁻¹; (C=O)=1700 cm⁻¹; (SO₂)=1300 cm⁻¹; (SO₂)=1140 cm⁻¹. N.M.R. (DMSO d₆): δ=0.8-2.3 (9H,m); 2.75-3.4 (1H,m); 3.45 (2H,s); 6.9 (4H,s); 7.3 (4H,s); 7.6 (1H,d, J=8.25 Hz, exchangeable with CF₃COOD); 12.15 (1H,s, exchangeable with CF₃COOD).

EXAMPLE 11

Trans-4-[[2-[[(4-chlorophenyl)sulfonyl]amino]cyclohexyl]methyl]benzeneacetic acid a) Ethyl 4-[(2-hydroxyiminocyclohexyl)methyl]benzeneacetate Obtained by operating as in example 1a from 16.4 g (62.7 mmoles) of 4-[(2-hydroxyiminocyclohexyl)methyl]benzeneacetic acid (prepared according to Terada A. et al., J. Med. Chem. (1984) 27, 212-6) in 320 ml of ethanol (yield=90.6%).

I.R. (film): ν (N—OH)=3220 cm⁻¹; (C=O)=1715 cm⁻¹. N.M.R. (CDCl₃): δ=1.25 (3H,t, J=7.1 Hz); 1.1-3.4 (12H,m, 1H exchangeable with CF₃COOD); 3.6 (2H,s); 4.15 (2H,q, J=7.1 Hz); 7.1 (4H,m).

b) Ethyl 4-[(2-aminocyclohexyl)methyl]benzeneacetate (cis+trans)

Obtained by operating as in example 1b from 15.5 g (56.7 mmoles) of ethyl 4-[(2-hydroxyiminocyclohexyl)methyl]benzeneacetate in ethanol saturated with NH₃. After treatment, 6.1 g (yield=39.1%) of a yellow-green oil is isolated which is used without any other purification.

I.R. (film): ν (NH₂)=3360 cm⁻¹;(C=O)=1720 cm⁻¹. N.M.R. (CDCl₃): δ=1.25 (3H,t, J=7.1 Hz); 0.75-2.1 (11H,m, 2H exchangeable with D₂O); 2.1-2.75 (2H,m); 2.8-3.4 (1H,m); 3.6 (2H,s); 4.15 (2H,q, J=7.1 Hz); 7.1 (4H,s).

c) Ethyl 4-[[2-[[(4-chlorophenyl)sulfonyl]amino]cycohexyl]methyl]benzeneacetate (cis+trans)

Obtained by operating as in example 1c from 6.1 g (22 mmoles) of ethyl 4-[(2-aminocyclohexyl)methyl]benzeneacetate, 2.7 g (26.5 mmoles) of triethylamine in 150 ml of dichloromethane and 4.6 g (22 mmoles) of 4-chlorobenzenesulfonyl chloride in 50 ml of ether. The colorless oil obtained (yield=quantitative) is used without any other purification.

I.R. (film): ν (NH)=3280 cm⁻¹; (C=O)=1710 cm⁻¹; (SO₂)=1320 cm⁻¹; (SO₂)=1150 cm⁻¹. N.M.R. (CDCl₃): δ=1.25 (3H,t, J=6.75 Hz); 0.6-2.75 (11H,m): 2.75-3.3 (1H,m); 3.55 (2H,s); 4.1 (2H,q, J=6.75 Hz); 4.5-5.3 (1H,m, exchangeable with CF₃COOD); 6.8-7.25 (4H,m); 7.4 (2H,m); 7.8 (2H,m).

d) Trans-4-[[2-[[(4-chlorophenyl)sulfonyl]amino]cyclohexyl]methyl]benzeneacetic acid Obtained by operating as in example 1d from 9.9 g (22 mmoles) of ethyl 4-[[2-[[(4-chlorophenyl)sulfonyl]amino]cyclohexyl]methyl]benzeneacetate, 2.5 g (44 mmoles) of KOH pellets in 212 ml of an ethanol-water mixture (1:1). After 5 recrystallizations in isopropanol, 0.9 g (yield=9.7%) of a white solid is isolated. M.P.=166°-8° C.

| Percentage analysis: C₂₁H₂₄ClNO₄S (MW = 421.94) | | | | | |
|---|---|---|---|---|---|
| | C % | H % | Cl % | N % | S % |
| Calculated | 59.78 | 5.73 | 8.40 | 3.32 | 7.60 |
| Found | 59.71 | 5.56 | 8.07 | 3.31 | 7.31 |

I.R. (KBr): ν (NH)=3270 cm⁻¹; (C=O)=1690 cm⁻¹; (SO₂)=1310 cm⁻¹; (SO₂)=1140 cm⁻¹. N.M.R. (DMSO d₆): δ=0.65-2.2 (10H,m); 2.6-3.4 (3H,m, 1H exchangeable with CF₃COOD); 3.5 (2H,s); 6.8-7.3 (4H,m); 7.5-8.0 (4H,m); 12.0 (1H,s wide, exchangeable with CF₃COOD). H.P.L.C. (ODS-2): t_R=15.6. Before recrystallization t_R=12.7; 15.6; these two peaks of equal intensity correspond to the cis and trans isomers.

EXAMPLE 12

4-[1-[[[(4-Chlorophenyl)sulfonyl]amino]methyl]cyclopropyl]benzeneacetic acid a) 1-(4-Acetylphenyl)cyclopropanecarbonitrile A solution of 5 g (31.4 mmoles) of 4-acetylbenzeneacetonitrile (prepared according to Rorig K., J. Am. Chem. Soc. (1953) 75, 5381-3) in 10 ml of DMSO, is poured dropwise at room temperature in a suspension of 3.4 g (about 78.5 mmoles) of sodium hydride (at 55-60 % in mineral oil) in 60 ml of DMSO under a flow of nitrogen. After stirring 45 minutes at room temperature, 8.85 g (47.1 mmoles) of 1,2-dibromoethane dissolved in 10 ml of DMSO are added dropwise, while maintaining the temperature lower than 50° C. by means of a bath of icy water. After stirring 16 hours at room temperature the reaction mixture is poured in 300 ml of ice-water. The precipitate formed is filtered, washed with water and dried under vacuum, before being purified by recrystallization in a mixture of ethyl acetate and hexane to give 3.7 g (yield=64.0%) of a violet grey solid. M.P.=74° C.

I.R. (KBr): $\nu$ (C≡N)=2210 cm$^{-1}$; (C=O)=1660 cm$^{-1}$. N.M.R. (CDCl$_3$): $\delta$=1.3-1.65 (2H,m); 1.75-2.0 (2H,m); 2.6 (3H,s); 7.15-7.5 (2H,m); 7.75-8.1 (2H,m).

b) Methyl 4-(1-cyanocyclopropyl)benzeneacetate

To a mixture of 3.7 g (20 mmoles) of the product prepared in example 12a, 6.5 ml (160 mmoles) of methanol and 35 ml of dichloromethane, under a flow of nitrogen, 9.8 ml (80 mmoles) of boron trifluoride etherate are added dropwise at room temperature, followed by 9.75 g (22 mmoles) of lead tetraacetate in suspension in 55 ml of benzene. After having stirred the reaction mixture 17 hours at room temperature, it is poured on 150 ml of ice-water. The extraction is made with dichloromethane. The organic phase is thereafter washed with a solution which is saturated with NaHCO$_3$, then with water until neutrality, before being dried over Na$_2$SO$_4$. After concentration in vacuum, there is obtained 3.85 g (yield=89.5%) of an orange colored fluid oil used without any other purification.

I.R. (film): $\nu$ (C≡N)=2010 cm$^{-1}$; (C=O)=1725 cm$^{-1}$. N.M.R. (CDCl$_3$): $\delta$=1.2-1.55 (2H,m); 1.55-1.9 (2H,m); 3.6 (2H,s); 3.65 (3H,s); 7.2 (4H,s).

c) Methyl 4-[1-(aminomethyl)cyclopropyl]benzeneacetate

A mixture of 2.75 g (12.8 mmoles) of the compound prepared in example 12b, 8.4 ml of liquid ammonia, 80 ml of methanol and 1 g of Raney nickel washed with the methanol is treated at a pressure of 90 atmospheres of hydrogen, while stirring and at room temperature. After 1.5 hour, hydrogenation stops. After filtration and rinsing of the catalyst, the filtrate is concentrated under reduced pressure to give 2.8 g (yield=quantitative) of a yellow-green oil which is used without any other purification.

I.R. (film): $\nu$ (NH$_2$)=3300 cm$^{-1}$; (C=O)=1740 cm$^{-1}$. N.M.R. (CDCl$_3$): $\delta$=0.5-1.4 (4H,m); 1.5 (2H,s, exchangeable with CF$_3$COOD); 1.9 (2H,s); 3.5 (2H,s); 3.6 (3H,s); 6.9-7.55 (4H,m).

d) Methyl 4-[1-[[[(4-chlorophenyl)sulfonyl]amino]methyl]cyclopropyl]benzeneacetate Obtained by operating as in example 1c from 2.9 g (13.2 mmoles) of the compound prepared in example 12c, 2.2 ml (15.8 mmoles) of triethylamine in 70 ml of dichloromethane and 2.8 g (13.2 mmoles) of 4-chlorobenzenesulfonyl chloride in 7.5 ml of ether. The reaction mixture is stirred 2.5 days at room temperature. The product is purified by flash chromatography on a column of silica with a mixture of hexane-ethyl acetate 4/1 then 3/1, followed by recrystallization in a hexane-ethyl acetate mixture, to give 1.6 g (yield=30.8%) of a beige solid. M.P.=88°-89.5° C.

I.R. (KBr): $\nu$ (NH)=3280 cm$^{-1}$; (C=O)=1720 cm$^{-1}$; (SO$_2$)=1330 cm$^{-1}$; (SO$_2$)=1150 cm$^{-1}$. N.M.R. (CDCl$_3$): $\delta$=0.8 (4H,s); 3.1 (2H,d, J=6 Hz, is converted into singulet with CF$_3$COOD); 3.55 (2H,s); 3.7 (3H,s); 4.7 (1H,t, J=6 Hz, exchangeable with CF$_3$COOD); 7.05 (4H,s); 7.2-7.75 (4H,m).

e) 4-[1-[[[(4-Chlorophenyl)sulfonyl]amino]methyl]cyclopropyl]benzeneacetic acid

A mixture of 1.6 g (4 mmoles) of the compound prepared in example 12d, 20 ml of methanol, 0.5 g (8.9 mmoles) of KOH pellets and 6.7 ml water is stirred for 2 hours at 40° C. After concentration to dryness under reduced pressure, the residue is captured with 40 ml of water, washed with ethyl acetate and acidified with HCl 5N to give a beige precipitate which is captured with ethyl acetate. This organic phase is washed with H$_2$O then extracted with a saturated solution of NaHCO$_3$. The aqueous phase obtained is acidified with HCl 5N to give an off-white precipitate which is filtered, washed with water and dried one night at 50° C. After two recrystallizations in a hexane-ethyl acetate mixture, 0.55 g (yield=36.7%) of a white solid is obtained. M.P.=132°-3° C.

| Percentage analysis: C$_{18}$H$_{18}$ClNO$_4$S (MW = 379.858) | | | | | |
|---|---|---|---|---|---|
| | C % | H % | Cl % | N % | S % |
| Calculated | 56.92 | 4.78 | 9.33 | 3.69 | 8.44 |
| Found | 56.64 | 4.73 | 9.45 | 3.55 | 8.37 |

I.R. (KBr): $\nu$ (NH)=3250 cm$^{-1}$; (C=O)=1680 cm$^{-1}$; (SO$_2$)=1305 cm$^{-1}$; (SO$_2$)=1150 cm$^{-1}$. N.M.R. (acetone d$_6$): $\delta$=0.6-1.0 (4H,m); 3.15 (2H,d, J=6 Hz, is converted into singulet with CF$_3$COOD); 3.6 (2H,s); 6.6 (1H,t, J=6 Hz, exchangeable with CF$_3$COOD); 7.2 (4H,s); 7.4-7.6 (2H,m); 7.6-7.9 (2H,m); 10.2-10.9 (1H,s wide, exchangeable with CF$_3$COOD).

EXAMPLE 13

4-[1[[[(4-Chlorophenyl)sulfonyl]amino]methyl]cyclobutyl]benzeneacetic acid a) 1-Phenylcyclobutanemethanamine A commercial suspension of LiAlH$_4$ at 13% in a toluene-THF mixture, under nitrogen (0.595 mole; 175 ml), diluted with 270 ml of THF is maintained at 0° C. A mixture of 90 g (0.572 mole) of 1-phenylcyclobutanecarbonitrile and 800 ml of THF is added dropwise during 20 minutes. After the addition, the temperature is slowly allowed to rise before heating to reflux during 1 hour. After cooling at about 5° C., 150 ml water, 150 ml 10% NaOH and again 560 ml water are poured dropwise with care. The mixture is extracted with ethyl acetate after having saturated the aqueous phase with NaCl. The organic phase is extracted with a N HCl solution. This aqueous phase is made basic by means of 30% NaOH and is extracted with dichloromethane, which, after washing with water, drying over Na$_2$SO$_4$ and concentration gives a reddish liquid which is purified by distillation. There is obtained 68.65 g (yield=81.3%) of a colorless liquid. b.p.$_{.6}$=84°-92° C.

I.R. (film): $\nu$ (NH$_2$)=3350 cm$^{-1}$. N.M.R. (CDCl$_3$): $\delta$=0.9 (2H,s, exchangeable with CF$_3$COOD); 1.65-2.5 (6H,m); 2.9 (2H,s); 6.8-7.7 (5H,m).

b) 4-Chloro-N-[[1-(phenyl)cyclobutyl]methyl]benzenesulfonamide

Obtained by proceeding as in example 1c from 75 g (465 mmoles) of 1-phenylcyclobutanemethanamine prepared as in example 13a, 77.8 ml (558 mmoles) of triethylamine in 2600 ml of dichloromethane and 98.2 g (465 mmoles) of 4-chlorobenzenesulfonyl chloride in 260 ml ether. After stirring during 62 hours and the usual treatment there is obtained 154.4 g (yield=98.8%) of a creamy solid used without any other purification. M.P.=107°-8° C.

I.R. (KBr): $\nu$ (NH)=3260 cm$^{-1}$; (SO$_2$)=1325 cm$^{-1}$; (SO$_2$)=1165 cm$^{-1}$. N.M.R. (CDCl$_3$): $\delta$=1.75-2.5 (6H,m); 3.2 (2H,d, J=6.75 Hz, is converted into singulet with CF$_3$COOD); 4.15 (1H,t, J=6.75 Hz, exchangeable with CF$_3$COOD); 6.65-7.7 (9H,m).

c) N-[[1-(4-Acetylphenyl)cyclobutyl]methyl]-4-chlorobenzenesulfonamide

To a mixture under nitrogen, of 90 g (268 moles) of the compound prepared in example 13b, 52.6 ml (697 mmoles) of acetyl chloride in 1300 ml of dichloromethane, 188 g (1407 mmoles) of aluminum chloride are added by portions during 5 minutes while maintaining the temperature at −5° C. Thereafter, the mixture is stirred during 4 hours at 5° C. followed by 2 hours at 20° C. The reaction mixture is then poured over 1.5 kg of ice containing 250 ml concentrated hydrochloric acid. The mixture is extracted with dichloromethane (2×500 ml) which is thereafter washed to neutrality with H$_2$O and which is dried over Na$_2$SO$_4$. After concentration under reduced pressure, the solid residue obtained is recrystallized twice in ethyl acetate to give 32.3 g (yield =31.9%) of beige needles. M.P.=142°-3° C.

I.R. (KBr): $\nu$ (NH)=3140 cm$^{-1}$; (C=O)=1655 cm$^{-1}$; (SO$_2$)=1330 cm$^{-1}$; (SO$_2$)=1155 cm$^{-1}$. N.M.R. (CDCl$_3$): $\delta$=1.5-2.65 (6H,m); 2.5 (3H,s); 3.2 (2H, d, J=6.75 Hz, is converted into singulet with CF$_3$COOD); 4.55 (1H,t, J=6.75 Hz, exchangeable with CF$_3$COOD); 6.8-7.85 (8H,m).

d) Methyl 4-[1-[[(4-chlorophenyl)sulfonyl]amino]methyl]cyclobutyl]benzeneacetate Obtained by operating as in example 5e from 5 g (13.2 mmoles) of the compound prepared in example 13c, 5 ml of methanol in 25 ml dichloromethane, 6.5 ml boron trifluoride etherate and 6.2 g of lead tetraacetate in 35 ml of benzene. The product obtained, 4.05 g (yield=75.0%), after recrystallization in a hexane-ethyl acetate mixture is an off-white solid. M.P.=88°-90° C.

I.R. (KBr): $\nu$ (NH)=3250 cm$^{-1}$; (C=O)=1720 cm$^{-1}$; (SO$_2$)=1325 cm$^{-1}$; (SO$_2$)=1160 cm$^{-1}$. N.M.R. ((CDCl$_3$): $\delta$=1.75-2.6 (6H,m); 3.2 (2H,d, J=6.75 Hz, is converted into singulet with CF$_3$COOD); 3.6 (2H,s); 3.7 (3H,s); 4.2 (1H,t, J=6.75 Hz, exchangeable with CF$_3$COOD); 6.8-7.05 (2H,m); 7.05-7.25 (2H,m); 7.25-7.5 (2H,m); 7.5-7.8 (2H,m).

e) 4-[1-[[[(4-Chlorophenyl)sulfonyl]amino]methyl]cyclobutyl]benzeneacetic acid

Obtained by operating as in example 12e from 4 (9.8 mmoles) of the ester prepared in example 13d, 50 ml of ethanol, 1.1 g (19.6 mmoles) of KOH and 16.5 ml water. After extracting, the product is purified by flash chromatography on a column of silica (eluant CH$_2$Cl$_2$-methanol 95/5), followed by recrystallization in an ethyl acetate-cyclohexane mixture. There is obtained 1.2 g (yield=31.1%) of a white solid. M.P.=138°-9° C.

Percentage analysis: C$_{19}$H$_{20}$ClNO$_4$S (MW = 393.88)

|  | C % | H % | Cl % | N % | S % |
|---|---|---|---|---|---|
| Calculated | 57.94 | 5.12 | 9.00 | 3.56 | 8.14 |
| Found | 57.94 | 5.31 | 9.05 | 3.62 | 8.17 |

I.R. (KBr): $\nu$ (NH)=3250 cm$^{-1}$; (C=O)=1680 cm$^{-1}$; (SO$_2$)=1330 cm$^{-1}$; (SO$_2$)=1160 cm$^{-1}$. N.M.R. (CDCl$_3$): $\delta$=1.6-2.7 (6H,m); 3.2 (2H,d, J=6.75 Hz, is converted into singulet with CF$_3$COOD); 3.6 (2H,s); 4.3 (1H,t, J=6.75 Hz, exchangeable with CF$_3$COOD); 6.8-7.1 (2H,m); 7.1-7.3 (2H,m); 7.3-7.5 (2H,m); 7.5-7.75 (2H,m); 9.3-10.15 (1H,s wide, exchangeable with CF$_3$COOD).

EXAMPLE 14

4-[1-[[[(4-Chlorophenyl)sulfonyl]amino]methyl]cyclopentyl]benzeneacetic acid a) 4-Chloro-N-[[1-(phenyl)cyclopentyl]methyl]benzenesulfonamide Obtained by proceeding as in example 1c from 40.2 g (229 mmoles) of 1-phenylcyclopentanemethanamine, 38.3 ml (275 mmoles) of triethylamine in 1300 ml of dichloromethane and 49.3 g (233 mmoles) of 4-chlorobenzenesulfonyl chloride in 130 ml ether, under an inert atmosphere. After purification by chromatography on a column of silica with a hexane-ethyl acetate mixture 9/1 there is obtained 74 g (yield=92.3%) of a creamy solid, in the form of needles. M.P.=88°-91° C.

I.R. (KBr): $\nu$ (NH)=3250 cm$^{-1}$; (SO$_2$)=1340 cm$^{-1}$; (SO$_2$)=1170 cm$^{-1}$. N.M.R. (CDCl$_3$): $\delta$=1.5-2.4 (8H,m); 3.0 (2H,d, J=6.4 Hz, is converted into singulet with CF$_3$COOD); 4.2 (1H,t, J=6.4 Hz, exchangeable with CF$_3$COOD); 6.7-8.0 (9H,m).

b) N-[[1-(4-Acetylphenyl)cyclopentyl]methyl]-4-chlorobenzenesulfonamide

Obtained by operating as in example 13c from 30 g (85.7 mmoles) of the compound obtained in example 14a, 16.8 ml (222.8 mmoles) of acetyl chloride in 500 ml of dichloromethane, and 60 g (450 mmoles) of aluminum chloride, under an inert atmosphere. After purification by flash chromatography on a column of silica with hexane-ethyl acetate mixtures 3/1 to ¼, 12.9 g (yield=38.4%) of a white solid are obtained. M.P.=135°-6.5° C.

I.R. (KBr): $\nu$ (NH)=3190 cm$^{-1}$; (C=O)=1655 cm$^{-1}$; (SO$_2$)=1330 cm$^{-1}$; (SO$_2$)=1150 cm$^{-1}$. N.M.R. (CDCl$_3$): $\delta$=1.5-2.25 (8H,m); 2.55 (3H,s); 3.0 (2H,d, J=6.75 Hz, is converted into singulet with CF$_3$COOD); 4.4 (1H,t, J=6.75 Hz, exchangeable with CF$_3$COOD); 6.9-8.35 (8H,m).

c) 4-Chloro-N-[[1-[4-[2-(morpholin-4-yl)-2-thioxoethyl]phenyl]cyclopentyl]methyl]benzenesulfonamide A mixture of 7 g (17.9 mmoles) of the compound prepared in example 14b, 1 g (31.2 mmoles) of sulfur and 15 ml of morpholine is refluxed during 16 hours. The reaction mixture is then poured over 100 g of ice. The mixture is extracted with ethyl acetate (3×50 ml) after saturation of the aqueous phase with NaCl. The organic phase is washed with a N HCl solution (2×50 ml) then with water saturated with NaCl until neutrality before being dried over Na$_2$SO$_4$ and concentrated under reduced pressure. After purification of the residue obtained by flash chromatography on a column of silica in a hexane-ethyl acetate mixture 2/1, then recrystallization in a hexane-ethyl acetate mixture, 2.95 g (yield=33.5%) of a beige solid is obtained. M.P.=124°-5° C.

I.R. (KBr): $\nu$ (NH)=3260 cm$^{-1}$; (SO$_2$)=1335 cm$^{-1}$; (SO$_2$)=1160 cm$^{-1}$. N.M.R. (CDCl$_3$): $\delta$=1.3-2.1 (8H,m); 2.95 (2H,d, J=6.75 Hz, is converted into singulet with CF$_3$COOD); 3.3-4.5 (9H,m, 1H exchangeable with CF$_3$COOD); 4.3 (2H,s); 6.85-7.85 (8H,m).

d) 4-[1-[[[(4-Chlorophenyl)sulfonyl]amino]methyl]cyclopentyl]benzeneacetic acid

A mixture of 2.9 g (5.9 mmoles) of the compound prepared in example 14c, 1.5 g (37.5 mmoles) of sodium hydroxide in pellets and 37.5 ml water is refluxed during 15h. After cooling, the reaction mixture which is diluted with about 65 ml of ice-water, acidified with 5N HCl at pH 1 and saturated with NaCl, is extracted with ethyl acetate (3×100 ml). The organic phase washed with water saturated with NaCl until neutrality is dried over $Na_2SO_4$ and concentrated under reduced pressure. The residue obtained is purified by flash chromatography on a column of silica with a mixture of dichloromethane-methanol 97/3, then by recrystallization in cyclohexane in the presence of charcoal, to give 0.5 g (yield=20.8%) of a white solid. M.P.=145°–6.5° C.

| Percentage analysis: $C_{20}H_{22}ClNO_4S$ (MW = 407.912) | | | | | |
|---|---|---|---|---|---|
| | C % | H % | Cl % | N % | S % |
| Calculated | 58.89 | 5.44 | 8.69 | 3.43 | 7.86 |
| Found | 58.45 | 5.58 | 8.84 | 3.41 | 8.07 |

I.R. (KBr): $\nu$ (NH)=3280 cm$^{-1}$; (C=O)=1695 cm$^{-1}$; (SO$_2$)=1320 cm$^{-1}$; (SO$_2$)=1150 cm$^{-1}$. N.M.R. (acetone d$_6$): $\delta$=1.3–2.25 (8H,m); 3.05 (2H,d, J=6.75 Hz, converted into singulet with CF$_3$COOD); 3.5 (2H,s) 6.1 (1H,t, J=6.75 Hz, exchangeable with CF$_3$COOD); 7.15 (4H,s); 7.3–7.9 (4H,m).

EXAMPLE 15

4-[[1-[[[(Phenyl)sulfonyl]amino]methyl]cyclopentyl]methyl]benzeneacetic acid a) 1-[(Phenyl)methyl]cyclopentanemethanamine To a suspension of 68.8 g (1.81 mole) of LiAlH$_4$ in 1350 ml anhydrous ether, under an atmosphere of nitrogen, there are poured dropwise during 1.5 hour, while keeping the temperature of the reaction mixture between 10° and 20° C., 279.9 g (1.51 mole) of 1-[(phenyl)methyl]cyclopentanecarbonitrile (prepared according to Campaigne E. and Forsh R. A., J. Org. Chem. (1978) 43, 1044–50). After stirring at room temperature during 18 hours, the excess of hydride is destroyed by adding 344 ml water. The organic phase is dried over Na$_2$SO$_4$ and filtered. The filtrate which is concentrated under reduced pressure is distilled to give 273.9 g (yield=95.8%) of a colorless liquid. b.p.$_2$=122° C.

| Percentage analysis: $C_{13}H_{19}N$ (MW = 189.3) | | | |
|---|---|---|---|
| | C % | H % | N % |
| Calculated | 82.48 | 10.12 | 7.40 |
| Found | 82.23 | 9.98 | 7.39 |

I.R. (film): $\nu$ (NH$_2$)=3370 cm$^{-1}$. N.M.R (CCl$_4$): $\delta$=0.75 (2H,s wide, exchangeable with D$_2$O); 1.0–2.0 (8H,m); 2.4 (2H,s); 2.6 (2H,s); 7.05 (5H,s).

b) N-[[1-[(Phenyl)methyl]cyclopentyl]methyl]benzenesulfonamide

Obtained as in example 1c, from 17.9 g (94.5 mmoles) of the amine prepared in example 15a, 11.5 g (113 mmoles) of triethylamine in 360 ml of dichloromethane and 16.7 g (94.5 mmoles) of benzenesulfonyl chloride in 50 ml ether. After stirring 16 hours at room temperature and extraction, there is obtained a residue which is grinded in hexane to give 28.7 g (yield=92.2%) of a white solid which is used without any other purification. M.P.=105°–6° C.

I.R. (KBr): $\nu$ (NH)=3260 cm$^{-1}$; (SO$_2$)=1315 cm$^{-1}$; (SO)=1150 cm$^{-1}$. N.M.R. (CDCl$_3$): $\delta$=1.0–2.0 (8H,m); 2.6 (2H,s); 2.7 (2H,d, J=6.75 Hz, is converted into singulet with CF$_3$COOD); 5.1 (1H,t, J=6.75 Hz, exchangeable with CF$_3$COOD); 6.7–7.3 (5H,m); 7.3–7.7 (3H,m); 7.7–8.0 (2H,m).

c) N-[[1-[(4-Acetylphenyl)methyl]cyclopentyl]methyl]benzenesulfonamide

A solution of 28.7 g (87.1 mmoles) of the compound prepared in example 15b and 500 ml of dichloromethane is maintained between −20° C. and −10° C. 15 g (191 mmoles) of acetyl chloride are added, then by portions 46.4 g (348 mmoles) of aluminum chloride. After stirring 4 hours at the same temperature, the mixture is poured over about 1.5 l of ice-water-HCl. After extraction with dichloromethane, washing with water until neutrality, drying over Na$_2$SO$_4$, concentration under reduced pressure and grinding of the residue obtained, in hexane, 28.6 g (yield=88.3%) of a white solid is obtained, which is used without any other purification. M.P.=88°–9° C.

I.R. (KBr): $\nu$ (NH)=3250 cm$^{-1}$; (C=O)=1660 cm$^{-1}$; (SO$_2$)=1310 cm$^{-1}$; (SO$_2$)=1145 cm$^{-1}$. N.M.R. (CDCl$_3$): $\delta$=1.0–2.0 (8H,m); 2.45–2.9 (7H,m); 4.55–5.2 (1H,m, exchangeable with CF$_3$COOD); 6.75–8.0 (9H,m).

d) Methyl 4-[[1-[[[(phenyl)sulfonyl]amino]methyl]cyclopentyl]methyl]benzeneacetate Obtained by operating as in example 5e from 28.6 g (76.9 mmoles) of the compound prepared in example 15c, 35 ml of methanol, 43.6 g (308 mmoles) of boron trifluoride etherate in 175 ml of dichloromethane and 35.8 g (80.7 mmoles) of lead tetraacetate in 205 ml of benzene. After three recrystallizations in a hexane-ethyl acetate mixture, there is obtained 6.3 g (yield=20.4%) of a white solid. M.P. 129°–30° C.

I.R. (KBr): $\nu$ (NH)=3240 cm$^{-1}$; (C=O)=1700 cm$^{-1}$; (SO$_2$)=1340 cm$^{-1}$; (SO$_2$)=1150 cm$^{-1}$. N.M.R. (CDCl$_3$): $\delta$=0.8–2.1 (8H,m); 2.6 (2H,s); 2.7 (2H,d, J=6.75 Hz, is converted into singulet with CF$_3$COOD); 3.55 (2H,s); 3.65 (3H,s); 4.9 (1H,t, J=6.75 Hz, exchangeable with CF$_3$COOD); 6.7–8.0 (9H,m).

e) 4-[[1-[[[(Phenyl)sulfonyl]amino]methyl]cyclopentyl]methyl]benzeneacetic acid

Obtained by operating as in example 5f from 6.3 g (15.7 mmoles) of the ester prepared in example 15d, 1.8 g (31.4 mmoles) of KOH flakes, 63 ml ethanol and 63 ml water. After two recrystallizations in a hexane-ethyl acetate mixture, there is obtained 4.2 g (yield=65.7%) of a white solid. M.P.=154°–6° C.

| Percentage analysis: $C_{21}H_{25}NO_4S$ (MW = 387.494) | | | | |
|---|---|---|---|---|
| | C % | H % | N % | S % |
| Calculated | 65.09 | 6.50 | 3.61 | 8.27 |
| Found | 64.92 | 6.57 | 3.62 | 8.05 |

I.R. (film): $\nu$ (NH)=3260 cm$^{-1}$; (C=O)=1690 cm$^{-1}$; (SO$_2$)=1315 cm$^{-1}$; (SO$_2$)=1155 cm$^{-1}$. N.M.R. (DMSO d$_6$): $\delta$=0.8–1.75 (8H,m); 2.4–2.85 (5H,m, 1H exchangeable with CF$_3$COOD); 3.45 (2H,s); 7.0 (4H,s); 7.4–8.0 (5H,m); 12.1 (1H,s, exchangeable with CF$_3$COOD).

EXAMPLE 16

4-[[1-[[[(4-Fluorophenyl)sulfonyl]amino]methyl]cyclopentyl]methyl]benzeneacetic acid a) 4-Fluoro-N-[[1-[(phenyl)methyl]cyclopentyl]methyl]benzenesulfonamide Obtained by operating as in example 1c, from 9.4 g (48.3 mmoles) of 1-[(phenyl)methyl]cyclopentanemethanamine prepared as in example 15a, 8.1 ml (57.9 mmoles) of triethylamine in 200 ml of dichloromethane and 9.4 g (48.3 mmoles) of 4-fluorobenzenesulfonyl chloride in 60 ml of dichloromethane. After stirring 3 days at room temperature and extraction, there is obtained a residue which is grinded in hexane to give 15.2 g (yield=90.5%) of a white solid which is used without any other purification. M.P.=115°-7° C.

I.R. (KBr): ν (NH)=3260 cm$^{-1}$; (SO$_2$)=1320 cm$^{-1}$; (SO$_2$)=1150 cm$^{-1}$. N.M.R. (CDCl$_3$): δ=1.0-1.85 (8H,m); 2.6 (2H,s); 2.7 (2H,d, is converted into singulet with CF$_3$COOD); 5.6 (1H,t, exchangeable with CF$_3$COOD); 6.75-8.0 (9H,m).

b) N-[[1-[(4-Acetylphenyl)methyl]cyclopentyl]methyl]-4-fluorobenzenesulfonamide

To a mixture of 15.2 g (43.7 mmoles) of the compound prepared in example 16a, 4.4 g (56.8 mmoles) of acetyl chloride and 290 ml of dichloromethane, maintained at 0° C., 19.2 g (144 mmoles) of aluminum chloride are added by portions. After having stirred 3 hours at 0° C., the mixture is poured over a ice concentrated HCl mixture. The mixture is extracted with dichloromethane, and is thereafter washed with water until neutrality, dried over Na$_2$SO$_4$, then concentrated under reduced pressure to give an oil which, after grinding in hexane, gives 9.7 g (yield=57.0%) of a off-white solid used without any other purification. M.P.=79°-82° C.

I.R. (KBr): ν (NH)=3260 cm$^{-1}$; (C=O)=1670 cm$^{-1}$; (SO$_2$)=1315 cm$^{-1}$; (SO$_2$)=1160 cm$^{-1}$. N.M.R. (CDCl$_3$): δ=1.0-2.0 (8H,m); 2.55 (3H,s); 2.7 (2H,d, J=6.75 Hz, is converted into singulet with CF$_3$COOD); 2.7 (2H,s); 5.1 (1H,t, J=6.75 Hz, exchangeable with CF$_3$COOD); 6.85-7.4 (4H,m); 7.6-8.0 (4H,m).

c) Methyl 4-[[1-[[[(4-fluorophenyl)sulfonyl]amino]methyl]cyclopentyl]methyl]benzeneacetate Obtained by operating as in example 5e from 9.7 g (24.9 mmoles) of the compound prepared in example 16b, 11.3 ml of methanol in 56 ml of dichloromethane, 14.1 g (99.6 mmoles) of boron trifluoride etherate and 13.2 g (29.8 mmoles) of lead tetraacetate in 60 ml of benzene. After recrystallization in ethyl acetate, there is obtained 6.1 g (yield=58.4%) of a white solid. M.P.=138°-40° C.

I.R. (KBr): ν (NH)=3240 cm$^{-1}$; (C=O)=1700 cm$^{-1}$; (SO$_2$)=1340 cm$^{-1}$; (SO$_2$)=1150 cm$^{-1}$. N.M.R. (CDCl$_3$): δ=1.0-1.9 (8H,m); 2.6 (2H,s); 2.7 (2H,d, J=6.75 Hz, is converted into singulet with CF$_3$COOD); 3.55 (2H,s); 3.7 (3H,s); 4.5 (1H,t, J=6.75 Hz, exchangeable with CF$_3$COOD); 6.95-7.35 (6H,m); 7.65-8.0 (2H,m).

d) 4-[[1-[[[(4-Fluorophenyl)sulfonyl]amino]methyl]cyclopentyl]methyl]benzeneacetic acid Obtained by operating as in example 5f from 6.1 g (14.5 mmoles) of the compound prepared in example 16c in 61 ml ethanol and 1.6 g (29 mmoles) of KOH pellets in 61 ml water. After two recrystallizations in a hexane-ethyl acetate mixture, there is obtained 1.9 g (yield=32.0%) of a white solid. M.P.=151°-4° C.

| Percentage analysis: C$_{21}$H$_{24}$FNO$_4$S (MW = 405.484) | | | | | |
|---|---|---|---|---|---|
| | C % | H % | F % | N % | S % |
| Calculated | 62.20 | 5.97 | 4.69 | 3.45 | 7.91 |
| Found | 61.94 | 5.96 | 4.55 | 3.44 | 7.71 |

I.R. (KBr): ν (NH)=3260 cm$^{-1}$; (C=O)=1685 cm$^{-1}$; (SO$_2$)=1310 cm$^{-1}$; (SO$_2$)=1140 cm$^{-1}$. N.M.R. (acetone d$_6$): δ=1.1-1.8 (8H,m); 2.65 (2H,s); 2.75 (2H,d, J=6.75 Hz, is converted into singulet with CF$_3$COOD); 3.6 (2H,s); 6.3 (1H,t, J=6.75 Hz, exchangeable with CF$_3$COOD); 7.15 (4H,s); 7.25-7.55 (2H,m); 7.7-8.15 (2H,m); 10.55 (1H,s wide, exchangeable with CF$_3$COOD).

EXAMPLE 17

N-[[1-[(4-Acetylphenyl)methyl]cyclopentyl]methyl]-4-chlorobenzenesulfonamide a) 4-Chloro-N-[[1-[(phenyl)methyl]cyclopentyl]methyl]-benzenesulfonamide To a solution consisting of 268.2 g (1.416 mole) of the amine prepared in example 15a, 237 ml (1.700 mole) of triethylamine and 2500 ml of dry dichloromethane, maintained at 0° C., 298.8 g (1.416 mole) of 4-chlorobenzenesulfonyl chloride are added by portions. The reaction mixture is stirred 2.5 days at room temperature before being thrown in 2.5 l water containing 1.5 mole of HCl. The organic phase is decanted, washed with water, dried over Na$_2$SO$_4$ and concentrated under reduced pressure. After recrystallization in ethyl acetate, there is obtained 467.2 g (yield=90.7%) of a white solid. M.P.=121°-3° C.

| Percentage analysis: C$_{19}$H$_{22}$ClNO$_2$S (MW = 363.90) | | | | | |
|---|---|---|---|---|---|
| | C % | H % | Cl % | N % | S % |
| Calculated | 62.71 | 6.09 | 9.74 | 3.85 | 8.81 |
| Found | 62.54 | 6.08 | 9.72 | 3.85 | 8.94 |

I.R. (KBr): ν (NH)=3250 cm$^{-1}$; (SO$_2$)=1315 cm$^{-1}$; (SO$_2$)=1170 cm$^{-1}$. N.M.R. (CDCl$_3$): δ=1.0-1.9 (8H,m); 2.6 (2H,s); 2.7 (2H,d, J=6.75 Hz, is converted into singulet with CF$_3$COOD); 5.0 (1H,t, J=6.75 Hz, exchangeable with CF$_3$COOD); 6.8-7.3 (5H,m); 7.3-7.5 (2H,m); 7.6-7.9 (2H,m).

b) N-[[1-[(4-Acetylphenyl)methyl]cyclopentyl]methyl]-4-chlorobenzenesulfonamide

The compound obtained in example 17a (185.9 g; 511 mmoles) dissolved in 3000 ml of anhydrous 1,2-dichloroethane is maintained under stirring at −20° C. 47.2 ml (664 mmoles) of acetyl chloride are poured dropwise, then 340.7 g (2555 mmoles) of aluminum chloride by portions. The temperature is allowed to rise to −12° C. After 8 hours at this temperature, the mixture is allowed to rest 16 hours at −25° C. The reaction mixture is thereafter directly thrown over a mixture of 5000 ml water and 2000 ml concentrated HCl. After decantation of the organic phase and extraction with 4×500 ml of dichloromethane, the combined organic phases are washed with water (1000 ml) sodium hydroxide 1N (2×1000 ml) then water until neutrality. After drying over Na$_2$SO$_4$ and concentration there is obtained a brown oil which is grinded in hexane until crystallization. The rose solid obtained, is squeezed and dried (153.9 g) and is used without any other purification (yield=74.2%). M.P.=97°-102° C. A fraction which is purified by chromatography on a column of silica in dichloromethane followed by recrystallization in a hexane-ethyl acetate mixture gives a white solid. M.P.=110°-3°0C.

| Percentage analysis: C$_{21}$H$_{24}$ClNO$_3$S (MW = 405.94) | | | | | |
|---|---|---|---|---|---|
| | C % | H % | Cl % | N % | S % |
| Calculated | 62.14 | 5.96 | 8.73 | 3.45 | 7.90 |
| Found | 62.13 | 5.90 | 8.81 | 3.45 | 8.17 |

I.R. (KBr): $\nu$ (NH)=3200 cm$^{-1}$; (C=O)=1660 cm$^{-1}$; (SO$_2$)=1315 cm$^{-1}$; (SO$_2$)=1150 cm$^{-1}$. N.M.R. (CDCl$_3$): $\delta$=1.0-2.0 (8H,m); 2.6 (3H,s); 2.7 (2H,s); 2.75 (2H,d, J=6.75 Hz, is converted into singulet with CF$_3$COOD); 5.25 (1H,t, J=6.75 Hz, exchangeable with CF$_3$COOD); 6.6-8.0 (8H,m).

EXAMPLE 18

Methyl 4-[[1-[[[(4-chlorophenyl)sulfonyl]amino]methyl]cyclopentyl]methyl]benzeneacetate Obtained by operating as in example 5e from 30.8 g (75.8 mmoles) of the derivative prepared in example 17b, 34 ml of methanol in 170 ml of dichloromethane, 55.9 ml (455 mmoles) of boron trifluoride etherate and 50.4 g (114 mmoles) of lead tetraacetate in 200 ml of dichloromethane. The product is purified by recrystallization in ethyl acetate to give 21.2 g (yield=64.2%) of a white solid. M.P.=154°-6° C.

| Percentage analysis: C$_{22}$H$_{26}$ClNO$_4$S (MW = 435.97) | | | | | |
|---|---|---|---|---|---|
| | C % | H % | Cl % | N % | S % |
| Calculated | 60.61 | 6.01 | 8.15 | 3.21 | 7.35 |
| Found | 60.79 | 6.24 | 8.21 | 3.42 | 7.37 |

I.R. (KBr): $\nu$ (NH)=3230 cm$^{-1}$; (C=O)=1700 cm$^{-1}$; (SO$_2$)=1330 cm$^{-1}$; (SO$_2$)=1150 cm$^{-1}$. N.M.R. (CDCl$_3$): $\delta$=1.0-2.0 (8H,m); 2.6 (2H,s); 2.7 (2H,d, J=6.75 Hz, is converted into singulet with CF$_3$COOD); 3.55 (2H,s); 3.7 (3H,s); 4.4 (1H,t, J=6.75 Hz, exchangeable with CF$_3$COOD); 6.6-7.3 (4H,m); 7.3-8.0 (4H,m).

EXAMPLE 19

4-[[1-[[[(4-Chlorophenyl)sulfonyl]amino]methyl]cyclopentyl]methyl]benzeneacetic acid A mixture of 16.1 g (36.9 mmoles) of the compound prepared in example 18, 4.1 g (73.8 mmoles) of KOH pellets, 236 ml of methanol and 236 ml of water is refluxed for 2 hours. After removing methanol under reduced pressure, the mixture is captured with water, washed with ethyl ether, before acidification with diluted HCl. The precipitate formed is squeezed, washed with water and dried at 50° C. There is obtained 14.9 g (yield=96.1%) of a white solid. M.P.=151°-4° C.

| Percentage analysis: C$_{21}$H$_{24}$ClNO$_4$S (MW = 421.939) | | | | | |
|---|---|---|---|---|---|
| | C % | H % | Cl % | N % | S % |
| Calculated | 59.78 | 5.73 | 8.40 | 3.32 | 7.60 |
| Found | 59.85 | 5.95 | 8.72 | 3.21 | 7.96 |

I.R. (KBr): $\nu$ (NH)=3270 cm$^{-1}$; (C=O)=1690 cm$^{-1}$; (SO$_2$)=1315 cm$^{-1}$; (SO$_2$)=1155 cm$^{-1}$. N.M.R. (acetone d$_6$): $\delta$=1.0-2.0 (8H,m); 2.65 (2H,s); 2.7 (2H,d, J=6.75 Hz, is converted into singulet with CF$_3$COOD); 3.55 (2H,s); 6.3 (1H,t, J=6.75 Hz, exchangeable with CF$_3$COOD); 7.1 (4H,s); 7.4-7.7 (2H,m); 7.7-8.0 (2H,m); 9.2 (1H,s wide, exchangeable with CF$_3$COOD).

EXAMPLE 20

Sodium 4-[[1-[[[(4-chlorophenyl)sulfonyl]amino]methyl]cyclopentyl]methyl]benzeneacetate A mixture of 0.4 g (0.95 mmole) of the acid prepared in example 19 and 9.35 ml of a solution of NaOH 0.1N is heated at 50° C. for a few minutes. After returning to room temperature, then filtration, the mixture is concentrated to dryness under reduced pressure. The residue is recrystallized in a mixture of ethanol and ether to give 0.3 g (yield=71.3%) of a white solid. M.P.=218°-22° C.

| Percentage analysis: C$_{21}$H$_{23}$ClNNaO$_4$S (MW = 443.92) | | | | | | |
|---|---|---|---|---|---|---|
| | C % | H % | Cl % | N % | Na % | S % |
| Calculated | 56.82 | 5.22 | 7.99 | 3.16 | 5.18 | 7.22 |
| Found | 57.10 | 5.30 | 8.16 | 3.18 | 5.16 | 7.10 |

I.R. (KBr): $\nu$ (NH)=3060 cm$^{-1}$; (C=O)=1570 cm$^{-1}$; (SO$_2$)=1370 cm$^{-1}$; (SO$_2$)=1140 cm$^{-1}$. N.M.R. (DMSO d$_6$): $\delta$=1.1-1.75 (8H,m); 2.3-2.8 (5H,m, 1H exchangeable with CF$_3$COOD); 3.2 (2H,s); 6.75-7.25 (4H,m); 7.4-8.5 (4H,m).

EXAMPLE 21

4-[[1-[[[(4-chlorophenyl)sulfonyl]amino]methyl]cyclopentyl]methyl]benzeneacetic acid a) 4-Chloro-N-[[1-[[4-[2-(morpholin-4-yl)-2-thioxoethyl]phenyl]methyl]cyclopentyl]methyl]benzenesulfonamide A mixture of 12.4 g (30.5 mmoles) of the compound obtained in example 17b, 1.6 g (48.8 mmoles) of sulfur and 200 ml of morpholine, is refluxed 30 hours, before being thrown over a mixture of ice and water. The precipitate obtained is purified by chromatography on a column of silica with a mixture of hexane-ethyl acetate 4/1, then 2/1, before being recrystallized in a hexane-ethyl acetate mixture, to give 1.3 g (yield=8.4%) of a white solid. M.P.=141°-4° C. 2.7 g of the product is recovered from the moter liquors (global yield=25.6%).

I.R. (KBr): $\nu$ (NH)=3250 cm$^{-1}$. N.M.R. ((CDCl$_3$): $\delta$=1.0-1.75 (8H,m); 2.3-2.9 (6H,m); 3.0-3.4 (4H,m); 3.55-3.9 (4H,m); 5.1 (1H,t, J=6.75 Hz, exchangeable with CF$_3$COOD); 6.5-7.3 (4H,m); 7.35-7.9 (4H,m).

b) 4-[[1-[[[(4-Chlorophenyl)sulfonyl]amino]methyl]cyclopentyl]methyl]benzeneacetic acid A mixture consisting of 2.7 g (5.3 mmoles) of the product prepared in example 21a, 1.3 g (33 mmoles) of NaOH pellets and 33 ml of water, is refluxed 24 h. After cooling, the reaction mixture is diluted with water and washed with ether, filtrated and acidified with concentrated HCl under cold condition. The precipitate formed is washed with water, then dried under vacuum at 80° C., before being recrystallized in a hexane-ethyl acetate mixture to give 0.4 g (yield=17.9%) of a white product having all the physical, spectral and chromatographic characteristics of the compound obtained in example 19.

EXAMPLE 22

Complex of sodium trans-4-[[2-[[(4-chlorophenyl)sulfonyl]amino]cyclopentyl]methyl]benzeneacetate and β-cyclodextrine (1:1)

To a solution consisting of 0.62 g (1.45 mmole) of sodium trans-4-[[2-[[(4-chlorophenyl)sulfonyl]amino]-cyclopentyl]methyl]benzeneacetate prepared in example 2 and 60 ml of distilled water, there is added a warm mixture of 1.65 g (1.45 mmole) of β-cyclodextrine and 60 ml of distilled water. After stirring 20 hours at 20° C., the solvent is removed under reduced pressure. The residual water is withdrawn by azeotropic distillation with toluene at normal pressure. The toluene is concentrated under reduced pressure and the residue is dried 6 h under vacuum. There is obtained 2 g (yield=90.9%) of an off-white solid. M.P.=265° C. (color starting at 210° C.).

| Percentage analysis: $C_{62}H_{91}ClNNaO_{39}S + H_2O$ (MW = 1582.881) | | | | | | |
|---|---|---|---|---|---|---|
| | C % | H % | Cl % | N % | Na % | S % |
| Calculated | 47.05 | 5.92 | 2.24 | 0.88 | 1.45 | 2.03 |
| Found | 47.05 | 5.97 | 2.10 | 0.83 | 1.65 | 1.86 |

I.R. (KBr): $\nu$ (OH)=3360 cm$^{-1}$; (C=O)=1570 cm$^{-1}$; (SO$_2$)=1320 cm$^{-1}$; (SO$_2$)=1155 cm$^{-1}$. N.M.R. (DMSO$_6$): δ=0.9–2.25 (9H,m); 2.6–4.05 (48H,m, 3H exchangeable with CF$_3$COOD); 4.1–4.6 (7H,m, exchangeable with CF$_3$COOD); 4.7–5.0 (7H,m); 5.65–6.3 (14H,m, exchangeable with CF$_3$COOD); 6.7–7.1 (4H,m); 7.4–7.9 (4H,m).

EXAMPLE 23

Complex of sodium 4-[[1-[[[(4-chlorophenyl)sulfonyl]amino]methyl]cyclopentyl]methyl]benzeneacetate and β-cyclodextrine (1:1)

Obtained by operating as in example 22 from 0.5 g (1.12 mmole) of sodium 4-[[1-[[[(4-chlorophenyl)sulfonyl]amino]methyl]cyclopentyl]methyl]benzeneacetate prepared as in example 20, in 50 ml of distilled water and 1.28 g (1.12 mmole) of β-cyclodextrine dissolved in 50 ml of distilled water. There is obtained 1.5 g (yield=83%) of an off-white solid. M.P.=240°–270° C.

| Percentage analysis: $C_{63}H_{93}ClNNaO_{39}S$ + 0.75 $C_7H_8$ (toluene) (MW = 1648.013) | | | | | | |
|---|---|---|---|---|---|---|
| | C % | H % | Cl % | N % | Na % | S % |
| Calculated | 49.74 | 6.05 | 2.15 | 0.85 | 1.39 | 1.94 |
| Found | 49.50 | 6.07 | 2.25 | 1.07 | 1.30 | 2.29 |

I.R. (KBr): $\nu$ (OH)=3360 cm$^{-1}$; (C=O)=1570 cm$^{-1}$; (SO$_2$)=1320 cm$^{-1}$; (SO$_2$)=1150 cm$^{-1}$. N.M.R. (DMSO d$_6$): δ=1.0–1.6 (8H,m); 2.3 (2H,s); 2.5 (2H,s); 2.75–4.0 (44H,m); 4.2–4.6 (7H,m, exchangeable with CF$_3$COOD); 4.7–5.0 (7H,m); 5.75–6.4 (14H,m, exchangeable with CF$_3$COOD); 6.75–7.25 (5H,m, 1H exchangeable with CF$_3$COOD); 7.4–7.9 (4H,m).

EXAMPLE 24

4-[[1-[[[(4-methylphenyl)sulfonyl]amino]methyl]cyclopentyl]methyl]benzeneacetic acid a) 4-Methyl-N-[[1-[(phenyl)methyl]cyclopentyl]methyl]-benzenesulfonamide Obtained by operating as in example 1c, from 9.4 g (48.3 mmoles) of the amine prepared in the example 15a, 5.9 g (57.9 mmoles) of triethylamine in 200 ml of dichloromethane and 9.2 g (48.3 mmoles) of 4-methylbenzenesulfonyl chloride in 60 ml of dichloromethane. After stirring 16 hours at room temperature and treatment, there is obtained 16.0 g (96.4%) of a beige solid, used without other purification. M.P.=124°–6° C.

I.R. (KBr): $\nu$ (NH)=3280 cm$^{-1}$; (SO$_2$)=1315 cm$^{-1}$; (SO$_2$)=1160 cm$^{-1}$. N.M.R. (CDCl$_3$): δ=1.0–2.0 (8H,m); 2.4 (3H,s); 2.6 (2H,s); 2.7 (2H,d); 4.5 (1H,m, exchangeable with CF$_3$COOD); 6.7–7.45 (7H,m); 7.5–7.9 (2H,m).

b) N-[[1-[(4-Acetylphenyl)methyl]cyclopentyl]methyl]-4-methylbenzenesulfonamide

Obtained by operating as in example 16b, from 16.0 g (46.5 mmoles) of the compound prepared as in example 24a, 4.3 ml (60.4 mmoles) of acetyl chloride in 280 ml of dichloromethane and 20.5 g (153.7 mmoles) of aluminum chloride. After purification by chromatography on a column of silica with a hexane-ethyl acetate mixture 2/1 and 1/1, there is obtained 10.7 g (yield=59.7%) of an off-white solid. M.P.=80°–4° C.

I.R. (KBr): $\nu$ (NH)=3220 cm$^{-1}$; (C=O)=1650 cm$^{-1}$; (SO$_2$)=1310 cm$^{-1}$; (SO$_2$)=1140 cm$^{-1}$. N.M.R. (CDCl$_3$): δ=1.25–1.8 (8H,m); 2.4 (3H,s); 2.5–2.85 (7H,m, in which a doublet is converted into singulet with CF$_3$COOD); 4.9 (1H,m, exchangeable with CF$_3$COOD); 6.9–8.0 (8H,m).

c) Methyl 4-[[1-[[[(4-methylphenyl)sulfonyl]amino]methyl]cyclopentyl]methyl]benzeneacetate Obtained by operating as in example 5e from 10.7 g (27.7 mmoles) of the compound prepared in example 24b, 12 ml of methanol, 13.6 ml (111 mmoles) of boron trifluoride etherate in 60 ml of dichloromethane and 14.7 g (33.2 mmoles) of lead tetraacetate in 75 ml of benzene. After recrystallization in ethyl acetate there is obtained 2.5 g (yield=21.7%) of an off-white solid. M.P.=148°–51° C.

I.R. (KBr): $\nu$ (NH)=3250 cm$^{-1}$; (C=O)=1710 cm$^{-1}$; (SO$_2$)=1315 cm$^{-1}$; (SO$_2$)=1155 cm$^{-1}$. N.M.R. (CDCl$_3$): δ=1.0–1.9 (8H,m); 2.4 (3H,s); 2.55 (2H,s); 2.7 (2H,d, J=6.75 Hz, is converted into singulet with CF$_3$COOD); 3.5 (2H,s); 3.65 (3H,s); 4.5 (1H,t, J=6.75 Hz, exchangeable with CF$_3$COOD); 6.85–7.4 (6H,m); 7.5–7.8 (2H,m).

d) 4-[[1-[[[(4-Methylphenyl)sulfonyl]amino]methyl]cyclopentyl]methyl]benzeneacetic acid Obtained by operating as in example 5f from 2.5 g (6 mmoles) of the ester prepared in example 24c, 0.67 g (12 mmoles) of KOH pellets, 25 ml ethanol and 25 ml of water. After two recrystallizations in a hexane-ethyl acetate mixture, there is obtained 1.2 g (yield=50.0%) of an off-white solid. M.P.=164°–6° C.

| Percentage analysis: $C_{22}H_{27}NO_4S$ (MW = 401.521) | | | | |
|---|---|---|---|---|
| | C % | H % | N % | S % |
| Calculated | 65.81 | 6.78 | 3.49 | 7.98 |
| Found | 65.97 | 6.88 | 3.46 | 8.25 |

I.R. (KBr): $\nu$ (NH)=3250 cm$^{-1}$; (C=O)=1690 cm$^{-1}$; (SO$_2$)=1315 cm$^{-1}$; (SO$_2$)=1150 cm$^{-1}$. N.M.R. (DMSO d$_6$): $\delta$=1.0–1.75 (8H,m); 2.4 (3H,s); 2.4–2.8 (4H,m); 3.5 (2H,s); 7.05 (4H,s); 7.2–8.0 (5H,m, 1H exchangeable with CF$_3$COOD); 12.2 (1H,s, exchangeable with CF$_3$COOD).

EXAMPLE 25

4-[[1-[[[(4-Chlorophenyl)sulfonyl]amino]methyl]cyclopentyl]methyl]benzoic acid a) 4-(Chloromethyl)benzenemethanol A mixture of 50 g (293 mmoles) of 4-chloromethylbenzoic acid and 400 ml of tetrahydrofuran is added dropwise to a solution maintained at 15° C., of the boron hydride-dimethylsulfide complex (320 mmoles) in 410 ml of tetrahydrofuran. The mixture is refluxed for 6 hours. After cooling 400 ml water is added, and the mixture is saturated with potassium carbonate before extraction with ethyl acetate. The organic phase washed with water to neutrality is dried over Na$_2$SO$_4$, then concentrated under reduced pressure before being purified by distillation to give 35.95 g (yield=78.3%) of a pale yellow liquid, which rapidly crystallizes. M.P.=49°–51° C.; b.p.$_{0.6}$=121° C.

I.R. (KBr): $\nu$ (OH)=3340 cm$^{-1}$. N.M.R. (CDCl$_3$): $\delta$=2.25 (1H,s, exchangeable with CF$_3$COOD); 4.55 (2H,s); 4.6 (2H,s); 7.3 (4H,s).

b) 1-(Chloromethyl)-4-[(trimethylsilyloxy)methyl]benzene

To a solution of 35.95 g (230 mmoles) of the compound prepared in example 25a and 370 ml of anhydrous dichloromethane maintained at 5° C., 36.9 g (230 mmoles) of 1,1,1,3,3,3,-hexamethyldisilazane are poured dropwise, then 23.3 g (230 mmoles) of triethylamine and finally 24.6 g (230 mmoles) of trimethylsilyl chloride. The reaction mixture is maintained 21 hours at 5° C. then 7 hours at 20° C. The white precipitate formed is filtrated on fritted glass and rinsed with dichloromethane. The filtrate which is concentrated to dryness under reduced vacuum at 30° C. is captured by hexane. The new precipitate formed is filtrated on fritted glass and rinsed with hexane. The filtrate, after concentration is distilled to give 42.9 g (yield=81.5%) of a colorless liquid. b.p.$_{0.45}$=85°–8° C.

N.M.R. (CDCl$_3$): $\delta$=0.0 (9H,s); 4.4 (2H,s); 4.5 (2H,s); 7.1 (4H,s).

c) 1-[[4-[(Trimethylsilyloxy)methyl]phenyl]methyl]cyclopentanecarbonitrile

To a mixture of 13.8 g (136 mmoles) of diisopropylamine and 157 ml of tetrahydrofuran cooled to −75° C., there is poured dropwise during 40 minutes, 65.6 ml of n-butyllithium in a 1.6M solution in hexane, then 10 g (105 mmoles) of cyclopentanecarbonitrile and finally 26.4 g (115 mmoles) of the compound prepared in example 25b. The reaction mixture is thereafter stirred 2 hours at −70° C. then 16 hours at 20° C. There is then added 100 ml of water and the organic phase is decanted, and is dried over Na$_2$SO$_4$ and concentrated to dryness under vacuum. The product is purified by distillation to give 14.1 g (yield=46.8%) of a page yellow thick oil. b.p.$_{1.3}$=170° C.

I.R. (film): $\nu$ (C≡N)=2230 cm$^{-1}$. N.M.R. (CDCl$_3$): $\delta$=0.0 (9H,s); 1.3–2.25 (8H,m); 2.7 (2H,s); 4.5 (2H,s); 7.1 (4H,s).

d) 1[[4-(Hydroxymethyl)phenyl]methyl]cyclopentanecarbonitrile

To a solution of 13.2 g (45 mmoles) of the compound prepared in example 25c and 50 ml of tetrahydrofuran, there is added 53.7 ml (53 mmoles) of a 1M solution of tetrabutylammonium fluoride in tetrahydrofuran. After having stirred 15 minutes, it is poured over 800 ml water, extraction is carried out with ethyl acetate followed by drying over Na$_2$SO$_4$. The brown fluid oil obtained (yield=quantitative) is used without other purification.

I.R. (film): $\nu$ (OH)=3370 cm$^{-1}$; (C≡N)=2200 cm$^{-1}$. N.M.R. (CDCl$_3$): $\delta$=1.5–2.25 (8H,m); 2.4 (1H,s, exchangeable with D$_2$O); 2.8 (2H,s); 4.55 (2H,s); 7.2 (4H,s).

e) 4-[[1-(Aminomethyl)cyclopentyl]methyl]benzenemethanol

A mixture of 6.4 g (29.7 mmoles) of the compound prepared in example 25d and 12.6 ml ether is poured dropwise, at room temperature over 1.35 g (35.6 mmoles) of LiAlH$_4$ in suspension in 35 ml ether. The speed of addition is adjusted to keep the solvent under reflux condition. After addition, the reaction mixture is stirred 18 hours at room temperature then 5 hours under reflux. The excess hydride is destroyed with 6.75 ml of water. The mineral salts formed are filtrated over Na$_2$SO$_4$ and washed with ether. The filtrate which is concentrated under reduced pressure gives 5 g (yield=76.7%), of a yellow oil used without other purification.

I.R. (film): $\nu$ (NH$_2$)=3350 cm$^{-1}$; (OH)=3300 cm$^{-1}$. N.M.R. (CDCl$_3$): $\delta$=0.9–2.1 (8H,m); 2.3 (2H,s); 2.5 (2H,s); 2.6 (3H,s wide, exchangeable with CF$_3$COOD); 4.5 (2H,s); 6.6–7.5 (4H,m).

f) 4-Chloro-N-[[1-[[4-(hydroxymethyl)phenyl]methyl]cyclopentyl]methyl]benzenesulfonamide A mixture of 1 g (4.6 mmoles) of the compound prepared in example 25e, 0.55 g (5.5 mmoles) of triethylamine and 8 ml of dry dichloromethane is maintained at −20° C. A solution of 0.96 g (4.6 mmoles) of 4-chlorobenzenesulfonyl chloride in 4 ml ether is poured during 15 min. Stirring is carried out during 2.5 hours at a temperature between −20° and −10° C. before pouring same over 50 ml of water to which 1 ml of concentrated HCl is added. Extraction is carried out with dichloromethane, and the extract is washed until neutrality, dried over Na$_2$SO$_4$ and concentrated under reduced pressure to give a beige solid. The product is purified by chromatography on a column of silica in a dichloromethane-methanol mixture 95:5. There is obtained 0.8 g (yield=44.6%) of a white pasty solid.

I.R. (film): $\nu$ (OH)=3460 cm$^{-1}$; (NH)=3270 cm$^{-1}$; (SO$_2$)=1315 cm$^{-1}$; (SO$_2$)=1150 cm$^{-1}$. N.M.R. (CDCl$_3$): $\delta$=1.25–1.75 (8H,m); 1.9 (1H,s wide, exchangeable with CF$_3$COOD); 2.6 (2H,s); 2.7 (2H,d, J=6.75 Hz, is converted into singulet with CF$_3$COOD); 4.6 (2H,s); 4.85 (1H,t, J=6.75 Hz, exchangeable with CF$_3$COOD); 7.0–7.3 (4H,m); 7.3–7.6 (2H,m); 7.6–7.9 (2H,m).

g) 4-[[1-[[[(4-Chlorophenyl)sulfonyl]amino]methyl]cyclopentyl]methyl]benzoic acid To a solution which is maintained at 0° C. of 0.8 g (2.0 mmoles) of the compound prepared in example 25f in 17 ml acetone, there is added 1.2 ml of the Jones reagent (prepared by addition at 0° C. of a mixture of 0.65 ml of concentrated sulfuric acid and 0.52 ml of water to 0.41 g (4.1 mmoles) of chromium oxide (VI) dissolves in 0.65 ml water). After stirring 4 h at room temperature, the salts formed are filtrated and washed with acetone. The filtrate concentrated to dryness under reduced pressure is captured with water and extracted with ether. This organic phase is thereafter extracted with 1N sodium hydroxide. The acidification of this aqueous phase with diluted HCl enables to obtain a white precipitate which is purified by recrystallization in a hexane-ethyl acetate mixture to give 0.35 g (yield=42.3%) of a white solid. M.P.=184°-9° C.

| Percentage analysis: $C_{20}H_{22}ClNO_4S$ (MW = 407.912). | | | | | |
|---|---|---|---|---|---|
| | C % | H % | Cl % | N % | S % |
| Calculated | 58.89 | 5.44 | 8.69 | 3.43 | 7.86 |
| Found | 59.02 | 5.34 | 8.75 | 3.43 | 7.77 |

I.R. (KBr): $\nu$ (NH)=3240 cm$^{-1}$; (C=O)=1675 cm$^{-1}$; (SO$_2$)=1320 cm$^{-1}$; (SO$_2$)=1150 cm$^{-1}$. N.M.R. (acetone d$_6$): $\delta$=1.4-1.8 (8H,m); 2.8 (2H,d, J=6.75 Hz, is converted into singulet with CF$_3$COOD); 2.9 (2H,s); 6.5 (1H,t, J=6.75 Hz, exchangeable with CF$_3$COOD); 7.2-8.2 (9H,m, 1H exchangeable with CF$_3$COOD).

EXAMPLE 26

4-[[1-[[[(3,4-Dichlorophenyl)sulfonyl]amino]methyl]cyclopentyl]methyl]benzeneacetic acid a) 1-(Bromomethyl)-4-[2-(trimethylsilyloxy)ethyl]benzene To a solution of 20.9 g (97.2 mmoles) of 4-(bromomethyl)benzeneethanol (obtained in according to Plaue S. and Heissler D., Tetrahedron Lett. (1987) 28, 1401-4), in 150 ml of tetrahydrofuran maintained at 5° C., there is poured dropwise 20.5 ml (97.2 mmoles) of 1,1,1,3,3,3-hexamethyldisilazane, then 13.55 ml (97.2 mmoles) of triethylamine, then finally 12.3 ml (97.2 mmoles) of trimethylsilyl chloride. The reaction mixture is stirred 1 hour at the same temperature, before filtrating the precipitate formed and rinsing it with hexane. The filtrate, concentrated to dryness under reduced pressure, is purified by distillation to give 16.8 g (yield=60.0%) of a colorless liquid. b.p.$_{0.35}$=98°-108° C.

N.M.R. (CDCl$_3$): $\delta$=0.0 (9H,s); 2.7 (2H,t, J=6.75 Hz); 3.7 (2H,t, J=6.75 Hz); 4,3 (2H,s); 6.8-7.5 (4H,m).

b) 1-[[4-(2-Hydroxyethyl)phenyl]methyl]cyclopentanecarbonitrile

To a mixture of 38.9 ml (278 mmoles) of diisopropylamine and 320 ml of tetrahydrofuran, cooled to $-60°$ C., there is successively poured dropwise 174 ml of a solution of 1.6M of n-butyllithium in hexane to which 50 ml of tetrahydrofuran have been added, a mixture of 24 g (252 mmoles) of cyclopentanecarbonitrile and of 50 ml of tetrahydrofuran, 65 ml of 1,3-dimethylimidazolidinone and finally 73.95 g (257 mmoles) of the compound prepared in example 26a. The temperature is allowed to rise to 20° C. After 16 hours at 20° C. the mixture is refluxed during 13 hours. After cooling 1000 ml water are added and the mixture is stirred one hour at room temperature before adding 35 ml concentrated HCl and stirring again one hour. The mixture is extracted with ethyl acetate and is thereafter washed with water, dried over Na$_2$SO$_4$, before being concentrated under reduced pressure. The purification is carried out by distillation which gives 41.1 g (yield=71.1%) of yellow oil. b.P.$_{0.3}$=175°-85° C.

I.R. (film): $\nu$ (OH)=3410 cm$^{-1}$; (C=N)=2240 cm$^{-1}$. N.M.R. (CDCl$_3$): $\delta$=1.25-2.25 (8H,m); 2.4 (1H,s, exchangeable with CF$_3$COOD); 2.8 (2H,s); 2.8 (2H,t, J=6.75 Hz); 3.75 (2H,t, J=6.75 Hz); 6.65-7.5 (4H,m).

c) 4-[[1-[Aminomethyl)cyclopentyl]methyl]benzeneethanol

At room temperature, 7 g (30.5 mmoles) of the compound prepared in example 26b in solution in 17 ml ether is poured dropwise over 7.7 ml of a commercial solution containing 13% of LiAlH$_4$ (1.3 g, 33.55 mmoles) in a mixture of toluene and tetrahydrofuran, to which 7 ml ether has been added. After stirring during 14 hours, there is carefully added 120 ml water then 100 ml ether. The insoluble mineral salts are filtrated. Ether is decanted and the aqueous phase is again extracted with ether. The combined organic phases are washed with water, dried over Na$_2$SO$_4$, then concentrated under reduced pressure, to quantitatively give the expected amine, which is used without other purification.

I.R. (film): $\nu$ (NH$_2$)=3360 cm$^{-1}$; (OH)=3300 cm$^{-1}$. N.M.R. (CDCl$_3$): $\delta$=1.0-1.8 (8H,m); 1.9 (3H,s, exchangeable with D$_2$O); 2.4 (2H,s); 2.6 (2H,s); 2.8 (2H,t, J=6.75 Hz); 3.8 (2H,t, J=6.75 Hz); 6.7-7.4 (4H,m).

d) 3,4-Dichloro-N-[[1-[[4-(2-hydroxyethyl)phenyl]methyl]cyclopentyl]methyl]benzenesulfonamide Obtained by operating as in example 1c, from 3 g (12.8 mmoles) of the compound obtained in example 26c in 50 ml of dichloromethane, 2.15 ml (15.4 mmoles) of triethylamine and 3.15 g (12.8 mmoles) of 3,4-dichlorobenzenesulfonyl chloride, in 10 ml of dichloromethane. After stirring 16 hours at room temperature and the usual treatment, the product is purified by chromatography on a column of silica with a hexane-ethyl acetate mixture 4:1 to give 0.95 g (yield=16.7%) of a yellow oil which crystallizes.

I.R. (film): $\nu$ (OH)=3460 cm$^{-1}$; (NH)=3270 cm$^{-1}$; (SO$_2$)=1330 cm$^{-1}$; (SO$_2$)=1160 cm$^{-1}$. N.M.R. (CDCl$_3$): $\delta$=1.0-2.0 (9H,m, 1H exchangeable with CF$_3$COOD); 2.5 (2H,s); 2.7 (2H,d, J=6.75 Hz, is converted into singulet with CF$_3$COOD); 2.75 (2H,t, J=6.75 Hz); 3.8 (2H,t, J=6.75 Hz); 4.5 (1H,t, J=6.75 Hz, exchangeable with CF$_3$COOD); 6,9 (4H,s); 7.5 (2H,m); 7.8 (1H,m).

e) 4-[[1-[[[(3,4-dichlorophenyl)sulfonyl]amino]methyl]cyclopentyl]methyl]benzeneacetic acid Obtained by operating as in example 25g, from 0.9 g (2 mmoles) of the compound prepared in example 26d in 20 ml acetone and 1.85 ml of Jones reagent (4 mmoles). After two recrystallizations in a hexane-ethyl acetate mixture there is obtained 0.3 g (yield=32.2%) of a white solid. M.P.=134°-5° C.

| Percentage analysis: $C_{21}H_{23}Cl_2NO_4S$ (MW = 456.384) | | | | | |
|---|---|---|---|---|---|
| | C % | H % | Cl % | N % | S % |
| Calculated | 55.27 | 5.08 | 15.54 | 3.07 | 7.02 |
| Found | 55.40 | 4.86 | 15.26 | 3.05 | 6.92 |

I.R. (KBr): $\nu$ (NH)=3210 cm$^{-1}$; (C=O)=1680 cm$^{-1}$; (SO$_2$)=1300 cm$^{-1}$; (SO$_2$)=1140 cm$^{-1}$. N.M.R. (acetone d$_6$): $\delta$=1.25-1.8 (8H,m); 2.65 (2H,s); 2.75 (2H,d, J=6.75 Hz, is converted into singulet with CF$_3$COOD); 3.5 (2H,s); 6.2-6.8 (2H,m in which 1 triplet, J=6.75 Hz, exchangeable with CF$_3$COOD); 7.1 (4H,s); 7.75 (2H,m); 7.9 (1H,m).

EXAMPLE 27

4-[[1-[[[(4-chlorophenyl)sulfonyl]amino]methyl]cyclobutyl]methyl]benzeneacetic acid a) Cyclobutanecarbonitrile A solution of 80 g (799 mmoles) of cyclobutanecarboxylic acid in 250 ml of dichloromethane is refluxed. 115.6 g (819 mmoles) of chlorosulfonylisocyanate are poured slowly dropwise. Reflux is continued one hour after the end of the addition, until complete evolution of $CO_2$. The reaction mixture is then cooled to 10° C. During 15 min., 119.6 g (1638 mmoles) of N,N-dimethylformamide are poured dropwise therein, before allowing stirring ¼ hour at room temperature. Then, the mixture is poured over ice-water, before extracting it with dichloromethane. The organic phase washed with water, is dried over $Na_2SO_4$, and concentrated under vacuum. The distillation of the residue gives 43.5 g (yield=66.5%) of a colorless liquid. $b.p._{15} = 50°$ C.

I.R. (film): $\nu$ (C≡N)=2250 $cm^{-1}$. N.M.R. ($CDCl_3$): $\delta=1.5-2.7$ (6H,m); 2.7–3.4 (1H,m).

b) 1-[(Phenyl)methyl]cyclobutanecarbonitrile

To a solution under a flow of nitrogen and maintained at −30° C., of 82.3 ml (583 mmoles) of N,N-diisopropylamine in 600 ml of dried tetrahydrofuran, there is poured dropwise 364.4 ml (583 mmoles) of a 1.6M solution in hexane of n-butyllithium, then 83.4 ml of 1,3-dimethylimidazolidinone. The mixture is stirred ¼ hour at −60° C. before cooling to −75° C. to add dropwise a mixture of 43.5 g (530 mmoles) of the compound prepared in example 27a and 500 ml of dried tetrahydrofuran. The mixture is stirred 1 hour at −75° C. and 67.1 g (530 mmoles) of benzyl chloride are added dropwise. The mixture is stirred 1 hour at −75° C. before pouring the reaction mixture over a ice-concentrated HCl mixture. The mixture is extracted with ether, and is washed with water until neutrality, before drying it over $Na_2SO_4$. After removing of the solvent under reduced pressure and distillation of the residue there is obtained 68.1 g (yield=75.9%) of a colorless liquid. which crystallizes at about −20° C. $b.p._{15}=140°$ C. ($b.P._{0.1}=118°$ according to Mousseron M., Jacquier R. and Fraisse R., Compt. Rend. Acad. Sci., Paris (1955), 241, 602–4).

I.R. (film): $\nu$ (C≡N)=2220 $cm^{-1}$. N.M.R.: $\delta=1.75-2.6$ (6H,m); 2.9 (2H,s); 7.2 (5H,s).

c) 1-[(Phenyl)methyl]cyclobutyl]methanamine

Obtained by operating as in example 15a, from 18.3 g (482 mmoles) of $LiAlH_4$ in 450 ml ether and 68.1 g (402 mmoles) of the compound prepared in example 27b in 170 ml ether. After stirring it 2 hours at room temperature and the usual treatment, there is obtained 68.4 g (yield=97.1%) of a yellow oil, used without other purification.

I.R. (film): $\nu$ ($NH_2$)=3360 $cm^{-1}$. N.M.R. ($CDCl_3$): $\delta=1.25$ (2H,s, exchangeable with $CF_3COOD$); 1.8 (6H,m); 2.6 (2H,s); 2.7 (2H,s); 7.1 (5H,s).

d) 4-Chloro-N-[[1-[(phenyl)methyl]cyclobutyl]methyl]-benzenesulfonamide

Obtained by operating as in example 1c, from 10 g (57 mmoles) of the amine prepared in example 27c, in 100 ml of dichloromethane, with 7 g (68.4 mmoles) of triethylamine and 12.4 g (59.3 mmoles) of 4-chlorobenzenesulfonyl chloride. The beige solid obtained is used without purification (16.3 g; yield=81.9%). A fraction which is recrystallized in ethyl acetate gives a white solid. M.P.=144°–8° C.

| Percentage analysis: $C_{18}H_{20}ClNO_2S$ (MW = 349.875) | | | | | |
|---|---|---|---|---|---|
| | C % | H % | Cl % | N % | S % |
| Calculated | 61.79 | 5.76 | 10.13 | 4.00 | 9.16 |
| Found | 61.52 | 6.01 | 10.34 | 4.22 | 9.30 |

I.R. (KBr): $\nu$ (NH)=3250 $cm^{-1}$; ($SO_2$)=1315 $cm^{-1}$; ($SO_2$)=1150 $cm^{-1}$. N.M.R. ($CDCl_3$): $\delta=1.5-2.2$ (6H,m); 2.7 (2H,s); 2.8 (2H,d, J=6.75 Hz, is converted into singulet with $CF_3COOD$); 4.7 (1H,t, J=6.75 Hz, exchangeable with $CF_3COOD$); 6.8–7.25 (5H,m); 7.25–7.5 (2H,m); 7.6–7.9 (2H,m).

e) N-[[1-[(4-Acetylphenyl)methyl]cyclobutyl]methyl]-4-chlorobenzenesulfonamide

Obtained by operating as in example 16b, from 4 g (11.4 mmoles) of the compound prepared in example 27d in 160 ml of dichloromethane, with 1.2 g (14.8 mmoles) of acetyl chloride, and 5 g (37.6 mmoles) of aluminum chloride. The purification carried out by chromatography on a column of silica with a hexane-ethyl acetate mixture gives 2.9 g (yield=65.0%) of a beige solid. M.P.=158°–60° C. A fraction recrystallized in ethyl acetate-heptane gives a white product. M.P.=158°–60° C.

| Percentage analysis: $C_{20}H_{22}ClNO_3S$ + 0.6 $H_2O$ (MW = 402.722) | | | | | |
|---|---|---|---|---|---|
| | C % | H % | Cl % | N % | S % |
| Calculated | 59.65 | 5.81 | 8.80 | 3.48 | 7.96 |
| Found | 59.60 | 5.46 | 8.88 | 3.58 | 8.26 |

I.R. (KBr): $\nu$ (NH)=3270 $cm^{-1}$; (C=O)=1670 $cm^{-1}$; ($SO_2$)=1320 $cm^{-1}$; ($SO_2$)=1155 $cm^{-1}$. N.M.R. ($CDCl_3$): $\delta=1.35-2.2$ (6H,m); 2.55 (3H,s); 2.8 (2H,s); 2.9 (2H,d, J=6.75 Hz, is converted into singulet with $CF_3COOD$); 5.05 (1H,t, J=6.75 Hz, exchangeable with $CF_3COOD$); 7.0–8.0 (8H,m).

f) Methyl 4-[[1-[[[(4-chlorophenyl)sulfonyl]amino]methyl]cyclobutyl]methyl]benzeneacetate Obtained by operating as in example 5e, from 2.1 g (5.3 mmoles) of the compound prepared in example 27e, 2.5 ml (58.3 mmoles) of methanol in 50 ml of dichloromethane, with 5.2 ml (42.4 mmoles) of boron trifluoride etherate and 2.6 g (5.6 mmoles) of lead tetraacetate in 40 ml of toluene. Purification by recrystallization in ethyl acetate gives 0.9 g (yield=42.8%) of a white solid. M.P.=135°–7° C.

I.R. (KBr): $\nu$ (NH)=3250 $cm^{-1}$; (C=O)=1715 $cm^{-1}$; ($SO_2$)=1320 $cm^{-1}$; ($SO_2$)=1160 $cm^{-1}$. N.M.R. ($CDCl_3$): $\delta=1.7-2.0$ (6H,m); 2.7 (2H,s); 2.9 (2H,d, J=6.75 Hz, is converted into singulet with $CF_3COOD$); 3.6 (2H,s); 3.7 (3H,s); 4.4 (1H,t, J=6.75 Hz, exchangeable with $CF_3COOD$); 6.9–7.9 (8H,m).

g) 4-[[1-[[[(4-Chlorophenyl)sulfonyl]amino]methyl]cyclobutyl]methyl]benzeneacetic acid Obtained by operating as in example 5f, from 0.9 g (2.1 mmoles) of the ester prepared in example 27f, 40 ml ethanol and 0.23 g (4.2 mmoles) of potassium hydroxide pellets dissolve in 10 ml water. After recrystallization in an ethyl acetate-heptane mixture, 0.3 g (yield=34.9%) of a white solid is obtained. M.P.=168°–70° C.

| Percentage analysis: $C_{20}H_{22}ClNO_4S$ (MW = 407.912) | | | | | |
|---|---|---|---|---|---|
| | C % | H % | Cl % | N % | S % |
| Calculated | 58.89 | 5.43 | 8.69 | 3.43 | 7.86 |
| Found | 59.01 | 5.36 | 8.65 | 3.45 | 8.01 |

I.R. (KBr): $\nu$ (NH)=3230 $cm^{-1}$; (C=O)=1720 $cm^{-1}$; ($SO_2$)=1315 $cm^{-1}$; ($SO_2$)=1160 $cm^{-1}$. N.M.R. (DMSO $d_6$): $\delta=1.3-2.1$ (6H,m); 2.6–2.8 (4H,m); 3.45 (2H,s); 7.05 (4H,s); 7.5–7.95 (5H,m, 1H exchangeable with $CF_3COOD$); 11.9 (1H,s wide, exchangeable with $CF_3COOD$).

EXAMPLE 28

4-Chloro-N-[[1-[[4-(2-hydroxyethyl)phenyl]methyl]cyclopentyl]methyl]benzenesulfonamide Obtained by operating as in example 25f from 2.5 g (10.7 mmoles) of 4-[[1-(aminomethyl)cyclopentyl]methyl]benzeneethanol prepared in example 26c, 1.3 g (12.8 mmoles) of triethylamine in 20 ml dichloromethane and 2.1 g (9.8 mmoles) of 4-chlorobenzenesulfonyl chloride in 5 ml ether. After treatment, the residue is purified by chromatography on a column of silica in a hexane-ethyl acetate mixture 2/1, followed by recrystallizations in hexane-ethyl acetate to give 0.4 g (yield=10%) of a white solid. M.P.=131°-2° C.

| Percentage analysis: $C_{21}H_{26}ClNO_3S$ (MW = 407.954) | | | | | |
|---|---|---|---|---|---|
| | C % | H % | Cl % | N % | S % |
| Calculated | 61.83 | 6.42 | 8.69 | 3.43 | 7.86 |
| Found | 61.91 | 6.44 | 8.79 | 3.53 | 8.03 |

I.R. (KBr: $\nu$ (OH)=3530 cm$^{-1}$; (NH)=3250 cm$^{-1}$; (SO$_2$)=1315 cm$^{-1}$; (SO$_2$)=1155 cm$^{-1}$. N.M.R. (CDCl$_3$): $\delta$=1.2-1.8 (9H,m, 1H exchangeable with CF$_3$COOD); 2.6 (2H,s); 2.7 (2H,d, J=6.75 Hz, is converted in singulet with CF$_3$COOD); 2.8 (2H,t, J=6.4 Hz); 3.8 (2H,t, J=6.4 Hz); 4.4 (1H,t, J=6.75 Hz, exchangeable with CF$_3$COOD); 7.0 (4H,s); 7.25-7.55 (2H,m); 7.55-7.9 (2H,m).

EXAMPLE 29

4-[1-[[[(4-Chlorophenyl)sulfonyl]amino]methyl]cyclohexyl]benzeneacetic acid a) 2[[2-[4-(Bromomethyl)phenyl]ethoxy]-3,4,5,6-tetrahydro-2H-pyrane A mixture of 16.9 g (78.5 mmoles) of 4-(bromomethyl)benzeneethanol (prepared according to Plaue S. and Heissler D. Tetrahedron Lett. (1987) 28, 1401-4), 10.6 g (125 mmoles) of 3,4-dihydro-2H-pyrane and 0.16 g of para-toluenesulfonic acid in 160 ml dry ethyl ether, is stirred 16 hours at room temperature. The reaction mixture is thereafter washed with a solution saturated with sodium bicarbonate, then water, dried over Na$_2$SO$_4$ and concentrated, to give 21.5 g (yield=91.5%) of a yellow oil used without other purification.

N.M.R. (CDCl$_3$): $\delta$=1.25-2.0 (6H,m); 2.9 (2H,t, J=6.75 Hz); 3.25-4.15 (4H,m); 4.45 (2H,s); 4.55 (1H,m); 7.2 (4H,s).

b) 4-[2-[(3,4,5,6-Tetrahydro-2H-pyran-2-yl)oxy]ethyl]benzeneacetonitrile 21.5 g (71.8 mmoles) of the compound prepared in example 29a, are added to a solution of 3.9 g (79 mmoles) of sodium cyanide in 50 ml of dimethylsulfoxide heated to 115° C. This temperature is maintained for 5 hours. After cooling, the mixture is poured over H$_2$O before extraction with ether. The organic phase washed with water, dried with Na$_2$SO$_4$ and concentrated, is purified by chromatography on a column of silica with a hexane-ethyl acetate mixture (4:1) to give 9.3 g (yield=52.8%) of a colorless oil.

I.R. (film): $\nu$ (C≡N)=2255 cm$^{-1}$ N.M.R. (CDCl$_3$): $\delta$=1.25-2.0 (6H,m); 2.9 (2H,t, J=6.75 Hz); 3.25-4.25 (4H,m); 3.7 (2H,s); 4.5 (1H,m); 7.2 (4H,s).

c) 1-[4-[2-[(3,4,5,6-Tetrahydro-2H-pyran-2-yl)oxy]ethyl]phenyl]cyclohexanecarbonitrile To a suspension under nitrogen of 3.8 g (94.7 mmoles) of NaH (at 60% in mineral oil) in 125 ml of dry dimethylsulfoxide, maintained at 20° C. with an ice bath, there is poured slowly a solution of 9.3 g (37.9 mmoles) of the compound prepared in example 29b, in 20 ml of dry dimethylsulfoxide. After having stirred 1 hour at room temperature, a mixture of 13.1 g (56.8 mmoles) of 1,5-dibromopentane and 20 ml of dry dimethylsulfoxide is poured. The reaction mixture is stirred 40 hours at room temperature before being added to ice water and extracted with ether. The organic phase washed with water, and dried over Na$_2$SO$_4$ is purified by chromatography on a column of silica with a hexane-ethyl acetate mixture (1:1) to give 10.2 g (yield=85.7%) of an orange colored yellowish oil.

I.R. (film): $\nu$ (C≡N)=2250 cm$^{-1}$. N.M.R. (CDCl$_3$): $\delta$=0.75-2.5 (16H,m); 2.85 (2H,t, J=6.75 Hz); 3.2-4.1 (4H,m); 4.5 (1H,m); 7.0-7.5 (4H,m).

d) 4-[1-(Aminomethyl)cyclohexyl]benzeneethanol

A solution of 10.2 g (32.5 mmoles) of the compound prepared in example 29c in 20 ml of dry ether is added to a suspension under nitrogen of 1.9 g (48.8 mmoles) of LiAlH$_4$ in 100 ml dry ether. The reaction mixture is refluxed during 5 hours. After cooling, 9.5 ml water are added with care, followed by 100 ml ether. The reaction mixture is extracted with N HCl. This aqueous phase is washed with ether, made basic with a concentrated solution of NaOH, then extracted with ether. The ether phase is washed with water, dried over Na$_2$SO$_4$ and concentrated to give 5.9 g (yield=77.8%) of a yellow oil used without other purification.

I.R. (film): $\nu$ (NH$_2$)=3350 cm$^{-1}$; (OH)=3320 cm$^{-1}$. N.M.R. (CDCl$_3$): $\delta$=0.75-2.35 (13H,m, 3H exchangeable by D$_2$O); 2.6 (2H,s); 2.8 (2H,t, J=6.75 Hz); 3.8 (2H,t, J=6.75 Hz); 7.15 (4H,s).

e) 4-Chloro-N-[[1-[4-(2-hydroxyethyl)phenyl]cyclohexyl]methyl]benzenesulfonamide To a solution of 5.9 g (25.2 mmoles) of the compound prepared in example 29 d, 3.0 g (30.2 mmoles) of triethylamine in 60 ml of dry CH$_2$Cl$_2$, maintained at −20° C., there is added 5.2 g (24.7 mmoles) of 4-chlorobenzenesulfonyl chloride. After 3 hours at −20° C., the reaction mixture is poured over a diluted solution of HCl, before being extracted with dichloromethane. The organic phase, washed, dried over Na$_2$SO$_4$ and concentrated, gives an oil which is purified by chromatography on a column of silica with a hexane-ethyl acetate mixture (1:1). There is obtained 1.2 g (yield=11.6%) of an off-white solid. M.P.=110°-1° C.

I.R. (KBr): $\nu$ (OH)=3450 cm$^{-1}$; (NH)=3080 cm$^{-1}$; (SO$_2$)=1310 cm$^{-1}$; (SO$_2$)=1140 cm$^{-1}$. N.M.R. (CDCl$_3$): $\delta$=0.75-2.25 (11H,m, 1H exchangeable by CF$_3$COOD); 2.8 (2H,t, J=6.75 Hz); 2.9 (2H,d, J=6.75 Hz, is converted into singulet with CF$_3$COOD); 3.8 (2H,t, J=6.75 Hz); 4.1 (1H,t, J=6.75 Hz, exchangeable with CF$_3$COOD); 7.1 (4H,s); 7.3 (2H,m); 7.55 (2H,m).

f) 4-[1-[[[(4-Chlorophenyl)sulfonyl]amino]methyl]cyclohexyl]benzeneacetic acid

Obtained by operating as in example 25 g, from 1.2 g (2.9 mmoles) of the compound prepared in example 29e in 120 ml acetone and 2.8 ml (5.9 mmoles) of the Jones reagent. The reaction mixture is stirred 24 hours at room temperature. After 2 recrystallizations in toluene, there is obtained 0.3 g (yield=25.0%) of a white solid. M.P.=147°-51° C.

| Percentage analysis: $C_{21}H_{24}ClNO_4S$ (MW = 421.939) | | | | | |
|---|---|---|---|---|---|
| | C % | H % | Cl % | N % | S % |
| Calculated | 59.78 | 5.73 | 8.40 | 3.32 | 7.60 |

| Percentage analysis: C$_{21}$H$_{24}$ClNO$_4$S (MW = 421.939) | | | | | |
|---|---|---|---|---|---|
| | C % | H % | Cl % | N % | S % |
| Found | 59.52 | 5.70 | 8.34 | 3.22 | 7.57 |

I.R. (KBr): ν (NH)=3290 cm$^{-1}$; (C=O)=1700 cm$^{-1}$; (SO$_2$)=1325 cm$^{-1}$; (SO$_2$)=1160 cm$^{-1}$. N.M.R. (DMSO d$_6$): δ=1.0–2.2 (10H,m); 2.7 (2H,d, J=6.75 Hz, is converted into singulet with CF$_3$COOD); 3.4 (1H,m, exchangeable with CF$_3$COOD); 3.5 (2H,s); 6.9–7.4 (4H,m); 7.4–7.8 (4H,m); 12.2 (1H,s wide, exchangeable with CF$_3$COOD).

EXAMPLE 30

4-[4-[[1-[[[(4-Chlorophenyl)sulfonyl]amino]methyl]cyclopentyl]methyl]phenyl]-4-oxobutanoic acid a) Ethyl 4-[4-[[1-[[[(4-chlorophenyl)sulfonyl]amino]methyl]cyclopentyl]methyl]phenyl]-4-oxobutanoate To a mixture of 25.1 g (69 mmoles) of the compound prepared in example 17a, 12.5 g (75.9 mmoles) of commercial ethyl 3-chloroformylpropanoate and 130 ml of dichloromethane, maintained at 0° C., there is added by portions, 27.6 g (207.0 mmoles) of anhydrous aluminum chloride. The reaction mixture is stirred 2 hours at 0° C. then 1 hour at room temperature, before being poured over a mixture of ice and concentrated hydrochloric acid. After having recovered the organic phase, the aqueous phase is extracted with CH$_2$Cl$_2$. The combined organic phases are washed with H$_2$O, dried over Na$_2$SO$_4$ and concentrated to give 30.9 g (yield=90.9%) of a creamy solid, used without other purification. M.P.=100°-4° C.

I.R. (KBr): ν (NH)=3250 cm$^{-1}$; (C=O)=1710 cm$^{-1}$; (C=O)1690 cm$^{-1}$; (SO$_2$)=1355 cm$^{-1}$; (SO$_2$)=1170 cm$^{-1}$. N.M.R. (CDCl$_3$): δ=1.25 (3H,t, J=6.75 Hz); 1.1–1.8 (8H,m); 2.5–2.9 (6H,m, including one triplet, J=6 Hz); 3.25 (2H,t, J=6 Hz); 4.1 (2H,q, J=6.75 Hz); 4.9 (1H,m, exchangeable with CF$_3$COOD); 7.0–7.25 (2H,m); 7.3–7.6 (2H,m); 7.6–7.9 (4H,m).

b) 4-[4-[[1-[[[(4-chlorophenyl)sulfonyl]amino]methyl]cyclopentyl]methyl]phenyl]-4-oxobutanoic acid To a solution of 10 g (20.2 mmoles) of the compound prepared in example 30a and 200 ml 96° ethanol, there is added 2.2 g (39.2 mmoles) of potassium hydroxide dissolved in 100 ml water. The mixture is stirred 4 hours at 60° C., before being concentrated to dryness under reduced pressure. The solid residue obtained is captured with water, washed with ethyl acetate, then poured dropwise over a diluted hydrochloric acid solution. The white precipitate formed is filtrated, squeezed and dried under vacuum. The product is purified by chromatography on a column of silica in a dichloromethane-methanol mixture (19:1) then by 2 recrystallizations in toluene. There is obtained 5.2 g (yield=55.9%) of a white solid. M.P.=139°-42° C.

| Percentage analysis: C$_{23}$H$_{26}$ClNO$_5$S (MW = 463.975) | | | | | |
|---|---|---|---|---|---|
| | C % | H % | Cl % | N % | S % |
| Calculated | 59.54 | 5.65 | 7.64 | 3.02 | 6.91 |
| Found | 59.39 | 5.81 | 7.62 | 2.93 | 7.17 |

I.R. (KBr): ν (NH)=3300 cm$^{-1}$; (C=O)=1690 cm$^{-1}$; (C=O)=1670 cm$^{-1}$; (SO$_2$)=1330 cm$^{-1}$; (SO$_2$)=1150 cm$^{-1}$. N.M.R. (acetone d$_6$): δ=1.25–1.7 (8H,m); 2.4–2.95 (4H,m); 2.75 (2H,d, =6.75 Hz, is converted into singulet with CF$_3$COOD) 3.3 (2H,t, J=6 Hz); 6.4 (1H,t, J=6.75 Hz, exchangeable with CF$_3$COOD); 7.0–7.95 (8H,m); 10.25 (1H,s wide, exchangeable with CF$_3$COOD).

EXAMPLE 31

4-Chloro-N-[[1-[[4-(4,5-dihydro-3-oxo-2H-pyridazin-6-yl)phenyl]methyl]cyclopentyl]methyl]-benzenesulfonamide To a solution of 3 g (6.5 mmoles) of the compound prepared in example 30b and 40 ml of acetic acid, there is added 1.8 g (35.9 mmoles) of hydrazine hydrate. The mixture is stirrred under reflux during 6 hours. After cooling, the reaction mixture is diluted with water, then extracted with dichloromethane. The organic phase is washed with sodium hydroxide, then with water, dried over Na$_2$SO$_4$ and concentrated to dryness, to give a beige solid. The product is purified by recrystallization in chloroform, then in a chloroform-heptane mixture to give 1.1 g (yield=37.9%) of a white solid. M.P.=187°-8° C.

| Percentage analysis: C$_{23}$H$_{26}$ClN$_3$O$_3$S + 0.5 CHCl$_3$ (MW = 465.965) | | | | | |
|---|---|---|---|---|---|
| | C % | H % | Cl % | N % | S % |
| Calculated | 59.41 | 5.63 | 8.75 | 9.02 | 6.88 |
| Found | 59.49 | 5.59 | 8.49 | 9.30 | 6.93 |

I.R. (KBr): ν (NH)=3270 cm$^{-1}$; (C=O)=1670 cm$^{-1}$; (C≡N)=1645 cm$^{-1}$; (SO$_2$)=1335 cm$^{-1}$; (SO$_2$)=1140 cm$^{-1}$. N.M.R. (acetone d$_6$+DMSO d$_6$): δ=1.25–1.8 (8H,m); 2.25–3.25 (9H,m, 1H exchangeable with CF$_3$COOD); 7.0–7.3 (2H,m); 7.4–7.7 (4H,m); 7.7–8.0 (2H,m); 10.3 (1H,s wide, exchangeable with CF$_3$COOD).

EXAMPLE 32

4-[[1-[[[(2-Chlorophenyl)sulfonyl]amino]methyl]cyclopentyl]methyl]benzeneacetic acid a) 1-[(4-Acetylphenyl)methyl]cyclopentanecarbonitrile To a solution of 92.6 g (0.5 mole) of 1-(phenylmethyl)cyclopentanecarbonitrile (prepared according to Campaigne E. and Forsch R. A., J. Org. Chem. (1978) 43, 1044–50) in 2000 ml of dichloromethane maintained at −5° C., there is added 78.5 g (1 mole) of acetyl chloride, and by portions 200 g (1.5 mole) of aluminum chloride. The temperature is maintained at −5° C. during 2 hours, then is allowed to rise at room temperature to stir 16 hours. The reaction mixture is poured over a mixture of ice+water+hydrochloric acid and extracted with dichloromethane. The organic phase is washed to neutrality, dried over Na$_2$SO$_4$ and concentrated to give a red oil in which there remains about 60% of the starting product. This oil is then treated again in 2000 ml of dichloromethane with 78.5 g (1 mole) of acetyl chloride and 200 g (1.5 mole) of aluminum chloride under reflux during 4 hours. After cooling, the reaction mixture is poured into a mixture of ice+water+hydrochloric acid, before being extracted with dichloromethane. The organic phase dried over Na$_2$SO$_4$ is concentrated to give a dark red oil, purified by distillation. There is obtained 76.5 g (yield=67.6%) of a yellow oil which crystallizes. b.p.$_{0.4}$=120°-60° C. A fraction of this product is recrystallized in an ethyl acetate-hexane mixture to give a white solid. M.P.=46°-8° C.

| Percentage analysis: C₁₅H₁₇NO (MW = 227.305) | | | |
|---|---|---|---|
| | C % | H % | N % |
| Calculated | 79.26 | 7.54 | 6.16 |
| Found | 79.59 | 7.61 | 6.14 |

I.R. (KBr): ν (C≡N)=2200cm⁻¹; (C=O)=1650 cm⁻¹. N.M.R. (CDCl₃): δ=1.5-2.4 (8H,m); 2.6 (3H,s); 2.9 (2H,s); 7.25-7.5 (2H,m); 7.75-8.0 (2H,m).

b) Methyl 4-[(1-cyanocyclopentyl)methyl]benzeneacetate

Obtained by operating as in example 5e from 39.9 g (175.5 mmoles) of the compound prepared in example 32a, 126 ml of methanol in 630 ml of dichloromethane, 99.6 g (702 mmoles) of boron trifluoride etherate and 81.6 g (184.2 mmoles) of lead tetraacetate in solution in 200 ml of dichloromethane. There is obtained 44.8 g (yield=99.2%) of a yellow oil used without other purification.

I.R. (film): ν (C≡N)=2260 cm⁻¹; (C=O)=1715 cm⁻¹. N.M.R. (CDCl₃): δ=1.5-2.25 (8H,m); 2.8 (2H,s); 3.6 (2H,s); 3.65 (3H,s); 7.15 (4H,s).

c) 4-[[1-(Aminomethyl)cyclopentyl]methyl]benzeneethanol

To a suspension at 35° C. under a flow of nitrogen, of 12.5 g (332.9 mmoles) of LiAlH₄ in 242 ml of tetrahydrofuran, there is added 25.2 g (97.9 mmoles) of the compound prepared in example 32b in solution in 121 ml of tetrahydrofuran. The reaction mixture is refluxed 6.5 hours. After cooling, 68 ml of water is carefully poured therein, then the mixture is diluted with ethyl ether before filtering the precipitate formed. The filtrate is diluted with water before being extracted with ether. The organic phase, washed with water, is dried over Na₂SO₄ and concentrated. The oil obtained is captured with a diluted solution of HCl, washed with ether. This aqueous phase is made basic with Na₂CO₃, extracted with dichloromethane which is thereafter washed with water and dried over Na₂SO₄, before being concentrated. There is obtained 20.6 g (yield=90.1%) of a yellow oil used without other purification.

A portion of this oil is purified by chromatography on silica in a chloroform-methanol mixture (9:1), then by distillation to give a pale yellow oil. b.p.₀.₃=150°-3° C.

| Percentage analysis: C₁₅H₂₃NO (MW = 233.355) | | | |
|---|---|---|---|
| | C % | H % | N % |
| Calculated | 77.21 | 9.94 | 6.00 |
| Found | 77.13 | 9.99 | 6.17 |

The I.R. and N.M.R. spectra are identical to those obtained in example 26c.

d) 2-Chloro-N-[[1-[[4-(2-hydroxyethyl)phenyl]methyl]-cyclopentyl]methyl]-benzenesulfonamide To a mixture of 3 g (12.9 mmoles) of the compound prepared in example 32c and 1.6 g (15.8 mmoles) of triethylamine in 30 ml of dry dichloromethane, maintained at −15° C., there is added 2.6 g (12.3 mmoles) of commercial 2-chlorobenzenesulfonyl chloride dissolved in 30 ml of dichloromethane. After having stirred the reaction mixture 3 hours at −15° C., it is poured over a ice-water mixture, before extracting it with dichloromethane. The organic phase is washed with N HCl, rinsed with water, dried over Na₂SO₄ and concentrated. The residual white solid, 4.7 g (yield=90.4%) is used without other purification. M.P.=126°-8° C. A fraction which is purified by recrystallizations in an ethyl acetateheptane mixture gives a white powder. M.P.=127°-9° C.

| Percentage analysis: C₂₁H₂₆ClNO₃S (MW = 407.954) | | | | | |
|---|---|---|---|---|---|
| | C % | H % | Cl % | N % | S % |
| Calculated | 61.83 | 6.42 | 8.69 | 3.43 | 7.86 |
| Found | 61.80 | 6.30 | 9.10 | 3.48 | 7.89 |

I.R. (KBr): ν (OH)=3570 cm⁻¹; (NH)=3300 cm⁻¹; (SO₂)=1320 cm⁻¹; (SO₂)=1160 cm⁻¹. N.M.R. (CDCl₃): δ=1.25-1.9 (9H,m, 1H exchangeable with CF₃COOD); 2.6 (2H,s); 2.6 (2H,d, J=6.75 Hz, is converted into singulet with CF₃COOD); 2.8 (2H,t, J=6.75 Hz); 3.8 (2H,t, J=6.75 Hz); 4.8 (1H,m, exchangeable with CF₃COOD); 7.1 (4H,s); 7.25-7.6 (3H,m); 7.8-8.2 (1H,m).

e) 4-[[1-[[[(2-chlorophenyl)sulfonyl]amino]methyl]cyclopentyl]methyl]benzeneacetic acid Obtained by operating as in example 25 g, from 4.2 g (10.3 mmoles) of the compound prepared in example 32d, dissolved in 140 ml acetone and 9.6 ml of Jones reagent (20.5 mmoles). After two recrystallizations in an ethyl acetate-heptane mixture, there is obtained 0.9 g (yield=20.9%) of a white powder. M.P.=147°-9° C.

| Percentage analysis: C₂₁H₂₄ClNO₄S (MW = 421.940) | | | | | |
|---|---|---|---|---|---|
| | C % | H % | Cl % | N % | S % |
| Calculated | 59.78 | 5.73 | 8.40 | 3.32 | 7.60 |
| Found | 59.83 | 5.81 | 8.17 | 3.58 | 7.73 |

I.R. (KBr): ν (NH)=3280 cm⁻¹; (C=O)=1690 cm⁻¹; (SO₂)=1320 cm⁻¹; (SO₂)=1155 cm⁻¹. N.M.R. (CDCl₃): δ=1.1-1.8 (8H,m); 2.6 (2H,d, J=6.75 Hz, is converted into singulet with CF₃COOD); 2.6 (2H,s); 3.6 (2H,s); 5.0 (1H,t, J=6.75 Hz, exchangeable with CF₃COOD); 6.5 (1H,s wide, exchangeable with CF₃COOD); 7.1 (4H,s); 7.4-7.6 (3H,m); 7.85-8.1 (1H,m).

EXAMPLES 33 to 51

The compounds of examples 33 to 51:

3-Chloro-N-[[1-[[4-(2-hydroxyethyl)phenyl]methyl]cyclopentyl]methyl]benzenesulfonamide 4-Bromo-N-[[1-[[4-(2-hydroxyethyl)phenyl]methyl]cyclopentyl]methyl]benzenesulfonamide N-[[1-[[4-(2-Hydroxyethyl)phenyl]methyl]cyclopentyl]methyl]-4-iodobenzenesulfonamide N-[[1-[[4-(2-Hydroxyethyl)phenyl]methyl]cyclopentyl]methyl]-4-trifluoromethylbenzenesulfonamide N-[[1-[[4-(2-Hydroxyethyl)phenyl]methyl]cyclopentyl]methyl]-3-trifluoromethylbenzenesulfonamide 4-Cyano-N-[[1-[[4-(2-hydroxyethyl)phenyl]methyl]cyclopentyl]methyl]benzenesulfonamide N-[[1-[[4-(2-Hydroxyethyl)phenyl]methyl]cyclopentyl]methyl]-3-nitrobenzenesulfonamide 2,4-Dichloro-N-[[1-[[4-(2-hydroxyethyl)phenyl]methyl]cyclopentyl]methyl]benzenesulfonamide N-[[1-[[4-(2-Hydroxyethyl)phenyl]methyl]cyclopentyl]methyl]-4-(1-methylethyl)benzenesulfonamide 4-(1,1-Dimethylethyl)-N-[[1-[[4-(2-hydroxyethyl)-phenyl]methyl]cyclopentyl]methyl]-benzenesulfonamide 4-Acetyl-N-[[1-[[4-(2-hydroxyethyl)phenyl]methyl]cyclopentyl]methyl]-benzenesulfonamide N-[[1-[[4-(2-Hydroxyethyl)phenyl]methyl]cyclopentyl]methyl]-4-methylsulfonylbenzenesulfonamide N-[[1-[[4-(2-Hydroxyethyl)phenyl]methyl]cyclopentyl]methyl]-4-trifluoromethoxybenzenesulfonamide N-[[1-[[4-(2-Hydroxyethyl)phenyl]methyl]cyclopentyl]methyl]-4-methoxybenzenesulfonamide N-[[1-[[4-(2-Hydroxyethyl)phenyl]methyl]cyclopentyl]methyl]-3-methylquinol-8-ylsulfonamide N-[[1-[[4-(2-Hydroxyethyl)phenyl]methyl]cyclopentyl]methyl]-thien2-yl-sulfonamide 5-Chloro-N-[[1-[[4-(2-hydroxyethyl)phenyl]methyl]cyclopentyl]methyl]-thien-2-ylsulfonamide N-[[1-[[4-[1-[(2-Hydroxyethyl)phenyl]methyl]cyclopentyl]methyl]-imizadolyl-4-ylsulfonamide N-[[1-[[4-(2-Hydroxyethyl)phenyl]methyl]cyclopentyl]methyl]-fur-2-ylsulfonamide have been prepared according to example 32d, and their characteristics are given in tables Ia to Ie:

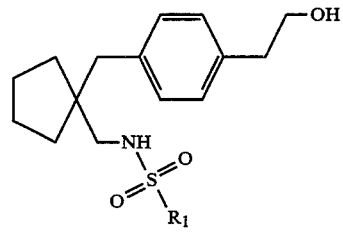

TABLE Ia

| Ex. No. | $R_1$ | Empirical formula[a] | M.P. (°C.) | NMR($\delta$, CDCl$_3$) |
|---|---|---|---|---|
| 33 | 3-Cl-C$_6$H$_4$ | C$_{21}$H$_{26}$ClNO$_3$S (407.956) | 94.3–95.4 (ethyl acetate-hexane) | 1.3–1.9(9H, m, 1H exchange with CF$_3$COOD); 2.6(2H, s); 2.7(2H, d, J=6.75Hz, is converted into s with CF$_3$COOD); 2.8(2H, t, J=6.75Hz); 3.8(2H, t, J=6.75Hz); 4.35(1H, t, J=6.75Hz, exchangeable with CF$_3$COOD); 7.0 (4H, s); 7.2–7.9(4H, m) |
| 34 | 4-Br-C$_6$H$_4$ | C$_{21}$H$_{26}$BrNO$_3$S (452.407) | 138–142 (ethyl acetate-heptane) | 1.25–1.75(9H, m, 1H exchangeable with CF$_3$COOD); 2.6(2H, s); 2.7(2H, d, J=6.75Hz, is converted into s with CF$_3$COOD); 2.8(2H, t, J=6.75Hz); 3.8(2H, t, J=6.75Hz); 4.4(1H, t, J=6.75Hz, exchangeable with CF$_3$COOD; 7.0(4H, s); 7.6(4H, s) |
| 35 | 4-I-C$_6$H$_4$ | C$_{21}$H$_{26}$INO$_3$S (499.407) | 146–148 (ethyl acetate-heptane) | 1.0–1.7(8H, m); 2.6(4H, m); 2.75(2H, t, J=6.75Hz); 3.6(1H, s, exchangeable with CF$_3$COOD); 3.7(2H, t, J=6.75Hz); 6.45 (1H, m, exchangeable with CF$_3$COOD); 7.0(4H, s); 7.4–7.36(2H, m); 7.7–7.9 (2H, m) |
| 36 | 4-CF$_3$-C$_6$H$_4$ | | 102–103 | 1.25–1.85(8H, m); 1,5(1H, s, exchangeable with CF$_3$COOD); 2.6(2H, s); 2.75(2H, d, J=6.75Hz, is converted into s with CF$_3$COOD); 2.8(2H, t, J=6,75Hz); 3.8(2H, t, J=6.75Hz); 4.5(1H, t, J=6.75Hz, exchangeable with CF$_3$COOD); 6.75–7.3 (4H, m); 7.6–8.0(4H, m) |

[a]Percentage analysis: C, H, Cl, Br, N, S ± 0.29 except example 35, S= +0.6

TABLE Ib

| Ex. No. | $R_1$ | Empirical formula[a] | M.P. (°C.) | NMR($\delta$, CDCl$_3$) |
|---|---|---|---|---|
| 37 | 3-CF$_3$-C$_6$H$_4$ | | 102–103 | 1.26–1.8(8H, m); 1.6(1H, s, exchangeable with CF$_3$COOD); 2.6(2H, s); 2.75(2H, d, J=6.75Hz, is converted into s with CF$_3$COOD); 2.8(2H, t, J=6.75Hz); 3.8 (2H, t, J=6.75Hz); 4.6(1H, t, J=6.75Hz exchangeable with CF$_3$COOD); 7.0(4H, s); 7.5–8.15(4H, m) |
| 38 | 4-CN-C$_6$H$_4$ | C$_{22}$H$_{26}$N$_2$O$_3$S (398.521) | 103–104 (ethyl acetate-hexane) | 1.3–1.8(8H, m); 1.5(1H, s, exchangeable with CF$_3$COOD); 2.55(2H, s); 2.65(2H, d, J=6.75Hz, is converted into s with CF$_3$COOD); 2.75(2H, t, J=6.75Hz); 3.8(2H, t, J=6.75Hz); 4.3(1H, t, J=6.75Hz, exchangeable with CF$_3$COOD); 7.0(4H, s); 7.56–8.0(4H, m) |

TABLE Ib-continued

| Ex. No. | R₁ | Empirical formula[a] | M.P. (°C.) | NMR(δ, CDCl₃) |
|---|---|---|---|---|
| 39 | 3-nitrophenyl | | oil | 1.25–1.8(8H, m); 2.0(1H, s, exchangeable with CF₃COOD); 2.6(2H, 3); 2.7(2H, d, J=6.75Hz, is converted into s with CF₃COOD); 2.8(2H, t, J=6.75Hz); 3.8 (2H, t, J=6.75Hz); 6.0(1H, t, J=6.75Hz, exchangeable with CF₃COOD); 7.0(4H, s); 7.45–8.66(4H, m) |
| 40 | 2,4-dichlorophenyl | | 100 | |

[a]Percentage analysis: C, H, N, S ± 0.11

TABLE Ic

| Ex. No. | R₁ | Empirical formula[a] | M.P. (°C.) | NMR(δ, CDCl₃) |
|---|---|---|---|---|
| 41 | 4-(1-methylethyl)phenyl (CH(CH₃)₂) | | oil | 1.06–1.75(8H, m); 1.2(6H, d, J=6.75Hz); 1.8(1H, s, exchangeable with CF₃COOD); 2.55(2H, s); 2.7(2H, d, J=6.75Hz, is converted into s with CF₃COOD); 2.8(2H, t, J=6.75Hz); 2.95(1H, m); 3.8(2H, t, J=6.75Hz); 4.7(1H, t, J=6.75Hz, exchangeable with CF₃COOD); 6.95(4H, s); 7.15–7.4(2H, m); 7.6–7.9(2H, m) |
| 42 | 4-tert-butylphenyl (C(CH₃)₃) | | 108–111 (ethyl acetate-hexane) | 1.25–1.75(8H, m); 1.3(9H, s); 1.6(1H, s, exchangeable with CF₃COOD); 2.6(2H, s); 2.7(2H, d, J=6.75Hz, is converted into s with CF₃COOD); 2.8(2H, t, J=6.75Hz); 3.8(2H, t, J=6.75Hz); 4.4(1H, t, J=6.75 Hz, exchangeable with CF₃COOD); 7.0 (4H, s); 7.35–7.6(2H, m); 7.6–7.9(2H, m) |
| 43 | 4-acetylphenyl (C(=O)CH₃) | $C_{23}H_{29}NO_4S$ (415.548) | 68–69.5 (ethyl acetate-hexane) | 1.25–1.8(8H, m); 1.9(1H, s, exchangeable with CF₃COOD); 2.6(7H, m); 2.8(2H, t, J=6.75Hz); 3.8(2H, t, J=6.75Hz); 4.8 (1H, t, J=6.75Hz, exchangeable with CF₃COOD); 7.0(4H, s); 7.7–8.2(4H, m) |
| 44 | 4-(methylsulfonyl)phenyl (S(=O)₂CH₃) | $C_{22}H_{29}NO_5S_2$ +0.2 H₂O (455.207) | 115.5–116.5 (ethyl acetate) | 1.25–1.8(8H, m); 1.75(1H, s, exchangeable with CF₃COOD); 2.6(2H, s); 2.7(2H, d, J=6.75Hz, is converted into s with CF₃COOD); 2.8(2H, t, J=6.75Hz); 3.1(3H, s); 3.8(2H, t, J=6.75Hz); 4.5(1H, t, J=6.75Hz, exchangeable with CF₃COOD); 7.0(4H, m); 8.0(4H, m) |

[a]Percentage analysis: C, H, N, S ± 0.30

TABLE Id

| Ex. No. | R₁ | Empirical formula[a] | M.P. (°C.) | NMR(δ, CDCl₃) |
|---|---|---|---|---|
| 45 | 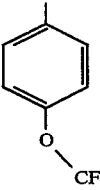 | $C_{22}H_{26}F_3NO_4S$ (457.507) | 71–73 (ethyl acetate-hexane) | 1.25–1.75(8H, m); 1.6(1H, s, exchangeable with CF₃COOD); 2.6(2H, s); 2.7(2H, d, J=6.75Hz, is converted into s with CF₃COOD); 2.8(2H, t, J=6.75Hz); 3.8(2H, t, J=6.75Hz); 4.55(1H, t, J=6.75Hz, exchangeable with CF₃COOD); 7.05(4H, s); 7.1–7.4(2H, m); 7.7–8.0 (2H, m) |
| 46 | 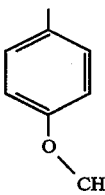 | $C_{22}H_{29}NO_4S$ (403.537) | 139.5–141.6 (ethyl acetate) | 1.25–1.75(8H, m); 1.55(1H, s, exchangeable with CF₃COOD); 2.5(2H, s); 2.6(2H, d, J=6.75Hz, is converted into s with CF₃COOD); 2.75(2H, t, J=6.75Hz); 3.75(2H, t, J=6.75Hz); 3.8(3H, s); 4.3(1H, m, exchangeable with CF₃COOD); 6.75–7.1(2H, m); 7.0(4H, s); 7.55–7.8 (2H, m) |
| 47 | 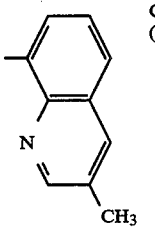 | $C_{25}H_{30}N_2O_3S$ (438.586) | 140–142 (ethyl acetate-hexane) | 1.25–1.76(8H, m); 1.5(1H, s, exchangeable with CF₃COOD); 2.45–3.0(9H, m); 3.8(2H, t, J=6.75Hz); 6.3(1H, m, exchangeable with CF₃COOD); 7.0(4H, m); 7.3–8.4(4H, m); 8.8(1H, m) |
| 48 |  | $C_{19}H_{25}NO_3S_2$ (379.533) | 119–121 (ethyl acetate-hexane) | 1.25–1.75(8H, m); 1.55(1H, s, exchangeable with CF₃COOD); 2.6(2H, s); 2.7(2H, d, J=6.75Hz, is converted into s with CF₃COOD); 2.8(2H, t, J=6.75Hz); 3.8(2H, t, J=6.75Hz); 4.5(1H, t, J=6.75Hz, exchangeable with CF₃COOD); 6.8–7.25(5H, m); 7.4–7.65(2H, m) |

[a]Percentage analysis: C, H, F, N, S ± 0.19 except example 48, S ± 0.5

TABLE Ie

| Ex. No. | R₁ | Empirical formula[a] | M.P. (°C.) | NMR(δ, CDCl₃) |
|---|---|---|---|---|
| 49 | 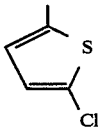 | $C_{19}H_{24}ClNO_3S_2$ (413.978) | 98–100 (ethyl acetate-hexane) | 1.25–1.75(8H, m); 1.5(1H, s, exchangeable with D₂O); 2.6(2H, s); 2.75(2H, d, J=6.75Hz); 2.8(2H, t, J=6.75Hz); 3.8(2H, t, J=6.75Hz); 4.4(1H, t, J=6.75Hz); 6.75–6.9(1H, m); 7.0 (4H, m); 7.1–7.35(1H, m) |
| 50 | 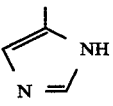 | $C_{18}H_{25}N_3O_3S$ (363.476) | 182–184 (ethanol-water) | (DMSO d₆): 1.1–1.75(8H, m); 2.4–2.85 (6H, m); 3.25–3.75(2H, t, J=6.75Hz); 4.3–4.7(1H, m, exchangeable with CF₃COOD); 6.9(4H, s); 7.3(1H, t, J=6.75Hz, exchangeable with CF₃COOD); 7.55(1H, s); 7.8(1H, s); 12.5(1H, m, exchangeable with CF₃COOD) |
| 51 |  | | oil | 1.25–1.8(9H, m, 1H exchangeable with D₂O); 2.6(2H, s); 2.65–3.0(4H, m); 3.8(2H, t, J=6.75Hz); 4.6(1H, m); 6.3–6.6(1H, m); 6.8–7.25(5H, m); 7.4–7.65(1H, m) |

[a]Percentage analysis: C, H, Cl, N, S ± 0.26 except example 50, C=−0.44

EXAMPLES 52 to 70

The compounds of examples 52 to 70:

4-[[1-[[[(3-Chlorophenyl)sulfonyl]amino]methyl]cyclopentyl]methyl]benzeneacetic acid 4-[[1-[[[(4-Bromophenyl)sulfonyl]amino]methyl]cyclopentyl]methyl]benzeneacetic acid 4-[[1-[[[(4-Iodophenyl)sulfonyl]amino]methyl]cyclopentyl]methyl]benzeneacetic acid 4-[[1-[[[(4-Trifluoromethylphenyl)sulfonyl]amino]methyl]cyclopentyl]methyl]benzeneacetic acid 4-[[1-[[[(3-Trifluoromethylphenyl)sulfonyl]amino]methyl]cyclopentyl]methyl]benzeneacetic acid 4-[[1-[[[(4-Cyanophenyl)sulfonyl]amino]methyl]cyclopentyl]methyl]benzeneacetic acid 4-[[1-[[[(3-Nitrophenyl)sulfonyl]amino]methyl]cyclopentyl]methyl]benzeneacetic acid 4-[[1-[[[(2,4-Dichlorophenyl)sulfonyl]amino]methyl]cyclopentyl]methyl]benzeneacetic acid 4-[[1-[[[[4-(1-Methylethyl)phenyl]sulfonyl]amino]methyl]cyclopentyl]methyl]benzeneacetic acid 4-[[1-[[[[4-(1,1-Dimethylethyl)phenyl]sulfonyl]amino]methyl]cyclopentyl]methyl]benzeneacetic acid 4-[[1-[[[(4-Acetylphenyl)sulfonyl]amino]methyl]cyclopentyl]methyl]benzeneacetic acid 4-[[1-[[[(4-Methylsulfonylphenyl)sulfonyl]amino]methyl]cyclopentyl]methyl]benzeneacetic acid 4-[[1-[[[(4-Trifluoromethoxyphenyl)sulfonyl]amino]methyl]cyclopentyl]methyl]benzeneacetic acid 4-[[1-[[[(4-Methoxyphenyl)sulfonyl]amino]methyl]cyclopentyl]methyl]benzeneacetic acid 4-[[1-[[[(3-Methylquinol-8-yl)sulfonyl]amino]methyl]cyclopentyl]methyl]benzeneacetic acid 4-[[1-[[[(Thien-2-yl)sulfonyl]amino]methyl]cyclopentyl]methyl]benzeneacetic acid 4-[[1- [[[(5-Chlorothien-2-yl)sulfonyl]amino]methyl]cyclopentyl]methyl ]benzeneacetic acid 4-[[1-[[[(Imidazol-4-yl)sulfonyl]amino]methyl]cyclopentyl]methyl]benzeneacetic acid 4-[[1-[[[(fur-2-yl)sulfonyl]amino]methyl]cyclopentyl]methyl]benzeneacetic acid have been prepared according to example 25g, and their characteristics are given in tables IIa to IIe:

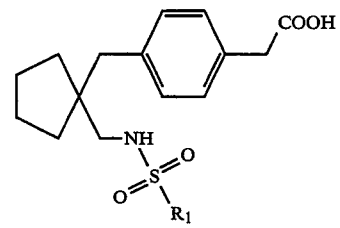

TABLE IIa

| Ex. No. | $R_1$ | Empirical formula[a] | M.P. (°C.) | NMR($\delta$, acetone $d_6$) |
|---|---|---|---|---|
| 52 | (3-Cl-phenyl) | $C_{21}H_{24}ClNO_4S$ (421.939) | 121.8–121.9 (ethyl acetate-hexane) | 1.35–1.75(8H, m); 2.7(2H, s); 2.8(2H, d, J=6.75Hz, is converted into s with $CF_3COOD$); 3.6(2H, s), 6.45(1H, t, J=6.75Hz, exchangeable with $CF_3COOD$); 7.1(4H, s); 7.5–7.9(4H, m); 10.45(1H, s wide, exchangeable with $CF_3COOD$) |
| 53 | (4-Br-phenyl) | $C_{21}H_{24}BrNO_4S$ (466.39) | 149–150 (ethyl acetate-heptane) | 1.35–1.75(8H, m); 2.6(2H, s); 2.7(2H, d, J=6.75Hz, is converted into s with $CF_3COOD$); 3.5(2H, s); 6.35(1H, t, J=6.75Hz, exchangeable with $CF_3COOD$); 7.06(4H, 3); 7.7(4H, s); 10.4(1H, s wide, exchangeable with $CF_3COOD$) |
| 54 | (4-I-phenyl) | $C_{21}H_{24}INO_4S$ (513.40) | 148–151 (toluene) | (DMSO $d_6$): 1.15–1.7(8H, m); 2.3–2.7 (4H, m); 3.45(2H, s); 4.05(1H, m, exchangeable with $CF_3COOD$); 7.0 (4H, s); 7.4–7.7(3H, m, 1H exchangeable with $CF_3COOD$); 7.8–8.0(2H, m) |
| 55 | (4-$CF_3$-phenyl) | $C_{22}H_{24}F_3NO_4S$ (455.491) | 138–140 (ethyl acetate-heptane) | 1.25–1.85(8H, m); 2.7(2H, s); 2.8(2H, d, J=6.75Hz, is converted into s with $CF_3COOD$); 3.55(2H, s); 6.5(1H, t, J=6.75Hz, exchangeable with $CF_3COOD$); 7.1 (4H, s); 7.5–8.25(5H, m, 1H exchangeable with $CF_3COOD$) |

[a]Percentage analysis: C, H, Br, Cl, F, I, N, S ± 0.35 except examples 52 et 53, S=+0.39 et S=+0.54

TABLE IIb

| Ex. No. | $R_1$ | Empirical formula[a] | M.P. (°C.) | NMR($\delta$, acetone $d_6$) |
|---|---|---|---|---|
| 56 | (3-$CF_3$-phenyl) | $C_{22}H_{24}F_3NO_4S$ (455.491) | 100–101 (ethyl acetate-heptane) | 1.35–1.75(8H, m); 2.7(2H, s); 2.8(2H, d, J=6.75Hz, is converted into s with $CF_3COOD$); 3.55(2H, s); 6.5(1H, t, J=6.75Hz, exchangeable with $CF_3COOD$; 7.1(4H, s); 7.75–8.26(4H, m); 10.0(1H, s wide, exchangeable with $CF_3COOD$) |

TABLE IIb-continued

| Ex. No. | R₁ | Empirical formula[a] | M.P. (°C.) | NMR(δ, acetone d₆) |
|---|---|---|---|---|
| 57 | 4-CN-phenyl | $C_{22}H_{24}N_2O_4S$ +¼ H₂O (417.012) | 155–158 (ethyl acetate-hexane) | (CDCl₃+DMSO d₆): 1.1–1.75(8H, m); 2.6 (2H, s); 2.6(2H, d, J=6.75Hz, is converted into s with CF₃COOD); 3.5(2H, s); 6.9–7.4 (5H, m, 1H exchangeable with CF₃COOD); 7.5–8.2(4H, m); 10.65(1H, s wide, exchangeable with CF₃COOD) |
| 58 | 3-NO₂-phenyl | $C_{21}H_{24}N_2O_6S$ +½ H₂O (441.50) | 123–128 (toluene) | (DMSO d₆): 1.1–1.7(8H, m); 2.4–2.7 (5H, m, 1H exchangeable with CF₃COOD); 3.45(2H, s); 7.0(4H, s); 7.5–8.7(6H, m, 2H exchangeable with CF₃COOD) |
| 59 | 2,4-diCl-phenyl | $C_{21}H_{23}Cl_2NO_4S$ (456.384) | 138–140 (ethyl acetate) | (CDCl₃): 1.0–1.75(8H, m); 2.5(2H, s); 2.5 (2H, d, J=6.75Hz, is converted into s with CF₃COOD); 3.5(2H, s); 4.95(1H, t, J=6.75Hz, exchangeable with CF₃COOD); 7.0(4H, s); 7.1–7.5(2H, m); 7.65–7.95 (1H, m); 8.9(1H, s wide, exchangeable with CF₃COOD) |

[a]Percentage analysis: C, H, Cl, F, N, S ± 0.27 except example 58, S= −0.43

TABLE IIc

| Ex. No. | R₁ | Empirical Formula[a] | M.P. (°C.) | NMR (δ, acetone d₆) |
|---|---|---|---|---|
| 60 | 4-isopropyl-phenyl | $C_{24}H_{31}NO_4S$ (429.575) | 141–144 (toluene) | (DMSO d₆): 1.1(6H, d, J=6.76Hz); 1.0–1.65(8H, m); 2.3–2.7(4H, m); 2.9(1H, dq, J=6.75Hz); 3.4(2H, s); 4.2(1H, m, exchangeable with CF₃COOD); 7.0(4H, s); 7.3–7.55(2H, m); 7.6–7.9(2H, m); 12.2 (1H, s wide, exchangeable with CF₃COOD) |
| 61 | 4-tert-butyl-phenyl | $CH_{25}H_{33}NO_4S$ (443.602) | 141–143 (ethyl acetate hexane) | (CDCl₃): 1.3(9H, s); 1.0–1.75(8H, m); 2.35–2.8(4H, m); 3.4(2H, s); 7.0(4H, s) 7.3–7.8(5H, m, 1H exchangeable with CF₃COOD); 12.1(1H, s wide, exchangeable with CF₃COOD) |
| 62 | 4-acetyl-phenyl | $C_{23}H_{27}NO_5S$ +0.3 H₂O (434.94) | 157.7–158 (ethyl acetate hexane) | (CDCl₃+DMSO d₆): 1.0–1.7(8H, m); 2.4–2.85(7H, m); 3.5(2H, s); 6.6 (1H, m, exchangeable with CF₃COOD); 7.0 (4H, s); 7.7–8.2(4H,m); 8.9(1H, s wide exchangeable with CF₃COOD) |
| 63 | 4-(methylsulfonyl)-phenyl | $C_{22}H_{27}NO_6S_2$ (465.59) | 176–177.5 (ethyl acetate) | (CDCl₃+DMSO d₆): 1.1–1.7(8H, m); 2.4–2.75(5H, m, 1H exchangeable with CF₃COOD); 3.1(3H, s); 3.45(2H, s); 7.0(4H, s); 7.3(1H, s wide exchangeable with CF₃COOD); 8.0(4H, s) |

[a]PERCENTAGE ANALYSIS: C, H, N, S±0.29

TABLE IId

| Ex. No. | R₁ | Empirical Formula[a] | M.P. (°C.) | NMR (δ, acetone d₆) |
|---|---|---|---|---|
| 64 | (4-trifluoromethoxyphenyl) | $C_{22}H_{24}F_3NO_5S$ (471.49) | 109–113 (ethyl acetate pentane) | 1.25–1.75(8H, m); 2.65(2H, s); 2.8(2H, d, J=6.75Hz, is converted into s with CF₃COOD); 3.55(2H, s); 6.4(1H, t, J=6.75Hz, exchangeable with CF₃COOD) 7.1(4H, s); 7.3–7.6(2H, m); 7.8–8.1 (2H, m); 9.95(1H, s wide exchangeable with CF₃COOD) |
| 65 | (4-methoxyphenyl) | $C_{22}H_{27}NO_5S$ (417.53) | 149–152 (ethyl acetate hexane) | 1.25–1.7(8H, m); 2.6(2H, s); 2.7(2H, d, J=6.75Hz, is converted into s with CF₃COOD); 3.5(2H, s); 3.8(3H, s); 6.1 (1H, t, J=6.75Hz, exchangeable with CF₃COOD); 6.8–7.2(2H, m); 7.0(4H, s); 7.5–7.9(2H, m); 9.5(1H, s wide, exchangeable with CF₃COOD) |
| 66 | (3-methylquinolinyl) | $C_{25}H_{28}N_2O_4S$ +¼ H₂O (457.07) | 219–221 (DMF-ethanol) | (DMSO d₆): 1.2–1.7(8H, m); 2.4–2.8 (7H, m); 3.5(2H, s); 7.0(4H, s); 7.4–8.4 (5H, m, 1H exchangeable with CF₃COOD); 8.95(1H, m); 12.2(1H, s wide exchangeable with CF₃COOD) |
| 67 | (2-thienyl) | $C_{19}H_{23}NO_4S_2$ (393.516) | 138–140 (ethanol acetate hexane) | (DMSO d₆): 1.0–1.7(8H, m); 2.4–2.85 (5H, m, 1H exchangeable with CF₃COOD); 3.45(2H, s); 6.75–7.2(4H, m); 7.4–8.0(3H, m); 12.2(1H, s wide exchangeable with CF₃COOD) |

[a]PERCENTAGE ANALYSIS: C, H, F, N, S±0.32

TABLE IIe

| Ex. No. | R₁ | Empirical Formula[a] | M.P. (°C.) | NMR (δ, acetone d₆) |
|---|---|---|---|---|
| 68 | (5-chloro-2-thienyl) | $C_{19}H_{22}ClNO_4S_2$ (427.961) | 136–138 (ethyl acetate hexane) | (DMSO d₆): 1.25–1.75(8H, m); 2.5–2.75 (4H, m); 3.45(2H, s); 7.0(4H, s); 7.15(1H, d, J=4.1Hz); 7.4(1H, d, J=4.1Hz); 7.9 (1H, t, J=6.75Hz, exchangeable with CF₃COOD); 12.05(1H, s, exchangeable with CF₃COOD) |
| 69 | (imidazolyl) | $C_{18}H_{23}N_3O_4S$ (377.459) | 176–178 (ethyl acetate hexane) | (DMSO d₆): 1.2–1.6(8H, m); 2.4–2.7 (4H, m); 3.1–3.4(1H, m, exchangeable with CF₃COOD) 3.45(2H, s); 7.0(4H, s); 7.45–7.9(3H, m, 1H exchangeable with CF₃COOD); 12.2(1H, s wide exchangeable with CF₃COOD) |
| 70 | (2-furyl) | $C_{19}H_{23}NO_5S$ (377.455) | 116 (ethyl acetate hexane) | (DMSO d₆); 1.0–1.75 (8H, m); 2.3–2.85 (5H, m, 1H exchangeable with CF₃COOD); 3.5(2H, s); 6.5–6.7(1H, m); 7.0(4H, s); 7.75–8.1(2H, m); 12.05(1H, s wide exchangeable with CF₃COOD) |

[a]PERCENTAGE ANALYSIS: C, H, Cl, N, S±0.26

EXAMPLE 71

4-[[1-[[[(4-Hydroxyphenyl)sulfonyl]amino]methyl]cyclopentyl]methyl]benzeneacetic acid A solution of 3.6 g (8.6 mmoles) of the compound prepared in example 65, in 40 ml of 1,2-dichloroethane is added dropwise to a mixture under nitrogen, of 10.7 g (34.2 mmoles) of the boron tribromide-dimethylsulfide complex and 40 ml of 1,2-dichloroethane. The reaction mixture is refluxed during 10 hours. An addition 10 g (32 mmoles) of the boron tribromide-dimethylsulfide complex is added, and the mixture is again refluxed during 7 hours. After cooling, the reaction mixture is poured into ice+water, and extracted with dichloromethane. The organic phase is washed with a solution of NaHCO₃, which is thereafter acidified with HCl, and extracted with CH₂Cl₂. The organic phase is dried over Na₂SO₄ and concentrated. The residue is purified by chromatography on a column of silica, in a dichloromethane-methanol (98:2 to 95:5) mixture, then by recrystallization in an ethyl acetate-toluene mixture, then in ethyl acetate to give 0.15 g (yield =4.3%) of an off-white powder. M.P. 132°-5° C.

| Percentage analysis: $C_{21}H_{25}NO_5S$ (MW = 403.492) | | | | |
|---|---|---|---|---|
| | C % | H % | N % | S % |
| Calculated | 62.51 | 6.25 | 3.47 | 7.95 |
| Found | 62.47 | 6.20 | 3.38 | 8.05 |

I.R. (KBr): $\nu$ (NH)=3280 cm$^{-1}$; (C=O)=1680 cm$^{-1}$; (SO$_2$)=1305 cm$^{-1}$; (SO$_2$)=1145 cm$^{-1}$. N.M.R. (DMSO d$_6$): $\delta$=1.1-1.6 (8H,m); 2.3-2.7 (4H,m); 3.1 (1H,m, exchangeable with CF$_3$COOD); 3.45 (2H,s); 4.0 1H,s wide, exchangeable with CF$_3$COOD); 6.7-7.2 (4H,m); 7.4-7.65 (4H,m); 11.0 (1H,s wide, exchangeable with CF$_3$COOD).

EXAMPLE 72

4-[[1-[[[(4-Chlorophenyl)sulfonyl]amino]methyl]cyclopropyl]methyl]benzeneacetic acid a) 1-(Phenylmethyl)cyclopropanecarbonitrile To a mixture under nitrogen of 26.3 g (260 mmoles) of diisopropylamine and 300 ml of tetrahydrofuran cooled to −75° C., there is added dropwise 125 ml (200 mmoles) of n-butyllithium in a 1.6M hexane solution, then 13.4 g (200 mmoles) of commercial cyclopropanecarbonitrile and finally 25.3 g (200 mmoles) of benzyl chloride. The reaction mixture is stirred 2 hours at −70° C. then 2 days at 20° C. 4 ml of water is added, before washing the reaction mixture with water saturated with NaCl. The organic phase dried over Na$_2$SO$_4$ is concentrated to give a brown liquid, which is purified by distillation. There is obtained 16.8 g (yield=53.5%) of a colorless liquid. b.p.$_{13}$=140°-8° C. A new distillation gives a colorless liquid. b.p.$_{0.3}$=64°-8° C.

| Percentage analysis: $C_{11}H_{11}N$ (MW = 157.215) | | | |
|---|---|---|---|
| | C % | H % | N % |
| Calculated | 84.04 | 7.05 | 8.91 |
| Found | 83.98 | 7.04 | 8.86 |

I.R. (film): $\nu$ (C≡N)=2230 cm$^{-1}$. N.M.R. (CDCl$_3$): $\delta$=0.7-1.0 (2H,m); 1.1-1.4 (2H,m); 2.7 (2H,s); 7.2 (5H,s).

b) [1-(Phenylmethyl)cyclopropyl]methanamine

Obtained by operating as in example 15a from 98 g (623 mmoles) of the compound prepared in example 72a, 28.4 g (740 mmoles) of LiAlH$_4$ in 800 ml ether. After distillation, there is obtained 82.3 g (yield=81.9%) of a colorless liquid. b.p.$_{0.3}$=75° C. (b.p.$_{0.3}$=62° C., according to Bumgardner C. L., J. Org. Chem. (1964) 29, 767-8).

| Percentage analysis: $C_{11}H_{15}N$ (MW = 161.246) | | | |
|---|---|---|---|
| | C % | H % | N % |
| Calculated | 81.94 | 9.38 | 8.69 |
| Found | 82.05 | 9.61 | 8.45 |

I.R. (film): $\nu$ (NH$_2$)=3360 cm$^{-1}$. N.M.R. (CDCl$_3$): $\delta$=0.25-0.5 (4H,m); 1.0 (2H,s, exchangeable with D$_2$O); 2.4 (2H,s); 2.65 (2H,s); 7.2 (5H,s).

c) 4-Chloro-N-[[1-(phenylmethyl)cyclopropyl]methyl]benzenesulfonamide

Obtained by operating as in example 1c, from 80.3 g (498 mmoles) of the compounds prepared in example 72b, 60.5 g (598 mmoles) of triethylamine, 105 g (497 mmoles) of 4-chlorobenzenesulfonyl chloride in 875 ml of dichloromethane. After recrystallization in an ethyl acetate-hexane mixture, there is obtained 145.8 g (yield=87.2%) of a white powder. M.P.=105.7-6.4° C.

| Percentage analysis: $C_{17}H_{18}ClNO_2S$ (MW = 335.848) | | | | | |
|---|---|---|---|---|---|
| | C % | H % | Cl % | N % | S % |
| Calculated | 60.80 | 5.40 | 10.56 | 4.17 | 9.55 |
| Found | 61.10 | 5.53 | 10.72 | 4.34 | 9.36 |

I.R. (KBr): $\nu$ (NH)=3220 cm$^{-1}$; (SO$_2$)=1315 cm$^{-1}$; (SO)=1145 cm$^{-1}$. N.M.R. ((CDCl$_3$): $\delta$=0.3-0.6 (4H,m); 2.6 (2H,s); 2.7 (2H,d, J=6 Hz, is converted into singulet with CF$_3$COOD); 4.9 (1H,t, J=6 Hz, exchangeable with CF$_3$COOD); 6.9-7.3 (5H,m); 7.3-7.5 (2H,m); 7.6-7.9 (2H,m).

d) N-[[1-[(4-Acetylphenyl)methyl]cyclopropyl]methyl]-4-chlorobenzenesulfonamide

Obtained by operating as in example 17b, from 10 g (29.7 mmoles) of the compound prepared in example 72c, 3.0 g of acetyl chloride (38.4 moles) and 19.8 g (148.5 mmoles) of aluminum chloride in 200 ml of 1,2-dichloroethane. After purification by chromatography on a column of silica with an ethyl acetate-hexane mixture, there is obtained 3 g (yield =23.2%) of a pasty solid.

I.R. (KBr): $\nu$ (NH)=3280 cm$^{-1}$; (C=O)=1870 cm$^{-1}$; (SO$_2$)=1155 cm$^{-1}$. N.M.R. (CDCl$_3$): $\delta$=0-0.1 (4H,m); 2.6 (3H,s); 2.65-2.8 (4H,m); 4.7 (1H,t, J=6.75 Hz, exchangeable with CF$_3$COOD); 6.7-8.0 (8H,m).

e) Methyl 4-[[1-[[[(4-chlorophenyl)sulfonyl]amino]methyl]cyclopropyl]methyl]benzeneacetate Obtained by operating as in example 5e, from 3 g (7.9 mmoles) of the compound prepared in example 72 d, 3.6 ml of methanol, 6.7 g (47.6 mmoles) of boron trifluoride etherate, 5.3 g (11.9 mmoles) of lead tetraacetate in 52 ml of dichloromethane. After purification by chromatography on a column of silica in a hexane-ethyl acetate mixture, there is obtained 1.5 g (yield=43.7 %) of a white solid. M.P.=97.2°-9.6° C.

I.R. (KBr): $\nu$ (NH)=3260 cm$^{-1}$; (C=O)=1710 cm$^{-1}$; (SO$_2$)=1315 cm$^{-1}$; (SO$_2$)=1155 cm$^{-1}$. N.M.R. (CDCl$_3$): $\delta$=0.25-0.5 (4H,m) 2.5 (2H,s); 2.7 (2H,d, J=6 Hz, is converted into singulet with CF$_3$COOD); 3.55 (2H,s); 3.65 (3H,s); 4.65 (1H,t, J=6 Hz, exchangeable with CF$_3$COOD); 6.75-7.2 (4H,m); 7.25-7.5 (2H,m); 7.5-7.8 (2H,m).

f) 4-[[1-[[[(4-Chlorophenyl)sulfonyl]amino]methyl]cyclopropyl]methyl]benzeneacetic acid A mixture of 1.4 g (3.4 mmoles) of the ester prepared in example 72e, 22 ml of methanol, 0.38 g (9.5 mmoles) of NaOH pellets and 22 ml of water, is refluxed 1.5 hour. After cooling, concentration to dryness and capture with water, the mixture is washed with ether and the aqueous phase is acidified with HCl. The white precipitate formed is washed with water, then dried under vacuum at 80° C. The solid obtained is purified by recrystallization in an ethyl acetate-hexane mixture to give 0.7 g (yield=51.8%) of a white powder. M.P.=160.3°-2.4° C.

| Percentage analysis: C₁₉H₂₀ClNO₄S (MW = 393.885) | | | | | |
|---|---|---|---|---|---|
| | C % | H % | Cl % | N % | S % |
| Calculated | 57.94 | 5.12 | 9.00 | 3.56 | 8.14 |
| Found | 58.07 | 4.96 | 8.74 | 3.69 | 7.74 |

I.R. (KBr): $\nu$ (NH)=3250 cm$^{-1}$; (C=O)=1695 cm$^{-1}$; (SO₂)=1315 cm$^{-1}$; (SO₂)=1145 cm$^{-1}$. N.M.R. (acetone d₆): $\delta$=0.4–0.6 (4H,m); 2.65 (2H,s); 2.75 (2H,d, J=6Hz, is converted into singulet with CF₃COOD); 3.6 (2H,s); 6.55 (1H,t, J=6 Hz, exchangeable with CF₃COOD); 6.9–7.2 (4H,m); 7.4–7.9 (4H,m); 10.5 (1H,s wide, exchangeable with CF₃COOD).

EXAMPLE 73

4-[[1-[[[(4-Chlorophenyl]sulfonyl]amino]methyl]cycloheptyl]methyl]benzeneacetic acid a) 1-(Phenylmethyl)cycloheptanecarbonitrile Obtained by operating as in example 27b, from 195 mmoles of lithiated diisopropylamine (25.6 g (252.9 mmoles) of diisopropylamine treated with 122 ml (195 mmoles) of n-butyllithium 1.6M in hexane) in 300 ml of dry tetrahydrofuran, 24 g (195 mmoles) of commercial cycloheptanecarbonitrile and 24.6 g (195 mmoles) of benzyl chloride. After distillation, there is obtained 23.2 g (yield=55.8%) of a yellow viscous liquid. b.p.$_{16}$=190°–7° C.

I.R. (film): $\nu$ (C≡N)=2225 cm$^{-1}$. N.M.R. (CDCl₃): $\delta$=1.25–2.25 (12H,m); 2.75 (2H,s); 7.2 (5H,s).

b) 1-[(4-Acetylphenyl)methyl]cycloheptanecarbonitrile

Obtained by operating as in example 32a, from 23 g (107.8 mmoles) of the compound prepared as in example 73a, 17 g (216.5 mmoles) of acetyl chloride and 43.1 g (323.2 mmoles) of aluminum chloride, in 500 ml of dichloromethane. After distillation, there is obtained 17.5 g (yield=63.6%) of a very thick pale yellow oil. b.p.$_{0.55}$=178° C.

I.R. (film): $\nu$ (C≡N) 2220 cm$^{-1}$; (C=O)=1670 cm$^{-1}$. N.M.R. (CDCl₃): $\delta$=1.25–2.25 (12H,m); 2.5 (3H,s); 2.8 (2H,s); 7.15–7.5 (2H,m); 7.7–8.0 (2H,m) .

c) 1-[[4-(2,5,5-Trimethyl-1,3-dioxan-2-yl)phenyl]methyl]cycloheptanecarbonitrile A mixture of 5 g (19.6 mmoles) of the compound prepared in example 73b, 3.3 g (31.7 mmoles) of 2,2-dimethyl-l,3-propanediol, 0.1 g (0.6 mmoles) of para-toluenesulfonic acid and 20 ml of toluene, is refluxed 8 hours in a balloon flask over which there is a separator called "Dean-Stark" enabling to remove the water formed during the reaction. After concentration to dryness, the reaction mixture is captured with CH₂Cl₂, washed with H₂O and dried over Na₂SO₄. After concentration, there is obtained 5.6 g (yield=83.8%) of a clear brown oil, which slowly crystallizes, and which is used without other purification.

I.R. (film): $\nu$ (C≡N)=2225 cm$^{-1}$. N.M.R. (CDCl₃): $\delta$=0.6 (3H,s); 1.25 (3H,s); 1.5 (3H,s); 1.4–2.4 (12H,m); 2.8 (2H,s); 3.4 (4H,s); 7.3 (4H,s).

d) 1-[[4-(2,5,5-Trimethyl-1,3-dioxan-2-yl)phenyl]methyl]cycloheptanemethanamine

Obtained by operating as in example 15a, from 5.5 g (16.1 mmoles) of the compound prepared in example 73c, 0.73 g (19.2 mmoles) of LiAlH₄ in 70 ml of anhydrous ether. There is obtained 4.9 g (yield=88.1%) of an orange color oil used without other purification.

I.R. (film): $\nu$ (NH₂)=3360 cm$^{-1}$. N.M.R. (CDCl₃): $\delta$=0.6 (3H,s); 1.3 (3H,s); 1.2–1.9 (17H,m, 2H exchangeable with D₂O); 2.4 (2H,s); 2.6 (2H,s); 3.4 (4H,s); 6.9–7.6 (4H,m).

e) 4-Chloro-N-[[1-[[4-(2,5,5-trimethyl-1,3-dioxan-2-yl)phenyl]methyl]cycloheptyl]methyl]-benzenesulfonamide Obtained by operating as in example 1c, from 4.8 g (13.9 mmoles) of the compound prepared in example 73d, 1.7 g (16.8 mmoles) of triethylamine, 2.9 g (13.7 mmoles) of 4-chlorobenzenesulfonyl chloride in 25 ml of dry dichloromethane. After stirring 23 hours at room temperature, the usual treatment and purification by chromatography on a column of silica with an ethyl acetate-hexane mixture (4:1), there is obtained 4.4 g (yield=61.7%) of a pasty solid.

I.R. (KBr): $\nu$ (NH)=3270 cm$^{-1}$; (SO₂)=1320 cm$^{-1}$; (SO₂)=1155 cm$^{-1}$. N.M.R. (CDCl₃): $\delta$=0.8 (3H,s); 1.2 (3H,s); 1.1–1.8 (15H,m); 2.5 (2H,s); 2.6 (2H,d, J=6.75 Hz, is converted into singulet with CF₃COOD); 3.3 (4H,s); 4.3 (1H,t, J=6.75 Hz, exchangeable with CF₃COOD); 6.8–7.9 (8H,m).

f) N-[[1-[(4-Acetylphenyl)methyl]cycloheptyl]methyl]-4-chlorobenzenesulfonamide

A mixture of 1 g (1.9 mmoles) of the compound prepared in example 73e, 1.5 ml HCl 10.7N, 0.9 ml water and 5ml isopropanol, is refluxed during 4 hours. After cooling and concentration to dryness, the residue is captured with water and extracted with dichloromethane. The organic phase, dried over Na₂SO₄ is concentrated and purified by chromatography on a column of silica in an ethyl acetate-hexane (5:1) mixture to give 0.6 g (yield=72.3%) of a pasty white solid.

I.R. (KBr): $\nu$ (NH)=3270 cm$^{-1}$; (C=O) = 1660 cm$^{-1}$; (SO₂)=1315 cm$^{-1}$; (SO₂)=1175 cm$^{-1}$. N.M.R. (CDCl₃): $\delta$=1.0–1.6 (12H,m); 2.5 (3H,s); 2.6 (2H,s); 2.65 (2H,d, J=6.75 Hz, is converted into singulet with CF₃COOD); 4.9 (1H,t, J=6.75 Hz, exchangeable with CF₃COOD); 7.0–7.25 (2H,m); 7.3–7.6 (2H,m); 7.65–7.9 (4H,m).

g) Methyl 4-[[1-[[[(4-chlorophenyl)sulfonyl]amino]methyl]cycloheptyl]methyl]benzeneacetate Obtained by operating as in example 5e, from 2.2 g (5.1 mmoles) of the compound prepared in example 73f, 2.3 ml of methanol, 4.3 g (30 mmoles) of boron trifluoride etherate, 3.4 g (7.7 mmoles) of lead tetraacetate in 50 ml of dry dichloromethane. There is obtained 2.2 g (yield=93.6%) of a white solid used without other purification. M.P.=158.1°–60.9° C.

I.R. (KBr): $\nu$ (NH)=3250 cm$^{-1}$; (C=O)=1705 cm$^{-1}$; (SO₂)=1345 cm$^{-1}$; (SO₂)=1155 cm$^{-1}$. N.M.R. (CDCl₃): $\delta$=1.2–1.6 (12H,m); 2.5 (2H,s); 2.7 (2H,d, J=6.75 Hz, is converted into singulet with CF₃COOD); 3.6 (2H,s); 3.7 (3H,s); 4.45 (1H,t, J=6.75 Hz, exchangeable with CF₃COOD); 6.8–7.3 (4H,m); 7.35–7.6 (2H,m); 7.65–7.9 (2H,m).

h) 4-[[1-[[[(4-Chlorophenyl)sulfonyl]amino]methyl]cycloheptyl]methyl]benzeneacetic acid Obtained by operating as in example 72f, from 2 g (4.3 mmoles) of the compound prepared in example 73g, 8 ml of methanol, 0.48 g (12 mmoles) of sodium hydroxide pellets and 28 ml water. After 2 recrystallizations in an ethyl acetate-hexane mixture, there is obtained 0.3 g (yield=15.5%) of a white powder. M.P.=127.8°–9.6° C.

| Percentage analysis: C₂₃H₂₈ClNO₄S (MW = 449.992) | | | | | |
|---|---|---|---|---|---|
| | C % | H % | Cl % | N % | S % |
| Calculated | 61.39 | 6.27 | 7.88 | 3.11 | 7.12 |

-continued

Percentage analysis: $C_{23}H_{28}ClNO_4S$ (MW = 449.992)

|  | C % | H % | Cl % | N % | S % |
|---|---|---|---|---|---|
| Found | 61.70 | 6.27 | 7.94 | 3.16 | 6.98 |

I.R. (KBr): $\nu$ (NH)=3210 ; (C=O)=1690 cm$^{-1}$; (SO$_2$)=1315 cm$^{-1}$;(SO$_2$)=1150 cm$^{-1}$. N.M.R. (aceton d$_6$): $\delta$=1.25–1.6 (12H,m); 2.6 (2H,s); 2.7 (2H,d, J=6.75 Hz, is converted into singulet with CF$_3$COOD); 3.55 (2H,s); 6.3 (1H,t, J=6.75 Hz, exchangeable with CF$_3$COOD); 7.1 (4H,s); 7.4–7.9 (4H,m); 10.25 (1H,s wide, exchangeable with CF$_3$COOD).

EXAMPLE 74

4-Chloro-N-[[1-[[4-[2-(morpholin-4-yl)-2-oxoethyl]-phenyl]methyl]cyclopentyl]methyl]benzenesulfonamide a) 4-[[1-[[[(4-Chlorophenyl)sulfonyl]amino]methyl]cyclopentyl]methyl]benzeneacetyl chloride A mixture of 17.1 g (40.5 mmoles) of the compound prepared in example 19 and 171 ml (2360 mmoles) of thionyl chloride is refluxed during 4 hours. After cooling and concentration, the yellow solid obtained is washed with heptane and squeezed to give 17.0 g (yield=95.3%) of a yellow solid used without other purification. M.P.=90°–5° C.

I.R. (KBr): $\nu$ (NH)=3270 cm$^{-1}$; (C=O)=1775 cm$^{-1}$; (SO$_2$)=1325 cm$^{-1}$; (SO)=1155 cm$^{-1}$. N.M.R. (CDCl$_3$): $\delta$=1.15–1.9 (8H,m); 2.6 (2H,s); 2.6–2.9 (2H,m, is converted into singulet with CF$_3$COOD); 4.1 (2H,s); 4.8 (1H,m, exchangeable with CF$_3$COOD); 7.1 (4H,s); 7.3–7.6 (2H,m); 7.65–8.0 (2H,m).

b) 4-Chloro-N-[[1-[[4-[2-(morpholin-4-yl)-2-oxoethyl]-phenyl]methyl]cyclopentyl]methyl]benzenesulfonamide A solution of 2.7 g (6.1 mmoles) of the compound prepared in example 74a in 27 ml of dichloromethane is added dropwise to a solution consisting of 1.6 g (18.3 mmoles) of morpholine and 160 ml of dichloromethane. After stirring 22 hours at room temperature, the reaction mixture is poured over a mixture of water and HCl and extracted with dichloromethane. The organic phase, washed with water and dried over Na$_2$SO$_4$ is concentrated under vacuum. The residue is recrystallized in an ethyl acetate-hexane mixture to give 0.7 g (yield=23.3%) of a white solid. M.P.=157°–9° C.

Percentage analysis: $C_{25}H_{31}ClN_2O_4S$ (MW = 491.046)

|  | C % | H % | Cl % | N % | S % |
|---|---|---|---|---|---|
| Calculated | 61.15 | 6.36 | 7.22 | 5.70 | 6.53 |
| Found | 61.35 | 6.50 | 7.25 | 5.79 | 6.90 |

I.R. (KBr): $\nu$ (NH)=3160 cm$^{-1}$; (C=O)=1630 cm$^{-1}$; (SO$_2$)=1325 cm$^{-1}$; (SO$_2$)=1160 cm$^{-1}$. N.M.R. (CDCl$_3$): $\delta$=1.15–1.75 (8H,m); 2.55 (2H,s); 2.65 (2H,d, J=6.75 Hz, is converted into singulet with CF$_3$COOD); 3.25–3.75 (10H,m); 4.5 (1H,t, J=6.75 Hz, exchangeable with CF$_3$COOD); 7.0 (4H,s); 7.25–7.5 (2H,m); 7.6–7.8 (2H,m).

EXAMPLE 75

4-[[1-[[[(4-Chlorophenyl)sulfonyl]amino]methyl]cyclopentyl]methyl]benzeneacetamide A mixture of 3.1 g (7.1 mmoles) of the acid chloride prepared in example 74a and 70 ml of an aqueous solution of ammonium hydroxide at 22% (d=0.91) is stirred 3 days at room temperature. The precipitate formed is filtered, washed with water and dried at 50° C. After 2 recrystallizations in ethyl acetate, there is obtained 1.0 g (yield=33.3%) of a white solid. M.P.=151°–3° C.

Percentage analysis: $C_{21}H_{25}ClN_2O_3S$ (MW = 420.95)

|  | C % | H % | Cl % | N % | S % |
|---|---|---|---|---|---|
| Calculated | 59.92 | 5.99 | 8.42 | 6.65 | 7.62 |
| Found | 59.62 | 5.96 | 8.38 | 6.67 | 7.58 |

I.R. (KBr): $\nu$ (NH$_2$)=3440 cm$^{-1}$; (NH)=3190 cm$^{-1}$; (C=O)=1660 cm$^{-1}$; (SO$_2$)=1320 cm$^{-1}$; (SO$_2$)=1160 cm$^{-1}$. N.M.R. (CDCl$_3$+DMSO d$_6$): $\delta$=1.25–1.8 (8H,m); 2.5–2.8 (4H,m); 3.45 (2H,s); 6.4 (1H,t, J=6.75 Hz, exchangeable with CF$_3$COOD); 6.5–7.0 (2H,s wide, exchangeable with CF$_3$COOD); 7.1 (4H,s); 7.35–7.55 (2H,m); 7.6–7.9 (2H,m).

EXAMPLE 76

3-[[2-[4-[[1-[[[(4-Chlorophenyl)sulfonyl]amino]methyl]-cyclopentyl]methyl]phenyl]-1-oxoethyl]amino]-propanoic acid a) Ethyl 3-[[2-[4-[[1-[[[(4-Chlorophenyl)sulfonyl]amino]methyl]cyclopentyl]methyl]phenyl]-1-oxoethyl]amino]propanoate 6.6 g (15 mmoles) of the acid chloride prepared in example 74a dissolved in 80 ml of dichloromethane is poured over a mixture of 2.4 g (15 mmoles) of commercial ethyl 3-aminopropanoate chlorhydrate, 3.3 g (33 mmoles) of triethylamine and 150 ml of dichloromethane. After stirring 24 hours at room temperature, the reaction mixture is added to a mixture of water-HCl. The organic phase is decanted, washed with a diluted HCl solution, then with a solution of NaHCO$_3$ and water before drying over Na$_2$SO$_4$. After concentration, the residue obtained is purified by chromatography on a column of silica with an ethyl acetate-hexane (2:1) mixture to give 3.0 g (yield=38.4%) of an off-white solid. M.P.=128°–30° C.

I.R. (KBr): $\nu$ (NH)=3375 cm$^{-1}$; (NH)=3200 cm$^{-1}$; (C=O)=1720 cm$^{-1}$; (C=O)1650 cm$^{-1}$; (SO$_2$)=1320 cm$^{-1}$; (SO$_2$)=1160 cm$^{-1}$. N.M.R. (CDCl$_3$): $\delta$=1.2 (3H,t, J=6.75 Hz); 1.35–1.8 (8H,m); 2.5 (2H,t, J=6.75 Hz); 2.6 (2H,s); 2.75 (2H,d, J=6.75 Hz, is converted into singulet with CF$_3$COOD); 3.4 (2H,t, J=6.75 Hz); 3.5 (2H,s); 4.1 (2H,q, J=6.75 Hz); 4.7 (1H,t, J= 6.75 Hz, exchangeable with CF$_3$COOD); 6.0 (1H,s wide, exchangeable with CF$_3$COOD); 7.1 (4H,s); 7.35–7.6 (2H,m); 7.7–7.9 (2H,m).

b) 3-[[2-[4-[[1-[[[(4-Chlorophenyl)sulfonyl]amino]methyl]cyclopentyl]methyl]phenyl]-1-oxoethyl]amino]-propanoic acid Obtained by operating as in example 5f, from 3.0 g (5.75 mmoles) of the compound prepared in example 76a, 0.65 g (11.5 mmoles) of KOH pellets, 30 ml ethanol and 30 ml water. After 2 recrystallizations in ethyl acetate, there is obtained 1.7 g (yield=60.7%) of a white solid. M.P.=148°–50° C.

Percentage analysis: $C_{24}H_{29}ClN_2O_5S$ (MW = 493.018)

|  | C % | H % | Cl % | N % | S % |
|---|---|---|---|---|---|
| Calculated | 58.47 | 5.93 | 7.19 | 5.68 | 6.50 |
| Found | 58.22 | 5.91 | 7.30 | 5.64 | 6.58 |

I.R. (KBr): ν (NH)=3400 cm⁻¹;(NH)=3240 cm⁻¹; (C=O)=1705 cm⁻¹; (C=O)=1610 cm⁻¹; (SO₂)=1325 cm⁻¹; (SO₂)=1160 cm⁻¹. N.M.R. (DMSO d₆): δ=1.1–1.8 (8H,m); 2.25–2.9 (6H,m); 3.2 (2H,t, J=6.75 Hz); 3.3 (2H,s); 7.1 (4H,s); 7.5–8.5 (6H,m, 2H exchangeable with CF₃COOD) 12.2 (1H,s, exchangeable with CF₃COOD).

EXAMPLE 77

Ethyl 4-[[1-[[[(4-chlorophenyl)sulfonyl]amino]methyl]cyclopentyl]methyl]benzeneacetate A mixture of 4.4 g (10 mmoles) of the acid chloride prepared in example 74a, 1.2 g (12 mmoles) of triethylamine in 50 ml of absolute ethanol, is stirred 16 hours at room temperature, before being concentrated to dryness, captured with water and extracted with ether. The organic phase is washed with water, then with a solution of NaHCO₃, before drying over Na₂SO₄ and concentrated. The residue is purified by chromatography on a column of silica with a hexane-ethyl acetate mixture (1:1), then is recrystallized in a hexane-ethyl acetate mixture to give 0.1 g (yield=2.2%) of a white solid. M.P.=117°–9° C.

| Percentage analysis: $C_{23}H_{28}ClNO_4S$ (MW = 449.993) | | | | | |
|---|---|---|---|---|---|
| | C % | H % | Cl % | N % | S % |
| Calculated | 61.39 | 6.27 | 7.88 | 3.11 | 7.12 |
| Found | 61.30 | 6.27 | 7.90 | 3.27 | 7.16 |

I.R. (KBr): ν (NH)=3250 cm⁻¹; (C=O)=1700 cm⁻¹; (SO₂)=1320 cm⁻¹; (SO₂)=1155 cm⁻¹. N.M.R. (CDCl₃): δ=1.25 (3H,t, J=6.75 Hz); 1.3–1.8 (8H,m); 2.55 (2H,s); 2.7 (2H,d, J=6.75 Hz, is converted into singulet with CF₃COOD); 3.55 (2H,s); 4.15 (2H,q, J=6.75 Hz); 4.7 (1H,t, J=6.75 Hz, exchangeable with CF₃COOD); 6.8–7.25 (4H,m); 7.3–7.5 (2H,m); 7.6–7.85 (2H,m).

EXAMPLE 78

Ethyl 4-[[1-[[[(4-chlorophenyl)sulfonyl]amino]methyl]cyclopentyl]methyl]benzeneacetate A solution of 2.1 g (5 mmoles) of the acid prepared in example 19, in 210 ml absolute ethanol, is saturated with HCl gas, then refluxed 5 hours. After cooling and concentration to dryness, the while solid obtained is captured with ether, washed with water, dried over Na₂SO₄ and concentrated. After 2 recrystallizations in a hexane-ethyl acetate mixture, there is obtained 1.4 g (yield=62.2%) of a white solid, whose spectral properties are identical to those of the product obtained in example 77. M.P.=117°–9° C.

EXAMPLE 79

2-(Diethylamino)ethyl 4-[[1-[[[(4-Chlorophenyl)sulfonyl]amino]methyl]cyclopentyl]methyl]benzeneacetate To a suspension consisting of 4.4 g (10 mmoles) of the compound prepared in example 20, in 200 ml isopropanol, there is added 1.4 g (10.3 mmoles) of commercial (2-chloroethyl)-diethylamine. The mixture is refluxed 4 hours. After cooling and filtration of an insoluble product, the reaction mixture is concentrated. The residue which is captured with ether is washed with water, dried over Na₂SO₄ and concentrated. The oil obtained is recrystallized in hexane to give 0.4 g (yield=7.7%) of a white solid. M.P.=80°–1° C.

| Percentage analysis: $C_{27}H_{37}ClN_2O_4S$ (MW = 521.116) | | | | | |
|---|---|---|---|---|---|
| | C % | H % | Cl % | N % | S % |
| Calculated | 62.23 | 7.16 | 6.80 | 5.38 | 6.15 |
| Found | 62.08 | 7.32 | 6.80 | 5.27 | 5.84 |

I.R. (KBr): ν (NH)=3250 cm⁻¹; (C=O)=1690 cm⁻¹; (SO₂)=1335 cm⁻¹; (SO₂)=1150 cm⁻¹. N.M.R. (CDCl₃): δ=0.95 (6H,t, J=7.5 Hz); 1.2–1.75 (8H,m); 2.5 (2H,s); 2.6 (2H,d, J=6.75 Hz, is converted into singulet with CF₃COOD); 2.6 (6H,m); 3.55 (2H,s); 4.1 (2H,t, J=6.0 Jz); 4.75 (1H,t, J=6.75 Hz, exchangeable with CF₃COOD); 6.8–7.3 (4H,m); 7.35–7.55 (2H,m); 7.6–7.9 (2H,m).

EXAMPLE 80

4-[[1-[[[(4-Chlorophenyl)sulfonyl]amino]methyl]cyclopentyl]methyl]benzenemethanesulfonic acid a) 4-Chloro-N-[[1-[[4-(chloromethyl)phenyl]methyl]cyclopentyl]methyl]benzenesulfonamide To a mixture maintained under nitrogen, containing 46.7 g (118.5 mmoles) of the alcohol prepared in example 25f, 9.1 g (115.5 mmoles) of pyridine dried over KOH, and 467 ml of dry dichloromethane, there is added dropwise during 3 hours, a solution consisting of 33 ml (452.4 mmoles) of thionyl chloride and 230 ml of dry dichloromethane. After stirring 2 hours at room temperature, the reaction mixture is slowly poured into an aqueous solution of NaHCO₃ under strong stirring. The extraction is carried out by dichloromethane, which is thereafter washed with a diluted solution of HCl, then with water and dried over Na₂SO₄, before being concentrated. The residue is purified by chromatography on a column of silica then by recrystallization in an ethyl acetate-hexane mixture to give 33.5 g (yield=68.7%) of a white powder. M.P.=124°–6° C.

I.R. (KBr): ν (NH)=3270 cm⁻¹; (SO₂)=1315 cm⁻¹; (SO₂)=1155 cm⁻¹. N.M.R. (CDCl₃): δ=1.25–1.8 (8H,m); 2.6 (2H,s); 2.7 (2H,d, J=6.75 Hz, is converted into singulet with CF₃COOD); 4.5 (3H,m, 1H exchangeable with CF₃COOD); 6.9–7.3 (4H,m); 7.3–7.55 (2H,m); 7.6–7.9 (2H,m).

b) 4-[[1-[[[(4-Chlorophenyl)sulfonyl]amino]methyl]cyclopentyl]methyl]benzenemethanesulfonic acid To a solution of 5 g (12 mmoles) of the compound prepared in example 80a, 45 ml water and 125 ml acetone, refluxed, there is added dropwise a solution consisting of 1.5 g of sodium sulfite and 45 ml water. Reflux is maintained for 7 hours after the end of the addition. After cooling, the reaction mixture is acidified with 70 ml 4N HCl and refluxed 1¼ hour. After cooling and dilution with 100 ml water, an insoluble product is removed. The filtrate, concentrated to dryness, is captured with a ethanol to remove an insoluble product. The ethanol filtrate is concentrated and purified by chromatography on a column of silica with a dichloromethane-ethanol (95:5) mixture, then by recrystallization in isopropanol to give 1.1 g (yield=20.0%) of a white powder. M.P.=200°–30° C.

| Percentage analysis: $C_{20}H_{24}ClNO_5S_2$ + 1.1 $H_2O$ (MW = 477.812) | | | | | |
|---|---|---|---|---|---|
| | C % | H % | Cl % | N % | S % |
| Calculated | 50.27 | 5.53 | 7.42 | 2.93 | 13.42 |

| Percentage analysis: $C_{20}H_{24}ClNO_5S_2$ + 1.1 $H_2O$ (MW = 477.812) | | | | | |
|---|---|---|---|---|---|
| | C % | H % | Cl % | N % | S % |
| Found | 50.63 | 5.15 | 7.17 | 2.73 | 12.98 |

I.R. (KBr): $\nu$ (NH)=3280 cm$^{-1}$; (SO$_2$)=1330 cm$^{-1}$; (SO$_2$)=1150 cm$^{-1}$. N.M.R. (CDCl$_3$+DMSO d$_6$): $\delta$=1.25-1.75 (8H,m); 2.3-2.8 (4H,m); 3.9 (2H,s); 6.8-7.6 (8H,m, 2H exchangeable with CF$_3$COOD); 7.6-7.8 (2H,m).

EXAMPLE 81

4-Chloro-N-[1-[[[4-[(1H-tetrazol-5-yl)methyl]phenyl]methyl]cyclopentyl]methyl]benzenesulfonamide a) 4-Chloro-N-[[1-[[4-(cyanomethyl)phenyl]methyl]cyclopentyl]methyl]benzenesulfonamide A mixture maintained under nitrogen, consisting of 8.0 g (19.4 mmoles) of the compound prepared in example 80a, 1.45 g (29 mmoles) of sodium cyanide and 50 ml ethanol 96°, is refluxed 3½ hours. After concentration to dryness, and capture with water, the mixture is extracted with CH$_2$Cl$_2$. The organic phase is washed with water saturated with NaCl, dried over Na$_2$SO$_4$ and concentrated. The residue is recrystallized in an ethyl acetate-hexane mixture to give 4.2 g (yield=53.8%) of an off-white solid. M.P.=128°-31° C. A portion of this solid which is purified by chromatography on a column of silica in an ethyl acetate-hexane (1:3) mixture gives a white powder. M.P.=134.2°-4.9° C.

| Percentage analysis: $C_{21}H_{23}ClN_2O_2S$ (MW = 402.94) | | | | |
|---|---|---|---|---|
| | C % | H % | Cl % | N % | S % |
| Calculated | 62.60 | 5.75 | 8.80 | 6.95 | 7.96 |
| Found | 62.55 | 5.71 | 8.86 | 7.05 | 7.90 |

I.R. (KBr): $\nu$ (NH)=3260 cm$^{-1}$; (C≡N)=2260 cm$^{-1}$; (SO$_2$)=1320 cm$^{-1}$; (SO$_2$)=1150 cm$^{-1}$. N.M.R. (CDCl$_3$): $\delta$=1.0-1.9 (8H,m); 2.6 (2H,s); 2.7 (2H,d, J=6.0 Hz, is converted into singulet with CF$_3$COOD); 3.65 (2H,s); 5.0 (1H,t, J=6.0 Hz, exchangeable with CF$_3$COOD); 7.0 (4H,s); 7.25-7.55 (2H,m); 7.6-7.9 (2H,m).

b) 4-Chloro-N-[1-[[[4-[(1H-tetrazol-5-yl)methyl]phenyl]methyl]cyclopentyl]methyl]benzenesulfonamide A mixture under nitrogen, consisting of 4.1 g (10.1 mmoles) of the compound prepared in example 81a, 2.0 g (30.8 mmoles) of sodium azide, 2.15 g (15.6 mmoles) of triethylamine chlorohydrate and 100 ml of 1-methylpyrrolidin-2-one dried on molecular sieves, is heated 8 hours at 150° C. After cooling, the reaction mixture is concentrated to dryness, captured with a solution of NaOH 2H, washed with ether before being acidified with HCl 5N. The pasty precipitate formed is captured with ethyl acetate, washed with water saturated with NaCl and dried over Na$_2$SO$_4$. After concentration, the residue obtained is purified by chromatography on a column of silica in a dichloromethane-methanol (98:2) mixture. The head fractions give a beige solid, which after 2 recrystallizations in ethanol gives 1.0 g (yield=22.2%) of white powder. M.P.=183°-5° C.

| Percentage analysis: $C_{21}H_{24}ClN_5O_2S$ + ¼ $H_2O$ (MW = 450.47) | | | | | |
|---|---|---|---|---|---|
| | C % | H % | Cl % | N % | S % |
| Calculated | 55.99 | 5.48 | 7.87 | 15.55 | 7.11 |
| Found | 56.03 | 5.67 | 7.91 | 15.52 | 7.26 |

I.R. (KBr): $\nu$ (NH)=3305 cm$^{-1}$; (SO$_2$)=1300 cm$^{-1}$; (SO$_2$)=1145 cm$^{-1}$. N.M.R. (DMSO d$_6$): $\delta$=1.25-1.65 (8H,m); 2.4-2.7 (5H,m, 1H exchangeable with CF$_3$COOD); 4.2 (2H,s); 7.0 (4H,s); 7.3-7.95 (5H,m, 1H exchangeable with CF$_3$COOD).

EXAMPLE 82

4-Amino-N-[1-[[[4-[(1H-tetrazol-5-yl)methyl]phenyl]methyl]cyclopentyl]methyl]benzenesulfonamide Formed during the reaction to give the compound of example 81b and isolated during the chromatographic purification of this compound. A second chromatography on a column of silica in a dichloromethane-methanol (98:2) mixture followed recrystallization in ethanol gives 0.1 g (yield=2.3%) of a white powder. M.P.=204°-5° C.

| Percentage analysis: $C_{21}H_{26}N_6O_2S$ (MW = 426.539) | | | | |
|---|---|---|---|---|
| | C % | H % | N % | S % |
| Calculated | 59.13 | 6.14 | 19.70 | 7.52 |
| Found | 59.18 | 6.04 | 19.75 | 7.35 |

I.R. (KBr): $\nu$ (NH$_2$)=3460 cm$^{-1}$; (NH$_2$)=3360 cm$^{-1}$; (NH)=3260 cm$^{-1}$; (SO$_2$)=1300 cm$^{-1}$; (SO$_2$)=1145 cm$^{-1}$. N.M.R. (acetone d$_6$+DMSO d$_6$): $\delta$=1.3-1.6 (8H,m); 2.4-2.7 (5H,m, 1H exchangeable with CF$_3$COOD); 4.2 (2H,s); 6.45-6.8 (4H,m, 2H exchangeable with CF$_3$COOD); 7.1 (4H,s); 7.25-7.65 (3H, 1H exchangeable with CF$_3$COOD).

EXAMPLE 83

[[4-[[1-[[[(4-Chlorophenyl)sulfonyl]amino]methyl]cyclopentyl]methyl]phenyl]methyl]phosphonic acid a) Diethyl [[4-[[1-[[[(4-Chlorophenyl)sulfonyl]amino]methyl]cyclopentyl]methyl]phenyl]methyl]phosphonate A mixture under nitrogen of 5 g (12.1 mmoles) of the compound prepared in example 80a and 32 ml of triethylphosphite is heated 5 hours at 140° C. After cooling, the precipitate formed is filtered, and after washing with ether and drying in air gives 4.8 g (yield=77.2%) of a white powder which is used without other purification. M.P.=127°-32° C.

I.R. (KBr): $\nu$ (NH)=3140 cm$^{-1}$; (SO$_2$)=1330 cm$^{-1}$; (SO$_2$)=1165 cm$^{-1}$. N.M.R. (CDCl$_3$): $\delta$=1.25 (6H,t, J=6.75 Hz); 1.3-1.75 (8H,m); 2.6 (2H,s); 2.7 (2H,d, J=6.75 Hz, is converted into singulet with CF$_3$COOD); 3.1 (2H,d, J=21.75 Hz); 4.0 (4H,dq, J$_1$=6.75 Hz, J$_2$=6.75 Hz); 5.2 (1H,t, J=6.75 Hz, exchangeable with CF$_3$COOD); 6.8-7.3 (4H,m); 7.3-7.6 (2H,m); 7.65-7.95 (2H,m).

b) [[4-[[1-[[[(4-Chlorophenyl)sulfonyl]amino]methyl]cyclopentyl]methyl]phenyl]methyl]phosphonic acid A mixture of 4.8 g (9.3 mmoles) of the compound prepared in example 83a, 9 ml of 10.7N HCl and 6 ml of acetic acid, is refluxed 2 hours. After cooling, the mixture is diluted with 25 ml water, before extracting it with dichloromethane. The organic phase dried over Na$_2$SO$_4$ and concentrated, gives a pasty residue, which is purified by column chromatography in dichloromethane-methanol (9:1) mixture. There is essentially obtained a monoesterified compound, which is treated again in the same conditions (HCl 10.7N, acetic acid), under reflux during 10 hours. After cooling, dilution with H$_2$O, extraction with CH$_2$Cl$_2$, washing of the organic phase with water, drying and concentration, there is obtained a pasty solid which is recrystallized in toluene-heptane-acetone then in ethyl acetate-isopropyl ether to give 1.2 g (yield=28.2%) of an off-white powder. M.P.=100° C. (dec).

| Percentage analysis: C$_{20}$H$_{25}$ClNO$_5$PS (MW = 457.909) | | | | | | |
|---|---|---|---|---|---|---|
| | C % | H % | Cl % | N % | P % | S % |
| Calculated | 52.46 | 5.50 | 7.74 | 3.06 | 6.76 | 7.00 |
| Found | 52.17 | 5.67 | 7.47 | 3.01 | 6.70 | 7.16 |

I.R(KBr): $\nu$ (NH)=3280 cm$^{-1}$; (SO$_2$)=1320 cm$^{-1}$; (SO$_2$)=1150 cm$^{-1}$. N.M.R. (CDCl$_3$): $\delta$=1.0–1.7 (8H,m); 2.25–2.6 (4H,m); 2.6–3.0 (2H,m); 5.0–5.5 (1H,m, exchangeable with CF$_3$COOD); 6.6–8.0 (10H, 2H exchangeable with CF$_3$COOD).

EXAMPLE 84

4-[[1-[[[(4-Methylsulfinylphenyl)sulfonyl]amino]methyl]cyclopentyl]methyl]benzeneacetic acid a) N-[[1-[[4-(2-Hydroxyethyl)phenyl]methyl]cyclopentyl]methyl]-4-methylthiobenzenesulfonamide Obtained by operating as in example 32d, from 3 g (12.9 mmoles) of the compound prepared in example 32c, 1.6 g (15.8 mmoles) of triethylamine and 2.8 g (12.5 mmoles) of 4-methylthiobenzenesulfonyl chloride (prepared according to Burton H. and Hu P. F., J. Chem. Soc. (1948), 604–5) in 60 ml of dry dichloromethane. There is obtained 4.3 g (yield=80.1%) of a white solid, which is used without other purification. M.P.=131°–4° C. A fraction which is recrystallized in ethyl acetate gives a product which melts at M.P.=149.5°–151.5° C.

I.R. (KBr): $\nu$ (OH)=3480 cm$^{-1}$ (NH)=3180 cm$^{-1}$; (SO$_2$)=1300 cm$^{-1}$; (SO$_2$)=1150 cm$^{-1}$. N.M.R. (CDCl$_3$): $\delta$=1.25–1.85 (9H,m, 1H exchangeable with D$_2$O); 2.5 (3H,s); 2.55 (2H,s); 2.7 (2H,d, J=6.75 Hz, is converted into singulet with D$_2$O); 2.8 (2H,t, J=6.75 Hz); 3.8 (2H,t, J=6.75 Hz); 4.4 (1H,m, exchangeable with D$_2$O); 7.0 (4H,s); 7.1–7.4 (2H,m); 7.5–7.8 (2H,m).

b) 4-[[1-[[[(4-Methylsulfinylphenyl)sulfonyl]amino]methyl]cyclopentyl]methyl]benzeneacetic acid Obtained by operating as in example 25g, from 2.1 g (5 mmoles) of the compound prepared in example 84a, dissolved in 70 ml acetone and 4.7 ml (10.0 mmoles) of Jones reagent. After purification by chromatography on a column of silica in an ethyl acetate-methanol (4:1) mixture and recrystallization in ethyl acetate, there is obtained 0.1 g (yield=4.2%) of a white solid. M.P.=135°–6° C.

| Percentage analysis: C$_{22}$H$_{27}$NO$_5$S$_2$ + ¼ C$_4$H$_8$O$_2$ (ethyl acetate) (MW = 471.614) | | | | |
|---|---|---|---|---|
| | C % | H % | N % | S % |
| Calculated | 58.58 | 6.20 | 2.97 | 13.60 |
| Found | 58.53 | 6.25 | 2.73 | 13.63 |

I.R. (KBr): $\nu$ (NH)=3150 cm$^{-1}$; (C=O)=1710 cm$^{-1}$; (SO$_2$)=1325 cm$^{-1}$; (SO$_2$)=1165 cm$^{-1}$. N.M.R. (CDCl$_3$+DMSO d$_6$): $\delta$=1.25–1.6 (8H,m); 2.45–2.70 (5H,m, 1H exchangeable with CF$_3$COOD); 2.75 (3H,s); 3.5 (2H,s); 7.0 (4H,s); 7.4–8.0 (5H,m, 1H exchangeable with CF$_3$COOD).

EXAMPLE 85

4-[[1-[[[(4-acetamidophenyl)sulfonyl]amino]methyl]cyclopentyl]methyl]benzeneacetic acid a) 1-[[4-[2-[(3,4,5,6-Tetrahydro-2H-pyran-2-yl)oxy]ethyl]phenyl]methyl]cyclopentanecarbonitrile To a mixture consisting of 46.1 g (201 mmoles) of the alcohol prepared in example 26b, 0.1 g of para-toluenesulfonic acid and 205 ml of dry ether, maintained at 10° C., there is added 21.2 g (246.1 mmoles) of 3,4-dihydro-2H-pyran. Stirring is continued 16 hours at room temperature. The reaction mixture is then concentrated under vacuum to give a brown oil (yield=quantitative) used without other purification.

I.R. (film): $\nu$ (C≡N)=2240 cm$^{-1}$.

b) 1-[[4-[2-[(3,4,5,6-Tetrahydro-2H-pyran-2-yl)oxy]ethyl]phenyl]methyl]cyclopentanemethanamine To a suspension under nitrogen and at room temperature of 17.1 g (450.6 mmoles) of LiAlH$_4$ in 300 ml dry tetrahydrofuran, there is added dropwise 64.25 g (205 mmoles) of the compound prepared in example 85a, dissolved in 400 ml dry tetrahydrofuran. The mixture is then refluxed 4 hours, before being cooled to 0° C. and slowly adding 85.5 ml water, then 100 ml ether. The precipitate formed is filtrated over Na$_2$SO$_4$ and rinsed with ether. After concentration of the filtrate, there is obtained 66.8 g (yield=quantitative) of a yellow oil used without other purification.

I.R. (film): $\nu$ (NH$_2$)=3390 cm$^{-1}$. N.M.R. (CDCl$_3$): $\delta$=1.15 (2H,s, exchangeable with CF$_3$COOD); 1.3–2.25 (14H,m); 2.4 (2H,s); 2.6 (2H,s); 2.8 (2H,t, J=6.75 Hz); 3.35–4.05 (4H,m); 4.55 (1H,m); 7.0 (4H,s).

c) 4-Acetamido-N-[[1-[[4-[2-[(3,4,5,6-tetrahydro-2H-pyran-2-yl)oxy]ethyl]phenyl]methyl]cyclopentyl]methyl]benzenesulfonamide Obtained by operating as in example 1c, from 10 g (31.5 mmoles) of the compound prepared in example 85b in 190 ml dichloromethane, 3.75 g (37.1 mmoles) of triethylamine and 7.25 g (31.0 mmoles) of 4-acetamidobenzenesulfonyl chloride in 110 ml N,N-dimethylformamide. After stirring 16 hours at room temperature and the usual treatment, the product is purified by chromatography on a column of silica with a dichloromethane-methanol (19:1) mixture to give 10.7 g (yield=66.0%) of a beige oil which crystallizes. M.P.=100° C.

I.R. (KBr): $\nu$ (NH)=3310 cm$^{-1}$; (NH)=3190 cm$^{-1}$; (C=O)=1660 cm$^{-1}$; (SO$_2$)=1310 cm$^{-1}$; (SO$_2$)=1145 cm$^{-1}$. N.M.R. (CDCl$_3$): $\delta$=1.2–1.8 (14H,m); 2.2 (3H,s); 2.6 (2H,s); 2.5–2.8 (4H,m); 3.3–4.0 (4H,m); 4.6 (1H,m); 5.1 (1H,t, J=6.75 Hz, exchangeable with CF$_3$COOD); 7.0 (4H,s); 7.7 (4H,s); 7.8 (1H,s, exchangeable with CF$_3$COOD).

d) 4-Acetamido-N-[[1-[[4-(2-hydroxyethyl)phenyl]methyl]cyclopentyl]methyl]benzenesulfonamide A mixture of 6.3 g (12.2 mmoles) of the compound prepared in example 85c, 60 ml of methanol and 0.7 g of Amberlite IR-120 (plus) resin, is stirred 16 hours at room temperature. After filtration and concentration, there is obtained an oil which after grinding in hexane gives 3.6 g (yield=69.2%) of a creamy solid. M.P.=177°–80° C.

I.R. (KBr): ν (OH)=3560 cm$^{-1}$; (NH)=3270 cm$^{-1}$; (C=O)=1670 cm$^{-1}$; (SO$_2$)=1310 cm$^{-1}$; (SO$_2$)=1150 cm$^{-1}$.

e) 4-[[1-[[[(4-Acetamidophenyl)sulfonyl]amino]methyl]cyclopentyl]methyl]benzeneacetic acid Obtained by operating as in example 25g from 3.6 g (8.4 mmoles) of the compound prepared in example 85d, in 150 ml acetone and 8.8 ml (17.6 mmoles) of the Jones reagent. After purification by chromatography on a column of silica in a dichloromethane-methanol (9:1) mixture and recrystallizations in an acetone-hexane mixture, there is obtained 0.5 g (yield=13.5%) of an off-white solid. M.P. 174°-6° C.

| Percentage analysis: C$_{23}$H$_{28}$N$_2$O$_5$S (MW = 444.546) | | | | |
|---|---|---|---|---|
| | C % | H % | N % | S % |
| Calculated | 62.14 | 6.35 | 6.30 | 7.21 |
| Found | 61.91 | 6.32 | 6.63 | 7.32 |

I.R. (KBr): ν (NH)=3340 cm$^{-1}$; (NH)=3220 cm$^{-1}$; (C=O)=1690 cm$^{-1}$; (C=O)=1660 cm$^{-1}$; (SO$_2$)=1310 cm$^{-1}$; (SO$_2$)=1145 cm$^{-1}$. N.M.R. (acetone d$_6$+DMSO d$_6$): δ=1.2-1.7 (8H,m); 2.1 (3H,s); 2.65 (2H,s); 2.65 (2H,d, J=6 Hz, is converted into singulet with CF$_3$COOD); 3.5 (2H,s); 6.7 (1H,t, J=6 Hz, exchangeable with CF$_3$COOD); 7.1 (4H,s); 7.8 (4H,s); 9.8 (1H,s wide, exchangeable with CF$_3$COOD); 11.55 (1H,s wide, exchangeable with CF$_3$COOD).

This product is also obtained, by operating as in example 25 g from 10.7 g (20.8 mmoles) of the compound prepared in example 85c in 350 ml acetone and 26 ml (52 mmoles) of the Jones reagent. After purification by chromatography on a column of silica in a dichloromethane-methanol (9:1) mixture, there is obtained 3.7 g (yield=40.2%) of a pale yellow solid. M.P.=172°-3° C.

EXAMPLE 86

4-[[1-[[[(4-Aminophenyl)sulfonyl]amino]methyl]cyclopentyl]methyl]benzeneacetic acid A mixture of 3.7 g (8.3 mmoles) of the compound prepared in example 85e, 11.2 ml (112 mmoles) of 10N aqueous sodium hydroxide and 50 ml water, is refluxed 2 hours. After cooling and dilution with 50 ml water, an insoluble portion is filtered out, before washing with 100 ml ether. The aqueous phase acidified with diluted HCl to pH 6 gives a precipitate which after recrystallization in ethanol, ethanol-hexane then ethanol gives 0.3 g (yield=9.0%) of a beige solid. M.P.=175°-6° C.

| Percentage analysis: C$_{21}$H$_{26}$N$_2$O$_4$S (MW = 402.509) | | | | |
|---|---|---|---|---|
| | C % | H % | N % | S % |
| Calculated | 62.66 | 6.51 | 6.96 | 7.97 |
| Found | 62.43 | 6.76 | 7.26 | 8.05 |

I.R. (KBr): ν (NH$_2$)=3450 cm$^{-1}$ and 3370 cm$^{-1}$; (NH)=3260 cm$^{-1}$; (C=O)=1685 cm$^{-1}$; (SO$_2$)=1300 cm$^{-1}$; (SO$_2$)=1145 cm$^{-1}$. N.M.R. (DMSO d$_6$): δ=1.2-1.7 (8H,m); 2.35-2.7 (4H,m); 3.0-3.5 (1H,m, exchangeable with CF$_3$COOD); 3.45 (2H,s); 5.8 (1H,s wide, exchangeable with CF$_3$COOD); 6.45-6.7 (2H,m); 6.8-7.25 (6H,m, 2H exchangeable with CF$_3$COOD); 7.3-7.55 (2H,m).

EXAMPLE 87

4-[[1-[[[(4-Chlorophenyl)sulfonyl]amino]methyl]cyclohexyl]methyl]benzeneacetic acid a) 1-[[4-(2-Hydroxyethyl)phenyl]methyl]cyclohexanecarbonitrile To a mixture maintained under nitrogen, of 5.6 g (54.9 mmoles) of diisopropylamine and 92 ml of dry tetrahydrofuran, cooled to −40° C., there is added dropwise 34.2 ml (54.7 mmoles) of a 1.6M solution of n-butyllithium in hexane, then 8.2 g of 1,3-dimethylimidazolidin-2-one. The mixture is thereafter cooled to −78° C. and is stirred ¼ hour before adding 5.45 g (50 mmoles) of commercial cyclohexanecarbonitrile in solution in 82 ml of dry tetrahydrofuran. After having stirred 1 hour, at −78° C., 14.3 g (50 mmoles) of the compound prepared in example 26a is added. The temperature is kept for an additional 3 hours at −78° C., before being allowed to rise and the mixture is stirred 19 hours at room temperature. Waster is then added, the mixture is acidified with HCl and is stirred again for 1 hour, before diluting it with water and extracting the reaction mixture with ether. The organic phase, washed with water, dried over Na$_2$SO$_4$ is concentrated. The liquid obtained is purified by distillation to give 7.5 g (yield=61.6%) of a yellow liquid. b.p.$_{0.5}$=130°-80° C.

I.R. (film): ν (OH)=3440 cm$^{-1}$; (C≡N)=2230 cm$^{-1}$. N.M.R. (CDCl$_3$): δ=0.9-2.1 (10H,m); 1.6 (1H,s, exchangeable with CF$_3$COOD); 2.75 (2H,s); 2.8 (2H,t, J=6.75 Hz); 3.8 (2H,t, J=6.75 Hz); 7.1 (4H,s).

b) 4-[[1-(Aminomethyl)cyclohexyl]methyl]benzeneethanol

Obtained by operating as in example 32c from 2.5 g (67.8 mmoles) of LiAlH$_4$ in 50 ml of dry tetrahydrofuran and 7.5 g (30.8 mmoles) of the compound prepared in example 87a in solution in 60 ml of dry tetrahydrofuran. After purification by chromatography on a column of silica in methanol, there is obtained 5.1 g (yield=67.1%) of a yellow oil.

I.R. (film): ν (NH$_2$)=3375 and 3300 cm$^{-1}$; (OH)=3300 cm$^{-1}$. N.M.R. (CDCl$_3$): δ=1.0-1.75 (13H,m, 3H exchangeable with D$_2$O); 2.4 (2H,s); 2.5 (2H,s); 2.8 (2H,t, J=6.75 Hz); 3.8 (2H,t, J=6.75 Hz); 7.0 (4H,s).

c) 4-Chloro-N-[[1-[[4-(2-hydroxyethyl)phenyl]methyl]cyclohexyl]methyl]benzenesulfonamide Obtained as in example 32d, from 5.1 g (20.6 mmoles) of the compound prepared in example 87b, in 71 ml of dry dichloromethane, 2.5 g (24.7 mmoles) of triethylamine and 4.2 g (19.7 mmoles) of 4-chlorobenzenesulfonyl chloride. There is obtained 6.3 g (yield=75.9%) of a white solid used without other purification. M.P.=178°-82° C. A fraction purified by recrystallization in an ethanol-DMF mixture, and ethanol gives a white solid. M.P.=179°-82° C.

| Percentage analysis: C$_{22}$H$_{28}$ClNO$_3$S (MW = 421.983) | | | | | |
|---|---|---|---|---|---|
| | C % | H % | Cl % | N % | S % |
| Calculated | 62.62 | 6.69 | 8.40 | 3.32 | 7.60 |
| Found | 62.71 | 6.59 | 8.39 | 3.22 | 7.40 |

I.R. (KBr): ν (OH)=3515 cm$^{-1}$; (NH)=3220 cm$^{-1}$; (SO$_2$)=1300 cm$^{-1}$; (SO$_2$)=1145 cm$^{-1}$. N.M.R. (DMSO d$_6$): δ=0.75-1.6 (10H,m); 2.3-2.8 , (6H,m); 3.3 (1H,s, exchangeable with CH$_3$COOD); 3.6 (2H,t, J=6.75 Hz); 4.5 (1H,t, J=6.75 Hz, exchangeable with CF$_3$COOD); 6.9 (4H,s); 7.3-8.0 (4H,m).

d) 4-[[1-[[[(4-Chlorophenyl)sulfonyl]amino]methyl]cyclohexyl]methyl]benzeneacetic acid Obtained by operating as in example 25g, from 5.9 g (14.0 mmoles) of the compound prepared in example 87c, dissolved in 190 ml acetone and 12.8 ml (28 mmoles) of Jones reagent. After recrystallization in an ethyl acetate-ethanol mixture followed by ethyl acetate, there is obtained 1.5 g (yield=24.6%) of a white solid. M.P.=191°-4° C.

| Percentage analysis: C$_{22}$H$_{26}$ClNO$_4$S (MW = 435.966) | | | | | |
|---|---|---|---|---|---|
| | C % | H % | Cl % | N % | S % |
| Calculated | 60.61 | 6.01 | 8.13 | 3.21 | 7.35 |
| Found | 60.63 | 6.17 | 8.21 | 3.31 | 7.55 |

I.R. (KBr): $\nu$ (NH)=3270 cm$^{-1}$; (C=O)=1700 cm$^{-1}$; (SO$_2$)=1310 cm$^{-1}$; (SO$_2$)=1155 cm$^{-1}$. N.M.R. (DMSO d$_6$): $\delta$=0.8-1.7 (10H,m); 2.3-2.75 (4H,m); 3.5 (2H,s); 7.0 (4H,s); 7.3-8.0 (5H,m, 1H exchangeable with CF$_3$COOD); 12.1 (1H,s, exchangeable with CF$_3$COOD).

EXAMPLE 88

4-[[4-[[[(4-Chlorophenyl)sulfonyl]amino]methyl]tetrahydropyran-4-yl]methyl]benzeneacetic acid a) 4-[[4-(2-Hydroxyethyl)phenyl]methyl]tetrahydropyran-4-carbonitrile Obtained by operating as in example 87a, from 6.3 g (62.2 mmoles) of diisopropylamine in 104 ml of tetrahydrofuran, 38.7 ml (62.0 mmoles) of a 1.6M solution of n-butyllithium in hexane, 9.3 g of 1,3-dimethylimidazolidin-2-one, 8.8 g (56.7 mmoles) of 2,3,5,6-tetrahydro-4H-pyran-4-carbonitrile (prepared according to Gibson C. S. and Johnson J. D. A., J. Chem. Soc. (1930), 2525-30) in 93 ml tetrahydrofuran and 17.7 g (62 mmoles) of the compound prepared in example 26a. After purification by chromatography on a column of silica in a hexane-ethyl acetate (1:1) mixture, there is obtained 10.5 g (yield=75.5%) oil.

I.R. (film): $\nu$ (OH)=3400 cm$^{-1}$; (C≡N)=2220 cm$^{-1}$. N.M.R. (CDCl$_3$): $\delta$=1.55 (1H,s, exchangeable with D$_2$O); 1.6-1.9 (4H,m); 2.8 (2H,s); 2.8 (2H,t, J=6.75 Hz); 3.4-4.2 (6H,m); 7.1 (4H,s).

b) 4-[[4-(Aminomethyl)tetrahydropyran-4-yl]methyl]benzeneethanol

Obtained by operating as in example 32c, from 3.45 g (94.3 mmoles) of LiAlH$_4$ in 80 ml of dry tetrahydrofuran and 10.5 g (42.8 mmoles) of the compound prepared in example 88a in solution in 80 ml dry tetrahydrofuran. There is obtained 7.1 g (yield=66.3%) of an oil, which is used without other purification.

I.R. (film): $\nu$ (NH$_2$)=3370 and 3290 cm$^{-1}$; (OH)=3360 cm$^{-1}$. N.M.R. (CDCl$_3$): $\delta$=1.0-2.0 (4H,m) 1.65 (3H,s exchangeable with D$_2$O); 2.5 (2H,s); 2.6 (2H,s); 2.8 (2H,t, J=6.75 Hz); 3.45-4.0 (6H,m); 7.0 (4H,s).

c) 4-Chloro-N-[[4-[[4-(2-hydroxyethyl)phenyl]methyl]-tetrahydropyran-4-yl]methyl]benzenesulfonamide Obtained by operating as in example 32d, from 7.1 g (28.4 mmoles) of the compound prepared in example 88b, in 100 ml of dry dichloromethane, 3.4 g (33.9 mmoles) of triethylamine and 5.75 g (27.2 mmoles) of 4-chlorobenzenesulfonyl chloride. There is obtained 5.4 g (yield=46.8%) of a white solid which is used without other purification. M.P.=178°-80° C. A fraction purified by recrystallization in an ethyl acetate-ethanol mixture, then in ethyl acetate gives a white solid. M.P.=180°-1° C.

| Percentage analysis: C$_{21}$H$_{26}$ClNO$_4$O (MW = 423.955) | | | | | |
|---|---|---|---|---|---|
| | C % | H % | Cl % | N % | S % |
| Calculated | 59.49 | 6.18 | 8.36 | 3.30 | 7.56 |
| Found | 59.56 | 6.22 | 8.50 | 3.26 | 7.29 |

I.R. (KBr): $\nu$ (OH)=3540 cm$^{-1}$; (NH)=3260 cm$^{-1}$; (SO$_2$)=1305 cm$^{-1}$; (SO$_2$)=1145 cm$^{-1}$. N.M.R. (DMSO d$_6$): $\delta$=1.0-1.5 (4H,m); 2.3-2.85 (6H,m); 3.25-3.8 (6H,m); 4.0 (1H, s wide, exchangeable with CF$_3$COOD); 6.9 (4H,s); 7.35-7.95 (5H,m, 1H exchangeable with CF$_3$COOD).

d) 4-[[4-[[[(4-Chlorophenyl)sulfonyl]amino]methyl]tetrahydropyran-4-yl]methyl]benzeneacetic acid Obtained by operating as in example 25g, from 4.9 g (11.5 mmoles) of the compound prepared in example 88c, dissolved in 150 ml acetone and 10.5 ml (22.9 mmoles) of Jones reagent. After recrystallization in ethyl acetate, there is obtained 0.5 g (yield=9.9%) of a white solid. M.P.=179°-80° C.

| Percentage analysis: C$_{21}$H$_{24}$ClNO$_5$S (MW = 437.938) | | | | | |
|---|---|---|---|---|---|
| | C % | H % | Cl % | N % | S % |
| Calculated | 57.60 | 5.52 | 8.10 | 3.20 | 7.32 |
| Found | 57.88 | 5.41 | 8.24 | 3.40 | 7.06 |

I.R. (KBr): $\nu$ (NH)=3250 cm$^{-1}$; (C=O)=1685 cm$^{-1}$; (SO$_2$)=1310 cm$^{-1}$; (SO$_2$)=1155 cm$^{-1}$. N.M.R. (DMSO d$_6$): $\delta$=1.1-1.5 (4H,m); 2.45-2.8 (4H,m); 3.3 (1H, exchangeable with CF$_3$COOD); 3.4-3.75 (6H,m); 7.0 (4H,s); 7.5-8.0 (4H,m); 12.1 (1H,s wide, exchangeable with CF$_3$COOD).

EXAMPLE 89

4-[[1-[[[(4-Chlorophenyl)sulfonyl]amino]methyl]-3,3-dimethylcyclobutyl]methyl]benzeneacetic acid a) 3,3-Dimethyl-1-[[4-(2-hydroxyethyl)phenyl]methyl]-cyclobutanecarbonitrile Obtained by operating as in example 72a, from 3.2 g (32 mmoles) of diisopropylamine in 34 ml of dry tetrahydrofuran, 20 ml (38.4 mmoles) of a 1.6M solution of n-butyllithium in hexane, 2.9 g (26.5 mmoles) of 3,3-dimethylcyclobutanecarbonitrile (prepared according to Brannock K. C. et al., J. Org. Chem. (1964) 29, 801-12) in 30 ml of dry tetrahydrofuran and 11.4 g (39.7 mmoles) of the compound prepared in example 26a in 10 ml of dry tetrahydrofuran. After recrystallization in a hexane-ethyl acetate mixture, there is obtained 5.0 g (yield=77.5%) of a solid. M.P.=51°-4° C.

I.R. (KBr): $\nu$ (OH)=3390 cm$^{-1}$; (C≡N)=2250 cm$^{-1}$. N.M.R. (CDCl$_3$): $\delta$=1.05 (3H,s); 1.25 (3H,s); 1.7 (1H,s, exchangeable with D$_2$O); 2.1 (4H,m); 2.8 (4H,m); 3.8 (2H,t, J=6 Hz); 6.9-7.1 (4H,m).

b) 4-[[1-(Aminomethyl)-3,3-dimethylcyclobutyl]methyl]benzeneethanol

Obtained by operating as in example 25e, from 5.5 g (145 mmoles) of LiAlH$_4$ and 28.1 g (97 mmoles) of the compound prepared in example 89a in 300 ml dry ether. There is obtained 16 g (yield=66.7%) of a clear yellow oil, which is used without other purification.

I.R. (film): $\nu$ (OH)=3300 cm$^{-1}$; (NH$_2$)=3360 and 3280 cm$^{-1}$. N.M.R. (CDCl$_3$): $\delta$=1.0 (3H,s); 1.05 (3H,s);

1.5–1.85 (7H,m, 3H exchangeable with D₂O); 2.6 (2H,t, J=6.0 Hz); 2.6–3.0 (4H,m); 3.8 (2H,t, J=6.0 Hz); 6.85–7.4 (4H,m).

c) 4-Chloro-N-[[3,3-dimethyl-1-[[4-(2-hydroxyethyl)-phenyl]methyl]cyclobutyl]methyl]-benzenesulfonamide Obtained by operating as in example 32d, from 8.0 g (32.3 mmoles) of the compound prepared in example 89b, 3.9 g (38.8 mmoles) of triethylamine, 6.7 g (31.6 mmoles) of 4-chlorobenzenesulfonyl chloride in 150 ml dry dichloromethane. After purification by chromatography on a column of silica in a hexane-ethyl acetate (1:1) mixture, there is obtained 3.8 g (yield=27.8%) of a white solid. M.P.=90°–2° C.

I.R. (KBr): ν (OH)=3470 cm⁻¹; (NH)=3160 cm⁻¹; (SO₂)=1320 cm⁻¹; (SO₂)=1145 cm⁻¹. N.M.R. (CDCl₃): δ=1.0 (6H,s); 1.5–1.85 (5H,m, 1H exchangeable with CF₃COOD); 2.7 (2H,s); 2.8 (2H,t, J=6 Hz); 2.85 (2H,d, J=6 Hz); 3.8 (2H,t, J=6 Hz); 4.65 (1H,t, J=6 Hz, exchangeable with CF₃COOD); 7.0 (4H,s); 7.3–8.0 (4H,m).

d) 4-[[1-[[[(4-Chlorophenyl)sulfonyl]amino]methyl]-3,3-dimethylcyclobutyl]methyl]benzeneacetic acid Obtained by operating as in example 25g, from 3.5 g (8.3 mmoles) of the compound prepared in example 89c, dissolved in 83 ml acetone and 8.3 ml (16.6 mmoles) of Jones reagent. After recrystallization in toluene, there is obtained 1.3 g (yield=35.9%) of a white solid. M.P.140°–2° C.,

| Percentage analysis: C₂₂H₂₆ClNO₄s (MW = 435.96) | | | | | |
|---|---|---|---|---|---|
| | C % | H % | Cl % | N % | S % |
| Calculated | 60.61 | 6.01 | 8.13 | 3.21 | 7.35 |
| Found | 60.71 | 6.21 | 8.20 | 3.18 | 7.30 |

I.R. (KBr): ν (NH)=3270 cm⁻¹; (C=O)=1695 cm⁻¹; (SO₂)=1325 cm⁻¹; (SO₂)=1160 cm⁻¹. N.M.R. (DMSO d₆): δ=0.9 (3H,s); 1.0 (3H,s); 1.6 (4H,s); 2.55–2.8 (4H,m); 3.45 (2H,s); 7.0 (4H,s); 7.35–7.9 (5H,m, 1H exchangeable with CF₃COOD); 12.1 (1H,s wide, exchangeable with CF₃COOD).

EXAMPLE 90

4-[[1-[[[(4-Chlorophenyl)sulfonyl]amino]methyl]-2,2,3,3-tetramethylcyclopropyl]methyl]benzeneacetic acid a) 1-[[4-(2-Hydroxyethyl)phenyl]methyl]-2,2,3,3-tetramethylcyclopropanecarbonitrile Obtained by operating as in example 87a, from 19.7 g (195 mmoles) of diisopropylamine, 122 ml (195 mmoles) of a 1.6M solution of n-butyllithium in hexane, 45 ml of 1,3-dimethylimidazolidin-2-one, 21.8 g of 2,2,3,3-tetramethylcyclopropanecarbonitrile (prepared according to patent FR 2,479,192), 51.9 g (180.5 mmoles) of the compound prepared in example 26a in 295 ml tetrahydrofuran. After distillation, there is obtained 20 g (yield=44.0%) of a thick yellow oil. b.p.₀.₈=185°–205° C.

I.R. (film): ν (OH)=3420 cm⁻¹; (C≡N)=2230 cm⁻¹. N.M.R. (CDCl₃): δ=1.1 (6H,s); 1.3 (6H,s); 2.1 (1H,s, exchangeable with CF₃COOD); 2.75 (2H,t, J=6.75 Hz); 2.8 (2H,s); 3.75 (2H,t, J=6.75 Hz); 7.1 (4H,s).

b) 4-[[1-(Aminomethyl)-2,2,3,3,-tetramethylcyclopropyl]methyl]benzeneethanol

Obtained by operating as in example 13a, from 30 ml (101 mmoles) of 13% commercial solution of LiAlH₄ in a toluene-tetrahydrofuran mixture, 20 g (77.7 mmoles) of nitrile prepared in example 90a, and 130 ml dry tetrahydrofuran. After distillation, there is obtained 13.2 g (yield=65.0%) of a very thick orange colored liquid, which crystallizes. b.p.₀.₃=190°–220° C. M.P.=103°–6° C. (ethyl acetate).

I.R. (KBr): ν (OH)=3380 cm⁻¹; (NH₂)=3380 cm⁻¹. N.M.R. (CDCl₃): δ=0.75–1.4 (12H,m); 1.7 (3H,s, exchangeable with CF₃COOD); 2.5–3.2 (6H,m); 3.75 (2H,t, J=6.75 Hz); 6.75–7.3 (4H,m).

c) 4-Chloro-N-[[1-[[4-(2-hydroxyethyl)phenyl]methyl]2,2,3,3-tetramethylcyclopropyl]methyl]benzenesulfonamide Obtained by operating as in example 32d, from 3.8 g (14.5 mmoles) of the compound prepared in example 90b, 2.4 ml (17.4 mmoles) of triethylamine and 3 g (14.25 mmoles of 4-chlorobenzenesulfonyl chloride in 65 ml of dry dichloromethane. After recrystallization in ethyl acetate, there is obtained 4.2 g (yield=66.7%) of an off-white solid. M.P.=158°–60° C.

A fraction purified by filtration over a column of silica in a hexane-ethyl acetate mixture followed by recrystallization in the same mixture, gives a white solid. M.P.=162°–3° C.

| Percentage analysis: C₂₃H₃₀ClNO₃S (MW = 436.01) | | | | | |
|---|---|---|---|---|---|
| | C % | H % | Cl % | N % | S % |
| Calculated | 63.36 | 6.94 | 8.13 | 3.21 | 7.35 |
| Found | 63.49 | 6.88 | 8.28 | 3.19 | 7.16 |

I.R. (KBr): ν (NH)=3440 cm⁻¹; (OH)=3140 cm⁻¹; (SO₂)=1310 cm⁻¹; (SO₂)=1145 cm⁻¹. N.M.R. (acetone d₆): δ=0.85–1.2 (12H,m); 2.55–3.0 (6H,m); 3.6 (1H,s, exchangeable with CF₃COOD); 3.7 (2H,t, J=6.75 Hz); 5.95 (1H,t, J=6.75 Hz, exchangeable with CF₃COOD); 6.75–7.1 . (4H,m); 7.25–7.75 (4H,m).

d) 4-[[1-[[[(4-Chlorophenyl)sulfonyl]amino]methyl]-2,2,3,3-tetramethylcyclopropyl]methyl]benzeneacetic acid Obtained by operating as in example 25g, from 3.5 g (8 mmoles) of the compound prepared in example 90c, 7.6 ml (16 mmoles) of Jones reagent in 80 ml acetone. After purification by chromatography on a column of silica with a toluene-ethyl acetate (4:0 to 4:1) mixture followed by a recrystallization in toluene, there is obtained 1.8 g (yield=50.0%) of a white solid. M.P.=176°–8° C.

| Percentage analysis: C₂₃H₂₈ClNO₄S (MW = 449.993) | | | | | |
|---|---|---|---|---|---|
| | C % | H % | Cl % | N % | S % |
| Calculated | 61.39 | 6.27 | 7.88 | 3.11 | 7.12 |
| Found | 61.68 | 6.00 | 8.02 | 3.28 | 7.05 |

I.R. (KBr): ν (NH)=3290 cm⁻¹; (C=O)=1700 cm⁻¹; (SO₂)=1340 cm⁻¹; (SO₂)=1160 cm⁻¹. N.M.R. (acetone d₆): δ=0.9–1.25 (12H,m); 2.8 (2H,s); 2.9 (2H,d, J=5.25 Hz, is converted into singulet with CF₃COOD); 3.55 (2H,s); 6.0 (1H,t, J=5.25 Hz, exchangeable with CF₃COOD); 6.75–7.3 (4H,m); 7.3–7.9 (4H,m); 10.5 (1H,s wide, exchangeable with CF₃COOD).

EXAMPLE 91

4-[[1-[[[(4-Chlorophenyl)sulfonyl]amino]methyl]-4-oxocyclohexyl]methyl]benzeneacetic acid a) 4-[[(1,1-Dimethylethyl)diphenylsilyl]oxy]cyclohexanecarbonitrile To a solution maintained at 10° C., under nitrogen, of 11 g (87.8 mmoles) of 4-hydroxycyclohexanecarbonitrile (prepared according to Praefcke K. and Schmidt D., Z. Naturforsch (1980) 35b, 1451–4) in 50 ml of N,N-dimethylformamide, there is added dropwise 26.6 g (96.8 mmoles) of 1,1-dimethylethyldiphenylsilyl chloride, then by portions, 13.1 g (190 mmoles) of imidazole. Stirring is continued at room temperature during 3 days, before pouring the reaction mixture in water saturated with NaCl. The product is extracted with a hexane-ether (1:1) mixture. The organic phase is washed with a N HCl solution, then with water saturated with NaCl, before drying and concentration. The residue is purified by chromatography on a column of silica in dichloromethane to give 26.5 g (yield=85.9%) of a colorless thick oil.

I.R. (film): $\nu$ (C≡N)=2240 cm$^{-1}$. N.M.R. (CDCl$_3$): $\delta$=0.7 (9H,s); 0.9–1.90 (8H,m); 2.1 (1H,m); 3.35 (1H,m); 6.8–7.45 (10H,m).

b) 4-[[(1,1-Dimethylethyl)diphenylsilyl]oxy]-1-[[4-(2-hydroxyethyl)phenyl]methyl]cyclohexanecarbonitrile Obtained by operating as in example 87a, from 17.5 g (173 mmoles) of diisopropylamine, 88.5 ml (145 mmoles) of a 1.6M solution of n-butyllithium in hexane, 20.6 g of 1,3-dimethylimidazolidin-2-one, 42.4 g (120 mmoles) of the compound prepared in example 91a, in 38 g (132 mmoles) of the halide prepared in example 26a, in 180 ml dry tetrahydrofuran. After purification on a column of silica in a hexane-ethyl acetate (7:1 to 4:1) mixture, there is obtained 12.7 g (yield=22.4%) of a white pasty solid.

I.R. (KBr): $\nu$ (OH)=3400 cm$^{-1}$; (C≡N)=2240 cm$^{-1}$.

N.M.R. (CDCl$_3$): $\delta$=1.0 (9H,s); 1.5 (1H,s, exchangeable with CF$_3$COOD); 1.5–2.0 (8H,m); .2.7 (2H,s); 2.8 (2H,t, J=6.75 Hz); 3.6 (1H,m); 3.8 (2H,t, J=6.75 Hz); 7.0 (4H,s); 7.2–7.75 (10H,m).

c) 4-[[1-(Aminomethyl)-4-hydroxycyclohexyl]methyl]-benzeneethanol

Obtained by operating as in example 32c, but at room temperature, from 1 g (26.3 mmoles) of LiAlH$_4$, 5 g (10.6 mmoles) of the compound prepared in example 91b, in 60 ml of dry tetrahydrofuran. After treatment with aqueous HCl and the usual treatment, there is obtained 2.3 g (yield=82.1%) of a thick oil which crystallizes slowly.

I.R. (film): $\nu$ (OH)=3350 cm$^{-1}$. N.M.R. (DMSO d$_6$): $\delta$=0.9–1.8 (10H,m, 2H exchangeable with CF$_3$COOD); 2.25–2.9 (6H,m); 3.05–3.7 (3H,m, 2H exchangeable with CF$_3$COOD); 3.55 (2H,t, J=6.75 Hz); 7.0 (4H,s).

d) 4-Chloro-N-[[4-hydroxy-1-[[4-(2-hydroxyethyl)-phenyl]methyl]cyclohexyl]methyl]benzenesulfonamide Obtained by operating as in example 32d, from 1.8 g (6.8 mmoles) of the compound prepared in example 91c, 0.9 g (8.9 mmoles) of triethylamine, 1.3 g (6.3 mmoles) of 4-chlorobenzenesulfonyl chloride in 100 ml dry dichloromethane and 20 ml ether. There is obtained 1.1 g (yield=36.7%) of a white powder which is used without other purification. M.P.=171°–4° C.

I.R. (KBr): $\nu$ (NH)=3500 cm$^{-1}$; (OH)=3400 cm$^{-1}$; (SO$_2$)=1310 cm$^{-1}$; (SO$_2$)=1140 cm$^{-1}$. N.M.R. (acetone d$_6$+DMSO d$_6$): $\delta$=1.0–1.9 (8H,m); 2.6–2.9 (6H,m); 3.25–3.8 (6H, 3H exchangeable with CF$_3$COOD); 7.0 (4H,s); 7.4–8.0 (4H,m).

e) 4-[[1-[[[(4-Chlorophenyl)sulfonyl]amino]methyl]-4oxocyclohexyl]methyl]benzeneacetic acid Obtained by operating as in example 25g, from 1.1 g (2.5 mmoles) of the compound prepared in example 91d, 4.7 ml (5 mmoles) of Jones reagent in 30 ml acetone. After chromatography on a column of silica in a dichloromethane-methanol (95:5) mixture, there is obtained 0.3 g (yield=26.5%) of an off-white powder. M.P.=205°–10° C. (dec.).

| Percentage analysis: C$_{22}$H$_{24}$ClNO$_5$S (MW = 449.949) | | | | | |
|---|---|---|---|---|---|
| | C % | H % | Cl % | N % | S % |
| Calculated | 58.73 | 5.38 | 7.88 | 3.11 | 7.13 |
| Found | 58.60 | 5.71 | 8.09 | 2.98 | 6.93 |

I.R. (KBr): $\nu$ (NH)=3250 cm$^{-1}$; (C=O)=1680 cm$^{-1}$; (C=O)=1690 cm$^{-1}$; (SO$_2$)=1310 cm$^{-1}$; (SO$_2$)=1160 cm$^{-1}$. N.M.R. (DMSO d$_6$): $\delta$=1.5–1.9 (4H,m); 2.1–2.45 (4H,m); 2.6–2.95 (4H,m); 3.3 (1H,m, exchangeable with CF$_3$COOD); 3.5 (2H,s); 7.0 (4H,s); 7.5–8.0 (4H,m); 12.1 (1H,s wide, exchangeable with CF$_3$COOD).

EXAMPLE 92

2-[[1-[[[(4-Chlorophenyl)sulfonyl]amino]methyl]cyclopentyl]methyl]benzeneacetic acid a) 2-(Bromomethyl)benzeneacetic acid A solution of 10 g (66.6 mmoles) of commercial 2-methylbenzeneacetic acid in 100 ml of carbon tetrachloride is refluxed, under a UV lamp. A solution made of 13.8 g (86.6 mmoles) of bromine and 33 ml of carbon tetrachloride is poured dropwise during 2 hours. The reflux condition is maintained 1 hour after the end of the addition and the mixture is concentrated to dryness. The residue recrystallizes in carbon tetrachloride then, in a hexane-ethyl acetate mixture, gives 5 g (yield=32.9%) of a white solid. M.P.=129°–32° C. (Lit.: 129°–32° C.; Leroy Chauffe L. J. A. and Keefer R. M., J. Org. Chem. (1966) 31, 3758–68).

I.R. (KBr): $\nu$ (C=O)=1675 cm$^{-1}$. N.M.R. (CDCl$_3$+DMSO d$_6$): $\delta$=3.7 (2H,s); 4.55 (2H,s); 7.2 (4H,s); 10.75 (1H,s wide, exchangeable with CF$_3$COOD).

b) 2-(Bromomethyl)benzeneethanol

Obtained by operating as in example 25a, from 1.8 g (24 mmoles) of the boron hydride-dimethylsulfide complex and 5 g (21.8 mmoles) of the compound prepared in example 92a, in 50 ml tetrahydrofuran. There is obtained 3.5 g (yield=74.6%) of a pale yellow oil which is used without other purification.

I.R. (film): $\nu$ (OH)=3350 cm$^{-1}$. N.M.R. (CDCl$_3$): $\delta$=1.2 (2H,t, J=6.75 Hz); 3.4 (1H,s, exchangeable with D$_2$O); 3.85 (2H,t, J=6.75 Hz); 4.5 (2H,s); 7.2 (4H,s).

c) 1-(Bromomethyl)-2-[2-(trimethylsilyloxy)ethyl]benzene

Obtained by operating as in example 26a, from 47.3 g (220 mmoles) of the compound prepared in example 92b, 35.5 g (220 mmoles) of 1,1,1,3,3,3-hexamethyldisilazane, 22.25 g (220 mmoles) of triethylamine and 23.9 g (220 mmoles) of trimethylsilyl chloride in 475 ml tetrahydrofuran. After distillation, there is obtained 42.5 g (yield=67.3%) of a colorless liquid. b.p.$_{0.7}$=98°–102° C.

N.M.R. (CDCl$_3$): $\delta$=0.0 (9H,s); 2.9 (2H,t, J=6.75 Hz); 3.8 (2H,t, J=6.75 Hz); 4.5 (2H,s); 6.9–7.6 (4H,m).

d) 1-[[2-(2-Hydroxyethyl)phenyl]methyl]cyclopentanecarbonitrile

Obtained by operating as in example 87a, from 7.8 g (77 mmoles) of diisopropylamine, 48.2 ml of a 1.6M solution of n-butyllithium in hexane, 6.7 g (70 mmoles)

of commercial cyclopentanecarbonitrile, 18 ml of 1,3-dimethylimidazolidin-2-one and 20.5 g (71.4 mmoles) of the compound prepared in example 92c in 20 ml of tetrahydrofuran. After distillation, there is obtained 8.8 g (yield=55.0%) of a beige viscous liquid. b.p.$_{0.4}$=165° C.

I.R. (film): $\nu$ (OH)=3360cm$^{-1}$; (C≡N)=2215 cm$^{-1}$. N.M.R. (CDCl$_3$): δ=1.4–2.25 (8H,m); 2.8 (1H,s, exchangeable with D$_2$O); 3.0 (4H,m); 3.8 (2H,t, J=6.75 Hz); 7.15 (4H,m).

e) 2-[[1-(Aminomethyl)cyclopentyl]methyl]benzeneethanol

Obtained by operating as in example 15a, from 1.8 g (45.6 mmoles) of LiAlH$_4$, 8.8 g (38 mmoles) of the compound prepared in example 92 d in 50 ml of ether. There is obtained 3.3 g (yield=37.2%) of a pale yellow thick oil used without other purification.

I.R. (film): $\nu$ (NH$_2$)=3360 and 3290 cm$^{-1}$. N.M.R. (CDCl$_3$): δ=1.25–1.75 (8H,m); 2.05 (3H,s, exchangeable with D$_2$O); 2.5 (2H,s); 2.75 (2H,s); 2.9 (2H,t, J=6.75 Hz); 3.8 (2H,t, J=6.75 Hz); 7.2 (4H,s).

f) 4-Chloro-N-[[1-[[2-(2-hydroxyethyl)phenyl]methyl]cyclopentyl]methyl]benzenesulfonamide Obtained by operating as in example 32d, from 3 g (12.8 mmoles) of the compound prepared in example 92c, 1.6 g (16.2 mmoles) of triethylamine and 2.65 g (12.5 mmoles) of 4-chlorobenzenesulfonyl chloride in 80 ml of dry dichloromethane. After purification by chromatography on a column of silica in a dichloromethane-methanol (98:2) mixture, there is obtained 2.3 g (yield=45.1%) of a pasty solid.

I.R. (film): $\nu$ (NH)=3420 cm$^{-1}$; (OH)=3120 cm$^{-1}$; (SO$_2$)=1290 cm$^{-1}$; (SO$_2$)=1125 cm$^{-1}$. N.M.R. (CDCl$_3$): δ=1.25–1.75 (8H,m); 2.5–3.1 (7H,m, 1H exchangeable with CF$_3$COOD); 3.8 (2H,t, J=6.75 Hz); 5.7 (1H,t, J=6.75, exchangeable with CF$_3$COOD); 7.0–7.3 (4H,m); 7.3–8.0 (4H,m).

g) 2-[[1-[[[(4-Chlorophenyl)sulfonyl]amino]methyl]cyclopentyl]methyl]benzeneacetic acid Obtained by operating as in example 25g, from 2.3 g (5.6 mmoles) of the compound prepared in example 92f, 5.3 ml (11.2 mmoles) of Jones reagent in 70 ml acetone. After chromatography on a column of silica in a dichloromethane-methanol (98:2) mixture and recrystallization in isopropyl ether, there is obtained 0.2 g (yield=8.5%) of a white solid. M.P.=124°–6° C.

| Percentage analysis: C$_{21}$H$_{24}$ClNO$_4$S (MW = 421.95) | | | | | |
|---|---|---|---|---|---|
| | C % | H % | Cl % | N % | S % |
| Calculated | 59.78 | 5.73 | 8.40 | 3.32 | 7.60 |
| Found | 60.09 | 5.80 | 8.45 | 3.38 | 7.30 |

I.R. (KBr): $\nu$ (NH)=3250 cm$^{-1}$; (C=O)=1715 cm$^{-1}$; (SO$_2$)=1290 cm$^{-1}$; (SO$_2$)=1145 cm$^{-1}$. N.M.R. ((CDCl$_3$): δ=1.3–1.75 (8H,m); 2.7 (2H,s); 2.8 (2H,d, J=6.75 Hz, is converted into singulet with CF$_3$COOD) 3.7 (2H,s); 5.3 (1H,t, J=6.75 Hz, exchangeable with CF$_3$COOD); 7.0–7.3 (4H,m); 7.3–7.8 (4H,m); 9.6 (1H, S wide, exchangeable with CF$_3$COOD).

EXAMPLE 93

3-[[1-[[[(4-Chlorophenyl)sulfonyl]amino]methyl]cyclopentyl]methyl]benzeneacetic acid a) 3-(Bromomethyl)benzeneacetic acid Obtained by operating as in example 92 a, from 89 g (590 mmoles) of commercial 3-methylbenzeneacetic acid, 123 g (767 mmoles) of bromine in 1200 ml of carbon tetrachloride. After cooling, there is obtained a white precipitate which is filtered off. A second crop is obtained by adding 1 l of hexane to the filtrate. The two precipitates combined represent 40.5 g (yield=30.0%) of a product used without other purification. M.P.=92°–4° C. (Lit.: M.P.=117°–20° C., according to Snim S. C. et al., Bull. Korean Chem. Soc. (1988) 9, 185–7 ; CA 110, 74976 j).

I.R. (KBr): $\nu$ (C=O)=1680 cm$^{-1}$. N.M.R. (CDCl$_3$): δ=3.65 (2H,s); 4.5 (2H,s); 7.25 (4H,s); 10.4 (1H, S wide, exchangeable with CF$_3$COOD).

b) 3-(Bromomethyl)benzeneethanol

Obtained by operating as in example 25a, from 46.7 g (204 mmoles) of the compound prepared in example 93a, 17 g (224.4 mmoles) of the boron hydridedimethylsulfide complex in a 2M toluene solution, in 500 ml of dry tetrahydrofuran. There is obtained 40 g (yield=93.0%) of a pale yellow solid, which is used without other purification.

I.R. (KBr): $\nu$ (OH)=3350 cm$^{-1}$. N.M.R. (CDCl$_3$): δ=1.7 (1H,s, exchangeable with D$_2$O); 2.6 (2H,t, J=6.75 Hz); 3.85 (2H,t, J=6.75 Hz); 4.45 (2H,s); 7.2 (4H,s).

c) 1-Bromomethyl-3-[2-(trimethylsilyloxy)ethyl]benzene

Obtained by operating as in example 26a, from 40 g (186 mmoles) of the compound prepared in example 93b, 30 g (186 mmoles) of 1,1,1,3,3,3-hexamethyldisilazane, 18.8 g (186 mmoles) of triethylamine and 20.2 g (186 mmoles) of trimethylsilyl chloride in 400 ml of dry tetrahydrofuran. After distillation, there is obtained 45.5 g (yield=85.2%) of a colorless liquid. b.p.$_8$=98°–104° C. N.M.R. (CDCl$_3$): δ=0.0 (9H,s); 2.75 (2H,t, J=6.75 Hz); 3.7 (2H,t, J=6.75 Hz); 4.4 (2H, s); 6.9–7.45 (4H,m).

d) 1-[[3-(2-Hydroxyethyl)phenyl]methyl]cyclopentanecarbonitrile

Obtained by operating as in example 87a, from 7.8g (77 mmoles) of diisopropylamine, 48.2 ml of a 1.6M solution of n-butyllithium in hexane, 6.7 g (70 mmoles) of commercial cyclopentanecarbonitrile, 18 ml of 1,3-dimethylimidazolidin-2-one and 20.5 g (71.4 mmoles) of the compound prepared in example 93c, in 110 ml of dry tetrahydrofuran. After distillation, there is obtained 9.6 g (yield=60.0%) of a viscous liquid. b.p.$_{0.4}$=160° C.

I.R. (film): $\nu$ (OH)=3420 cm$^{-1}$; (C≡N)=2215 cm$^{-1}$. N.M.R. (CDCl$_3$): δ=1.5–2.15 (8H,m); 2.4 (1H,s, exchangeable with D$_2$O); 2.85 (2H,s); 2.85 (2H,t, J=6.75 Hz); 3.8 (2H,t, J=6.75 Hz); 7.0–7.3 (4H,m).

e) 3-[[1-(Aminomethyl)cyclopentyl]methyl]benzeneethanol

Obtained by operating as in example 15a, from 1.9 g (50.4 mmoles) of LiAlH$_4$, 9.6 g (42 mmoles) of the compound prepared in example 93d in 55 ml of ether. There is obtained 5.0 g (yield=51.0%) of a colorless fluid paste, used without other purification.

I.R. (film): $\nu$ (NH$_2$)=3350 and 3300 cm$^{-1}$. N.M.R. (CDCl$_3$): δ=1.25–1.75 (8H,m); 1.85 (3H,s, exchangeable with D$_2$O) 2.45 (2H,s); 2.6 (2H,s); 3.1 (2H,t, J=6.75 Hz); 3.8 (2H,t, J=6.75 Hz); 6.8–7.4 (4H,m).

f) 4-Chloro-N-[[1-[[3-(2-hydroxyethyl)phenyl]methyl]cyclopentyl ]methyl ]benzenesulfonamide Obtained by operating as in example 32d, from 5 g (21.4 mmoles) of the compound prepared in example 93e, 2.7 g (26.7 mmoles) of triethylamine and 4.4 g (20,8 mmoles) of 4-chlorobenzenesulfonyl chloride in 110 ml of dry dichloromethane. After purification by chromatography on a column of silica in a dichloromethane-methanol (98:2) mixture, there is obtained 3.5 g (yield=42.5%) of a white pasty solid.

I.R. (film): $\nu$ (OH)=3450 cm$^{-1}$; (NH)=3290 cm$^{-1}$; (SO$_2$)=1320 cm$^{-1}$; (SO$_2$)=1150 cm$^{-1}$. N.M.R. (CDCl$_3$): $\delta$=1.1-1.9 (9H,m, 1H exchangeable with D$_2$O); 2.6 (2H,s); 2.5-3.0 (4H,m); 3.8 (2H,t, J=6.75 Hz); 5.1 (1H,t, J=6.75 Hz, exchangeable with D$_2$O); 6.75-7.2 (4H,m); 7.3-7.5 (2H,m); 7.6-7.9 (2H,m).

g) 3-[[1-[[[(4-Chlorophenyl)sulfonyl]amino]methyl]cyclopentyl]methyl]benzeneacetic acid Obtained by operating as in example 25g from 3.5 g (8.6 mmoles) of the compound prepared in example 93 f, 8.6 ml (17.2 mmoles) of Jones reagent in 110 ml acetone. After purification followed by recrystallizations in an isopropyl ether-ethanol mixture, there is obtained 1.4 g (yield=52.8%) of a white solid. M.P.=139.5°-40° C.

| Percentage analysis: C$_{21}$H$_{24}$ClNO$_4$S (MW = 421.939) | | | | | |
|---|---|---|---|---|---|
| | C % | H % | Cl % | N % | S % |
| Calculated | 59.78 | 3.73 | 8.40 | 3.32 | 7.60 |
| Found | 59.63 | 5.87 | 8.38 | 3.31 | 7.76 |

I.R. (KBr): $\nu$ (NH)=3270 cm$^{-1}$; (C=O)=1680 cm$^{-1}$; (SO$_2$)=1315 cm$^{-1}$; (SO$_2$)=1140 cm$^{-1}$. N.M.R. (CDCl$_3$)+DMSO d$_6$): $\delta$=1.1-1.7 (8H,m); 2.4-2.75 (4H,m); 3.5 (2H,s); 6.9-7.2 (4H,m); 7.2-7.6 (3H,m, 1H exchangeable with CF$_3$COOD); 7.7-8.0 (2H,m); 9.6 (1H,s wide, exchangeable with CF$_3$COOD).

EXAMPLES 94 to 102

The compound of examples 94 to 102:
4-[[1-[[[(4-Hexylphenyl)sulfonyl]amino]methyl]cyclopentyl]methyl]benzeneacetic acid
4-[[1-[[[(4-nitrophenyl)sulfonyl]amino]methyl]cyclopentyl]methyl]benzeneacetic acid
4-[[1-[[[(Naphthalen-1-yl)sulfonyl]amino]methyl]cyclopentyl]methyl]benzeneacetic acid
4-[[1-[[[(4-Hexyloxyphenyl)sulfonyl]amino]methyl]cyclopentyl]methyl]benzeneacetic acid
4-[[1-[[[(2-Fluorophenyl)sulfonyl]amino]methyl]cyclopentyl]methyl]benzeneacetic acid
4-[[1-[[[(4-Cyclohexylphenyl)sulfonyl]amino]methyl]cyclopentyl]methyl]benzeneacetic acid
4-[[1-[[[(Pentafluorophenyl)sulfonyl]amino]methyl]cyclopentyl]methyl]benzeneacetic acid
4-[[1-[[([1,1'-Biphenyl-4-yl]sulfonyl)amino]methyl]cyclopentyl]methyl]benzeneacetic acid
4-[[1-[[[(Naphthalen-2-yl)sulfonyl]amino]methyl]cyclopentyl]methyl]benzeneacetic acid have been prepared in 2 stages from 1-[[4-[2-[(3,4,5,6-tetrahydro-2H-pyran-2-yl)oxy]ethyl]phenyl]methyl]cyclopentanemethanamine prepared in example 85b:

a) Sulfonation by operating as in example 1c, by means of the corresponding sulfochloride;

b) Jones oxydation by operating as in example 25g.

The characteristics of the compounds obtained (A=COOH) and of their intermediates (A=CH$_2$O-THP)* are given in tables IIIa to IIIe:

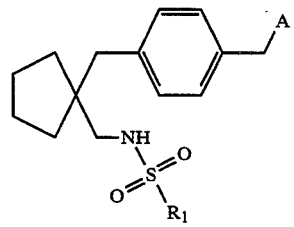

*THP=3,4,5,6-tetrahydro-2H-pyran-2yl

TABLE IIIa

| Ex. No. | R$_1$ | A | Empirical Formula[a] | M.P. (°C.) | NMR ($\delta$, CDCl$_3$) |
|---|---|---|---|---|---|
| 94a | ![structure: 4-hexylphenyl] | CH$_2$OTHP | | solid pasty | 0.65-2.0(25H, m); 2.6(2H, s); 2.7 (2H, d, J=6.75Hz, is converted into s with CF$_3$COOD); 2.85(4H, t, J=6.75 Hz); 3.25-4.2(4H, m); 4.35-4.7(2H, m, 1H exchangeable with CF$_3$COOD; 6.8-7.1(4H, m); 7.2-7.45(2H, m); 7.65-7.9(2H, m) |
| 94b | | COOH | C$_{27}$H$_{37}$NO$_4$S (471.656) | 135-137 (ethyl acetate hexane) | (DMSO d$_6$): 0.65-2.15(19H, m); 2.4-3.0(6H, m): 3.5(2H, s); 7.1(4H, s); 7.2-7.9(5H, m, 1H exchangeable with CF$_3$COOD); 12.25(1H, s wide, exchangeable with CF$_3$COOD) |
| 95a | ![structure: 4-nitrophenyl] | CH$_2$OTHP | C$_{26}$H$_{34}$N$_2$O$_6$S (502.626) | 108-111 (ethyl acetate hexane) | 1.25-2.0(14H, m); 2.6(2H, s); 2.7-3.0(4H, m); 3.35-4.1(4H, m); 4.6 (1H, m); 4.9(1H, t, J=6.75Hz, exchangeable with CF$_3$COOD); 6.75-7.25(4H, m); 7.85-8.1(2H, m); 8.2-8.45(2H, m) |
| 95b | NO$_2$ | COOH | C$_{21}$H$_{24}$N$_2$O$_6$S (432.491) | 131-134 (ethyl acetate hexane) | 1.3-1.75(8H, m); 2.55(2H, s); 2.7 (2H, d, J=6Hz, is converted into s with CF$_3$COOD); 3.6(2H, s); 5.0(1H, t, J=6.0Hz, exchangeable with CF$_3$COOD); 6.9-7.2(4H, m); 7.8-8.1 (2H, m); 8.15-8.4(2H, m); 8.9(1H, s wide, exchangeable with CF$_3$COOD) |

[a]PERCENTAGE ANALYSIS: C, H, N, S±0.19

TABLE IIIb

| Ex. No. | $R_1$ | A | Empirical Formula[a] | M.P. (°C.) | NMR (δ, CDCl₃) |
|---|---|---|---|---|---|
| 96a | naphthyl-methyl | CH₂OTHP | $C_{30}H_{37}NO_4S$ (507.689) | 104–106 (ethyl acetate hexane) | 1.25–1.75(14H, m); 2.45(2H, s); 2.6 (2H, d, J=6.75Hz, is converted into s with CF₃COOD); 2.75(2H, t, J=6.75 Hz); 3.3–4.2(4H, m); 4.45–4.9(2H, m, 1H exchangeable with CF₃COOD); 6.65–7.0(4H, m); 7.2–8.7(7H, m) |
| 96b | | COOH | $C_{25}H_{27}NO_4S$ (437.554) | 151–154 (ethyl acetate hexane) | 1.25–1.6(8H, m); 2.5(2H, s); 2.6 (2H, d, J=6.75Hz, is converted into s with CF₃COOD); 3.55(2H, s); 4.9– (1H, S wide t, J=6.75Hz, exchangeable with CF₃COOD); 6.7–7.1(4H, m); 7.3–8.8(7H, m); 9.3(1H, exchangeable with CF₃COOD) |
| 97a | 4-(hexyloxy)phenyl-methyl | CH₂OTHP | $C_{32}H_{47}NO_5S$ (557.79) | 83–85 (ethyl acetate hexane) | 0.75–21.(25H, m); 2.5–3.1(6H, m); 3.3–4.25(6H, m); 4.35–4.75(2H, m, 1H exchangeable with CF₃COOD); 6.8–7.3(6H, m); 7.65–7.9(2H, m) |
| 97b | | COOH | $C_{27}H_{37}NO_5S$ (487.655) | 137,5–138,5 (ethyl acetate hexane) | (acetone d₆): 0.75–1.9(19H, m); 2.65(2H, s); 2.7(2H, d, J=6.75Hz, is converted into s with CF₃COOD)3.6 (2H, s); 4.1(2H, t, J=6.75Hz); 6.1 (1H, t, J=6.75Hz, exchangeable with CF₃COOD); 6.9–7.2(2H, m); 7.15 (4H, s); 7.6–7.9(2H, m); 10.3(1H, s wide, exchangeable with CF₃COOD) |

[a]PERCENTAGE ANALYSIS: C, H, N, S±0.29

TABLE IIIc

| Ex. No. | $R_1$ | A | Empirical Formula[a] | M.P. (°C.) | NMR (δ, CDCl₃) |
|---|---|---|---|---|---|
| 98a | | CH₂OTHP | $C_{26}H_{34}FNO_4S$ (475.619) | 08–100 (ethyl acetate hexane) | 1.3–1.8(14H, m); 2.6(2Ha); 2.75 (2H, d, J=6.75Hz, is converted into s with CF₃COOD); 2.9(2H, t, J=6.75Hz), 3.35–4.2(m); 4.5–4.8 (2H, m, 1H exchangeable with CF₃COOD); 7.1(4H, s); 7.15=8.1 (4H, m) |
| 98b | | COOH | $C_{21}H_{24}FNO_4S$ (405.484) | 154–155 (ethyl acetate hexane) | (acetone d₆) 1.3–1.8(8H, m); 2.7 (2H, s); 2.8(2H, d, J=6.75Hz, is converted into s with CF₃COOD; 3.55(2H, s); 6.5(1H, t, J=6.75Hz, exchangeable with CF₃COOD; 7.2 (4H, s); 7.25–8.1(4H, m); 10.5 (1H, s wide, exchangeable with CF₃COOD) |
| 99a | | CH₂OTHP | $C_{32}H_{45}NO_4S$ (530.775) | 108–100 (ethyl acetate hexane) | (acetone d₆); 1.1–2.0(24H, m); 2.8 (2H, s); 2.6–2.9(5H, m); 3.15–4.0 (4H, m); 4.55(1H, m)6.15(1H, t, J= 6.75Hz, exchangeable with CF₃COOD); 7.0(4H, s); 7.25–7.5 (2H, m); 7.25–7.5(2H, m); 7.55–7.9(2H, m) |
| 99b | | COOH | $C_{27}H_{35}NO_4S$ (460.64) | 145–147 (ethyl acetate hexane) | (acetone d₆): 1.15–2.0(2H, s); (2H, s); 2.6–2.9(3H, m); 3.55(2Hs); 6.25(1H, t, J=6Hz, exchangeable with CF₃COOD); 7.15(4H, s); 7.3–7.55 (2H, m); 7.65–7.9(2H, m); 10.65(1H, s wide, exchangeable with CF₃COOD) |

[a]PERCENTAGE ANALYSIS: C, H.F.N.S.±except example 98 a, S=0.56

TABLE IIId

| Ex. No. | R₁ | A | Empirical Formula$^a$ | M.P. (°C.) | NMR (δ, CDCl₃) |
|---|---|---|---|---|---|
| 100a | 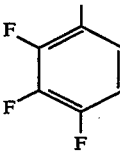 | CH₂OTHP | C₂₆H₃₀F₅NO₄S (547.579) | 95–96 (hexane) | 1.3–1.9(14H, m); 2.6(2H, s); 2.7–3.1(4H, m); 3.3–4.0(4H, m); 4.6(1H, m); 4.9(1H, t, J=6.75Hz, exchangeable with D₂O); 7.1(4H, s) |
|  |  | COOH | C₂₁H₂₀F₅NO₄S (477.444) | 129–130 (ethyl acetate hexane) | (acetone d₆): 1.4–1.8(8H, m); 2.75 (2H, s); 3.0(2H, d, J=6.75Hz, is converted into s with CF₃COCD); 3.6 (2H, s); 6.6(1H, t, J=6.75Hz, exchangeable with CF₃COOD); 7.2 (4H, s); 10.6(1H, s wide, exchangeable with CF₃COOD) |
| 101a | 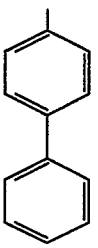 | CH₂OTHP | C₃₂H₃₉NO₄S (533.727) C₂₇H₂₉NO₄S –½H₂O (472.095) | 118–120 (ethyl acetate hexane) | 1.0–2.0(14H, m); 2.55(2H, s); 2.7 (2H, d, J=6.75Hz, is converted into s with CF₃COOD); 2.8(2H, t, J=6.75 Hz); 3.3–4.0(4H, m); 4.4–4.9(2H, m, 1H exchangeable with CF₃COOD); 6.75–7.2(4H, m); 7.25–8.0(9H, m) |
| 101b |  | COOH |  | 170–172 (ethyl acetate) | (CDCl₃+DMSO d₆): 1.15–1.7(8H, m); 2.45–2.75(4H, m); 3.45(2H, s); 6.75–7.1(5H, m, 1H exchangeable with CF₃COOD); 7.25–8.1(9H, m); 9.4(1H, s wide, exchangeable with CF₃COOD) |

$^a$PERCENTAGE ANALYSIS: C, H, F, N, S±0.30 except example 101b, S=−0.39

TABLE IIIe

| Ex. No. | R₁ | A | Empirical Formula$^a$ | M.P. (°C.) | NMR (δ, CDCl₃) |
|---|---|---|---|---|---|
| 102a |  | CH₂OTHP | C₃₀H₃₇NO₄S (507.689) | 132.5–133 (ethyl acetate) | 1.25–2.0(14H, m); 2.55(2H, s); 2.75 (2H, d, J=6.75Hz, is converted into s with CF₃COOD); 2,8(2H, t, J=6.75 Hz); 3.25–4.1(4H, m); 4.55(1H, m); 4.85(1H, t, J=6.75Hz, exchangeable with CF₃COOD); 6.9(4H, s); 7.4–8.1 (6H, m); 8.4(1H, m) |
| 102b |  | COOH | C₂₅H₂₇NO₄S (437.554) | 131.5–132.5 (ethyl acetate) | 1.2–1.8(8H, m); 2.6(2H, s); 2.7(2H, d, J=6.75Hz, is converted into s with CF₃COOD); 3.55(2H, s); 5.2(1H, t, J=6.75Hz, exchangeable with CF₃COOD); 7.0(4H, s); 7.5–8.1(6H, m); 8.35(1H, m); 10.0(1H, s wide, is exchangeable with CF₃COOD) |

$^a$PERCENTAGE ANALYSIS: C, H, N, S±0.29

EXAMPLE 103

4-[[1-[[[(4-methylthiophenyl]sulfonyl]amino]methyl]cyclopentyl]methyl]benzeneacetic acid a) N-[[1-(Phenylmethyl)cyclopentyl]methyl]-acetamide To a mixture of 22.7 g (120 mmoles) of the amine prepared in example 15a and 82 ml of pyridine, there is added dropwise, 9.85 g (126 mmoles) of acetyl chloride, while maintaining the temperature at 30° C. Then the mixture is refluxed ¾ h. After cooling, the mixture is poured over a mixture of ice and concentrated HCl, before extracting with dichloromethane. The organic phase washed with water, dried with Na₂SO₄ and concentrated, is purified by distillation, to give 23.8 g (yield=85.6%) of a thick yellow oil, which crystallizes. b.p.₁=200°-10° C. M.P.=70°-2° C. (ethyl acetatepentane).

I.R. (film): ν (NH)=3300 cm⁻¹; (C=O)=1630 cm⁻¹. N.M.R. (CDCl₃): δ=1.25–1.75 (8H,m); 1.8 (3H,s); 2.6 (2H,s); 3.1 (2H,d, J=6 Hz, is converted into singulet with CF₃COOD); 5.5 (1H,m, exchangeable with CF₃COOD); 7.15 (5H,s).

b) N-[[1-[(4-Acetylphenyl)methyl]cyclopentyl]methyl]acetamide

To a mixture under nitrogen and maintained at −10° C. of 183.2 g (0.792 mole) of the compound prepared in example 103a, 80.5 g (1.03 mole) of acetyl chloride and 3 l of dichloromethane, there is added by portions 316.8 g (2.376 moles) of aluminum chloride. The mixture is allowed to warm up to room temperature, and is stirred 20 h, before being poured over a ice-concentrated HCl mixture. Extraction is carried out with dichloromethane. The organic phase washed with a saturated solution of NaHCO₃, followed by water, dried over Na₂SO₄ and concentrated, is purified by recrystallization in ethyl acetate, to give 177.9 g (yield=82.2%) of a yellow solid. M.P.=136.7°−7−8.7° C.

I.R. (KBr): ν (NH)=3270 cm⁻¹; (C=O)=1655 cm⁻¹; (C=O)=1615 cm⁻¹. N.M.R. (CDCl₃): δ=1.25–1.75 (8H,m); 1.9 (3H,s); 2.5 (3H,s); 2.65 (2H,s); 3.1 (2H,d, J=6 Hz, is converted into singulet with CF₃COOD); 5.6 (1H,m, exchangeable with CF₃COOD); 7.1-7.35 (2H,m); 7.7–8.0 (2H,m).

c) Methyl 4-[[1-[(N-Acetylamino)methyl]cyclopentyl]methyl]benzeneacetate

Obtained by operating as in example 5e, from 177.9 g (0.651 mole) of the compound prepared in example 103b, 290 ml of methanol, 409 g (2.88 moles) of boron trifluoride etherate, 433 g (0.976 mole) of lead tetraacetate in 2.8 l of dichloromethane. There is obtained 195.6 g (yield=99.0%) of a beige solid, used without other purification. M.P.=99° C.

I.R. (KBr): $\nu$ (NH)=3280 cm$^{-1}$; (C=O)=1700 cm$^{-1}$; (C=O)=1610 cm$^{-1}$. N.M.R. ((CDCl$_3$): $\delta$=1.25–1.75 (8H,m); 1.9 (3H,s); 2.6 (2H,s); 3.1 (2H,d, J=6 Hz, is converted into singulet with CF$_3$COOD); 3.6 (2H,s); 3.7 (3H,s); 5.35 (1H,m, exchangeable with CF$_3$COOD); 7.15 (4H,s).

d) 4-[[1-(Aminomethyl)cyclopentyl]methyl]benzeneacetic acid

A mixture of 2.5 g (8.2 mmoles) of the compound prepared in example 103c and 60 ml (110 mmoles) of NaOH 1.83N, is refluxed 7 hours. After cooling, the reaction mixture is washed with ether, before being acidified at pH 6 with 10N HCl. The precipitate formed is filtrated and washed with cold water. The filtrate, concentrated up to a volume of 30 ml, is allowed to rest overnight at 4° C., to give a new precipitate which is filtered and washed with water. The combined precipitates are dried under vacuum at 110° C. and give 1.7 g (yield=85.0%) of a white powder which is used without other purification. M.P.=218° C. (dec.).

N.M.R. (CF$_3$COOD): $\delta$=1.25–2.1 (8H,m); 2.6 (2H,s); 3.2 (2H,m); 3.8 (2H,s); 7.25 (4H,s).

e) Methyl 4-[[1-(aminomethyl)cyclopentyl]methyl]benzeneacetate

Obtained by operating as in example 1a, from 9.9 g (46 mmoles) of the compound prepared in example 103d in 60 ml of methanol. There is obtained 8.7 g (yield=82.8%) of a brown thick liquid. b.p.$_{0.5}$=150°–200° C.

I.R. (film): $\nu$ (NH$_2$)=3375 cm$^{-1}$; (C=O)=1720 cm$^{-1}$. N.M.R. (CDCl$_3$): $\delta$=1.25 (2H,s, exchangeable with CF$_3$COOD); 1.25–1.75 (8H,m); 2.45 (2H,s); 2.6 (2H,s); 3.6 (2H,s); 3.65 (3H,s); 7.1 (4H,s).

f) Methyl 4-[[1-[[[(4-methylthiophenyl)sulfonyl]amino]methyl]cyclopentyl]methyl]benzeneacetate Obtained by operating as in example 32d, from 4 g (16 mmoles) of the compound prepared in example 103e, 1.9 g (18.8 mmoles) of triethylamine, 3.55 g (15.9 mmoles) of 4-(methylthio)benzenesulfonyl chloride (prepared according to Burton H. and Hu P. F., J. Chem. Soc. (1948), 604–5) in 70 ml of dry dichloromethane. After recrystallization in an ethyl acetate-hexane mixture, there is obtained 4.1 g (yield=56.9%) of a pale yellow solid. M.P.=109°–14° C.

I.R. (KBr): $\nu$ (NH)=3280 cm$^{-1}$; (C=O)=1705 cm$^{-1}$; (SO$_2$)=1320 cm$^{-1}$; (SO$_2$)=1155 cm$^{-1}$. N.M.R. (CDCl$_3$): $\delta$=1.25–1.75 (8H,m); 2.5 (3H,s); 2.6 (2H,s); 2.7 (2H,d, J=6.75 Hz, is converted into singulet with D$_2$O); 3.5 (2H,s); 3.7 (3H,s); 4.6 (1H,t, J=6.75 Hz, exchangeable with D$_2$O); 6.9–7.4 (6H,m); 7.55–7.8 (2H,m).

g) 4-[[1-[[[(4-Methylthiophenyl)sulfonyl]amino]methyl]cyclopentyl]methyl]benzeneacetic acid Obtained by operating as in example 1d, from 4.1 g (9.2 mmoles) of the compound prepared in example 103f, 0.8 g of KOH pellets, 60 ml ethanol and 60 ml water. After recrystallization in toluene and then in an ethyl acetate-hexane mixture, there is obtained 0.7g (yield=17.6%) of an off-white solid. M.P. 138°–9° C.

| Percentage analysis: C$_{22}$H$_{27}$NO$_4$S (MW = 433.59) | | | | |
|---|---|---|---|---|
| | C % | H % | N % | S % |
| Calculated | 60.94 | 6.28 | 3.23 | 14.79 |
| Found | 60.58 | 6.35 | 3.18 | 15.05 |

I.R. (KBr): $\nu$ (NH)=3270 cm$^{-1}$; (C=O)=1715 cm$^{-1}$; (SO$_2$)=1305 cm$^{-1}$; (SO$_2$)=1150 cm$^{-1}$. N.M.R. (CDCl$_3$): $\delta$=1.25–1.75 (8H,m); 2.5 (3H,s); 2.5–2.8 (4H,m); 3.6 (2H,s); 5.0 (1H,t, J=6.0 Hz, exchangeable with D$_2$O); 6.85–7.4 (6H,m); 7.6–7.9 (2H,m); 9.5 (1H,s wide, exchangeable with D$_2$O).

EXAMPLE 104

4-[[1-[[[5-(Dimethylamino)naphthalen-1-yl]sulfonyl]amino]methyl]cyclopentyl]methyl]benzeneacetic acid a) Methyl 4-[[1-[[[5-(dimethylamino)naphthalen-1-yl]sulfonyl]amino]methyl]cyclopentyl]methyl]benzeneacetate Obtained by operating as in example 32d, from 2.8 g (10.7 mmoles) of the compound prepared in example 103e, 1.3 g (12.8 mmoles) of triethylamine, 2.8 g (10.5 mmoles) of commercial 5-(dimethylamino)naphthalenesulfonyl chloride, in 56 ml dry dichloromethane. After purification by chromatography on a column of silica in a hexane-ethyl acetate (1:1) mixture, followed by recrystallization in a hexane-ethyl acetate mixture, there is obtained 0.9 g (yield=19.5%) of a yellow solid. M.P.=124°–6° C.

I.R. (KBr): $\nu$ (NH)=3300 cm$^{-1}$; (C=O)=1705 cm$^{-1}$; (SO$_2$)=1315 cm$^{-1}$; (SO$_2$)=1115 cm$^{-1}$. N.M.R. (CDCl$_3$): $\delta$=1.05–1.6 (8H,m); 2.5 (2H,s); 2.6 (2H,d, J=6.75 Hz, is converted into singulet with CF$_3$COOD) 2.9 (6H,s); 3.5 (2H,s); 3.7 (3H,s); 4.65 (1H,t, J=6.75 Hz, exchangeable with CF$_3$COOD); 6.75–7.75 (7H,m); 8.1–8.7 (3H,m).

b) 4-[[1-[[[5-(Dimethylamino)naphthalen-1-yl]sulfonyl]amino]methyl]cyclopentyl]methyl]benzeneacetic acid Obtained by operating as in example 1d, from 0.9 g (2.1 mmoles) of the compound prepared in example 104a, 0.18 g (3.1 mmoles) of KOH pellets, 90 ml water and 90 ml ethanol. After recrystallizations in acetone, there is obtained 0.2 g (yield=20.0%) of a yellow solid. M.P. 178°–81° C.

| Percentage analysis: C$_{27}$H$_{32}$N$_2$O$_4$S (MW = 480.621) | | | | |
|---|---|---|---|---|
| | C % | H % | N % | S % |
| Calculated | 67.47 | 6.71 | 5.83 | 6.67 |
| Found | 67.40 | 6.93 | 5.90 | 6.56 |

I.R. (KBr): $\nu$ (NH)=3300 cm$^{-1}$; (C=O)=1680cm$^{-1}$; (SO$_2$)=1310 cm$^{-1}$; (SO$_2$)=1150 cm$^{-1}$. N.M.R. (DMSO d$_6$): $\delta$=1.1–1.55 (8H,m); 2.3–2.7 (4H,m); 2.8 (6H,s); 3.4 (2H,s); 6.9 (4H,s); 7.15–8.6 (7H,m, 1H exchangeable with CF$_3$COOD); 12.1 (1H,s wide, exchangeable with CF$_3$COOD).

EXAMPLE 105

4-[[1-[[[(4-Chloro-2-fluorophenyl)sulfonyl]amino]methyl]cyclopentyl]methyl]benzeneacetic acid a) 4-Chloro-2-fluorobenzenesulfonyl chloride In a mixture, maintained at −10° C., of 75 ml HCl 10N and 22 ml acetic acid, 32.5 g (223 mmoles) of commercial 4-chloro-2-fluoroaniline, and 16.7 g (241 mmoles) of sodium nitrite in solution in 26 ml water are added. This reaction mixture is added by fractions to a solution maintained at 10° C. of 220 ml acetic acid saturated with SO₂ and containing 5.5 g (56.3 mmoles) of cuprous (I) chloride (I). Stirring is continued ½ hour at room temperature, before pouring over a ice-water mixture and extracting with ether. The organic phase is washed with a solution saturated with NaHCO₃, dried over Na₂SO₄ and concentrated. After distillation, there is obtained 44.5 g (yield=87.1%) of a pale yellow liquid which crystallizes. b.p.$_{0.1}$=81° C. M.P.=36°–8° C.

| Percentage analysis: $C_6H_3Cl_2FO_2S$ (MW = 229.052) | | | | | |
|---|---|---|---|---|---|
| | C % | H % | Cl % | F % | S % |
| Calculated | 31.46 | 1.32 | 30.96 | 8.29 | 14.00 |
| Found | 31.51 | 1.09 | 31.12 | 8.29 | 13.88 |

I.R. (film): $\nu$ (SO₂)=1375 cm⁻¹; (SO₂)=1175 cm⁻¹. N.M.R. (CDCl₃): δ=7.1–7.5 (2H,m); 7.7–8.1 (1H,m).

b) 4-[[1-[[[(4-Chloro-2-fluorophenyl)sulfonyl]amino]methyl]cyclopentyl]methyl]benzeneacetic acid A mixture of 3 g (10 mmoles) of the compound prepared in example 103c, 5.6 g (140 mmoles) of NaOH pellets and 72 ml of water, is refluxed during 4 hours. After cooling at 40° C., 2.3 g (10 mmoles) of the compound prepared in example 105a, is added, and stirring is continued 16 hours, at room temperature. 0.46 g (2 mmoles) of the compound prepared in example 105a is added again and stirring is continued 6 hours at room temperature. The reaction mixture is then washed with ether, and acidified with hydrochloric acid. The precipitate obtained is squeezed, washed with water and dried, before being purified by chromatography on a column of silica in ethyl acetate and by recrystallizations in an ethyl acetate-hexane mixture, to give 0.8 g (yield=18.2%) of a white solid. M.P.=151°–3° C.

| Percentage analysis: $C_{21}H_{23}ClFNO_4O$ (MW = 439.929) | | | | | | |
|---|---|---|---|---|---|---|
| | C % | H % | Cl % | F % | N % | S % |
| Calculated | 57.33 | 5.27 | 8.06 | 4.32 | 3.18 | 7.29 |
| Found | 57.50 | 5.16 | 8.13 | 4.40 | 3.21 | 7.26 |

I.R. (KBr): $\nu$ (NH)=3310 cm⁻¹; (C=O)=1690 cm⁻¹; (SO₂)=1335 cm⁻¹; (SO₂)=1155 cm⁻¹. N.M.R. (acetone d₆)=1.3–1.75 (8H,m); 2.7 (2H,s); 2.8 (2H,d, J=6 Hz, is converted into singulet with CF₃COOD); 3.6 (2H,s); 6.6 (1H,t, J=6 Hz, exchangeable with CF₃COOD); 7.2 (4H,s); 7.3–8.0 (3H,m); 10.5 1H,s wide, exchangeable with CF₃COOD).

EXAMPLE 106

4-[[1-[[[(Quinol-8-yl)sulfonyl]amino]methyl]cyclopentyl]methyl]benzeneacetic acid Obtained by operating as in example 105b, from 3.0 g (10 mmoles) of the compound prepared in example 103c, 4.8 g (120 mmoles) of NaOH, 2.3 g (10 mmoles) of (quinol-8-yl)sulfonyl chloride in 21 ml water. After 3 recrystallizations in an ethanol-water mixture, there is obtained 1.1 g (yield=25.0%) of fine off-white needles. M.P. 320° C.>(dec. from 200° C.).

| Percentage analysis: $C_{24}H_{26}N_2OP_4S$ (MW = 438.542) | | | | |
|---|---|---|---|---|
| | C % | H % | N % | S % |
| Calculated | 65.73 | 5.98 | 6.39 | 7.31 |
| Found | 65.77 | 6.02 | 6.23 | 7.39 |

I.R. (KBr): $\nu$ (NH)=3250 cm⁻¹; (C=O)=1705cm⁻¹; (SO₂)=1300 cm⁻¹; (SO₂)=1130 cm⁻¹. N.M.R. (DMSO d₆): δ=1.1–1.6 (8H,m); 2.4–2.7 (4H,m); 3.45 (2H,s); 7.0 (4H,s); 7.0 (1H,m, exchangeable with CF₃COOD); 7.5–7.9 (2H,m); 8.2–8.6 (3H,m); 9.05 (1H,m); 11.8 (1H,s wide, exchangeable with CF₃COOD).

EXAMPLE 107

4-[[1-[[[(4-Bromophenyl)sulfonyl]amino]methyl]cyclobutyl]methyl]benzeneacetic acid a) N-[[1-(Phenylmethyl)cyclobutyl]methyl-acetamide Obtained by operating as in example 103a, from 55.8 g (318 mmoles) of the amine prepared in example 27c, 26.2 g (333.8 mmoles) of acetyl chloride in 200 ml of pyridine. After grinding in hexane, there is obtained 59.4 g (yield=86.0%) of a creamy solid. M.P.=74°–6° C.

I.R. (KBr): $\nu$ (NH)=3310 cm⁻¹; (C=O)=1620 cm⁻¹. N.M.R. (CDCl₃): δ=1.5–2.0 (9H,m); 2.7 (2H,s); 3.25 (2H,d, J=6 Hz, is converted into singulet with CF₃COOD); 5.4 (1H,m, exchangeable with CF₃COOD); 7.2 (5H,s).

b) N-[[1-[(4-Acetylphenyl)methyl]cyclobutyl]methyl]acetamide

Obtained by operating as in example 103b, from 59 g (271 mmoles) of the compound prepared in example 107a, 27.5 g (350 mmoles) of acetyl chloride and 108 g (813 mmoles) of aluminum chloride in 1000 ml of dichloromethane. After recrystallization in toluene, there is obtained 55.6 g (yield=79.4%) of a yellow solid. M.P.=106°–110° C.

I.R. (KBr): $\nu$ (NH)=3310 cm⁻¹; (C=O)=1660 cm⁻¹; (C=O)=1625 cm⁻¹. N.M.R. (CDCl₃): $\nu$ =1.6–2.1 (6H,m); 1.95 (3H,s); 2.55 (3H,s); 2.75 (2H,s); 3.25 (2H,d, J=6 Hz, is converted into singulet with CF₃COOD); 5.7 (1H,m, exchangeable with CF₃COOD); 7.05-7.4 (2H,m); 7.7–8.0 (2H,m).

c) Methyl 4-[[1-[(N-acetyl-amino)methyl]cyclobutyl]methyl]benzeneacetate

Obtained by operating as in example 5e, from 55.6 g (214 mmoles) of the compound prepared in example 107b, 101 ml methanol, 91.1 g (643 mmoles) of boron trifluoride etherate and 113.8 g (257 mmoles) of lead tetraacetate in 1090 ml dichloromethane. After distillation, there is obtained 18.4 g (yield=29.7%) of a yellow thick liquid which crystallizes. b.p.$_{0.4}$=205° C. M.P.=62°–5° C.

I.R. (KBr): $\nu$ (NH)=3290 cm⁻¹; (C=O)=1720 cm⁻¹; (C=O)=1620 cm⁻¹. N.M.R. (CDCl₃) δ=1.6–2.1 (9H,m); 2.7 (2H,s); 3.25 (2H, d, J=6 Hz, is converted into singulet with CF₃COOD); 3.6 (2H,s); 3.7 (3H,s); 5.45 (1H,m, exchangeable with CF₃COOD); 7.1 (4H,s).

d) 4-[[1-(Aminomethyl)cyclobutyl]methyl]benzeneacetic acid

Obtained by operating as in example 103d, from 4.9 g (16.9 mmoles) of the compound prepared in example 107c and 4 g (100 mmoles) of NaOH in 35.5 ml water. There is obtained 3.3 g (yield=84.6%) of a white solid, used without other purification. M.P.>255° C.

N.M.R. (DMSO d₆+CF₃COOD): δ=1.7–2.1 (6H,m); 2.7–2.95 (4H,m); 3.5 (2H,s); 7.2 (4H,s).

e) 4-[[1-[[[(4-Bromophenyl)sulfonyl]amino]methyl]cyclobutyl]methyl]benzeneacetic acid To a mixture of 3.3 g (14 mmoles) of the compound prepared in example 107d, and 3.9 g (28 mmoles) of potassium carbonate in 400 ml water, 3.8 g (14.9 mmoles) of 4-bromobenzenesulfonyl chloride is added. The reaction mixture is thereafter refluxed 1 hour. After cooling, washing with ether, then acidification at pH 1 with diluted HCl, there is obtained a precipitate which is purified by recrystallization in ethyl acetate, to give 3.3 g (yield=52.4%) of a white solid. M.P.=180°-2° C.

| Percentage analysis: $C_{20}H_{22}BrNO_4S$ (MW = 452.363) | | | | | |
| --- | --- | --- | --- | --- | --- |
|  | C % | H % | Br % | N % | S % |
| Calculated | 53.10 | 4.90 | 17.66 | 3.10 | 7.09 |
| Found | 53.09 | 5.01 | 17.61 | 3.11 | 7.19 |

I.R. (KBr): $\nu$ (NH)=3240 cm$^{-1}$; (C=O)=1710 cm$^{-1}$; (SO$_2$)=1315 cm$^{-1}$; (SO$_2$)=1155 cm$^{-1}$. N.M.R. (acetone d$_6$): $\delta$=1.55–2.15 (6H,m); 2.8 (2H,s); 2.9 (2H,d, J=6 Hz, is converted into singulet with CF$_3$COOD); 3.6 (2H,s); 6.45 (1H,t, J=6 Hz, exchangeable with CF$_3$COOD); 7.2 (4H,s); 7.8 (4H,s); 10.9 (1H,s wide, exchangeable with CF$_3$COOD).

EXAMPLE 108

Biological activity

The products of examples 1 to 107 have been tested for platelet aggregation on guinea-pig and on the contraction of the aorta in rat as described previously. The results are given in tables IVa to IVc.

TABLE IV a

| EXAMPLE NO. | PLATELET AGGREGATION GUINEA-PIG IC 50 ($\mu$M) | VASOCONSTRICTION RAT AORTA IC 50 ($\mu$M) |
| --- | --- | --- |
| 1 | 0.69 | — |
| 2 | 0.72 | 0.07 |
| 3 | 0.60 | 0.06 |
| 4 | 23.0 | 0.20 |
| 6 | 6.3 | 0.56 |
| 7 | 3.3 | 0.30 |
| 9 | >20.0 | 1.0 |
| 10 | 1.3 | 5.0 |
| 11 | 0.39 | 0.05 |
| 12 | 1.8 | 0.07 |
| 13 | 0.68 | 0.06 |
| 14 | 5.5 | 0.07 |
| 15 | 1.1 | 0.30 |
| 16 | 2.4 | 0.20 |
| 17 | >20.0 | >1.0 |
| 18 | 0.66 | >1.0 |
| 19 | 0.26 | 0.10 |
| 20 | 0.28 | 0.07 |
| 22 | 0.71 | 0.15 |
| 23 | 0.48 | 0.04 |
| 24 | 0.57 | 0.30 |
| 25 | 1.5 | 0.06 |
| 26 | 3.1 | 0.46 |
| 27 | 0.29 | 0.02 |
| 28 | 2.6 | >1.0 |
| 29 | 5.3 | 1.0 |
| 30 | 0.92 | 1.0 |
| 31 | 2.5 | ≧1.0 |
| 32 | 1.8 | 0.40 |
| 33 | >5.0 | >1.0 |
| 43 | >5.0 | >1.0 |

TABLE IVb

| EXAMPLE NO. | PLATELET AGGREGATION GUINEA-PIG IC 50 ($\mu$M) | VASOCONSTRICTION RAT AORTA IC 50 ($\mu$M) |
| --- | --- | --- |
| 44 | >5.0 | — |
| 45 | >5.0 | — |
| 52 | >5.0 | >1.0 |
| 53 | 0.16 | 0.01 |
| 54 | 1.1 | 0.04 |
| 55 | 2.9 | 0.1 |
| 56 | 5.0 | 1.0 |
| 57 | 0.69 | 0.10 |
| 58 | 6.3 | 1.0 |
| 59 | 1.4 | 0.08 |
| 60 | >5.0 | >1.0 |
| 61 | >5.0 | >1.0 |
| 62 | 3.0 | 0.75 |
| 63 | >5.0 | >1.0 |
| 64 | 2.6 | 0.13 |
| 65 | 0.35 | 0.27 |
| 66 | >5.0 | >1.0 |
| 67 | 1.5 | 0.28 |
| 68 | 4.0 | 0.40 |
| 69 | >5.0 | >1.0 |
| 70 | >5.0 | 1.0 |
| 71 | 3.0 | 0.04 |
| 72 | 0.64 | 0.04 |
| 73 | 0.70 | 0.20 |
| 74 | >5.0 | >1.0 |
| 75 | >5.0 | >1.0 |
| 76 | 2.9 | >1.0 |
| 77 | 2.4 | >1.0 |
| 79 | 0.10 | 0.17 |

TABLE IV c

| EXAMPLE NO. | PLATELET AGGREGATION GUINEA-PIG IC 50 ($\mu$M) | VASOCONSTRICTION RAT AORTA IC 50 ($\mu$M) |
| --- | --- | --- |
| 80 | 2.9 | 0.19 |
| 81 | 1.6 | 0.06 |
| 82 | 2.0 | 1.0 |
| 83 | 0.94 | 1.0 |
| 84 | >5.0 | 1.0 |
| 85 | 1.3 | >1.0 |
| 86 | 0.51 | 1.0 |
| 87 | 4.0 | 0.60 |
| 88 | 0.31 | 1.0 |
| 89 | 0.26 | 0.03 |
| 90 | >5.0 | >1.0 |
| 91 | 3.1 | 1.0 |
| 92 | 0.37 | 1.0 |
| 93 | 1.6 | 0.05 |
| 94 | 1.8 | >1.0 |
| 95 | 0.57 | 0.28 |
| 96 | 0.75 | >1.0 |
| 97 | 5.9 | >1.0 |
| 98 | 0.25 | 0.32 |
| 99 | >5.0 | >1.0 |
| 100 | >5.0 | >1.0 |
| 101 | >5.0 | >1.0 |
| 102 | 1.0 | — |
| 103 | 1.0 | 0.18 |
| 104 | >5.0 | >1.0 |
| 105 | 0.57 | 0.11 |
| 106 | >5.0 | — |

We claim:

1. A compound of formula (1):

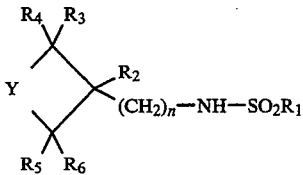

wherein
- R₁ is selected from (i) phenyl, phenyl substituted by one or more radical (s) selected from the group consisting of halogen, branched or linear (C₁-C₇)alkyl, (C₁-C₇)acyl, trifluoromethyl, (C₁-C₇)alkoxy, (C₁-C₇)alkylsulfonyl, trifluoromethoxy, nitro, cyano, (C₁-C₇)cycloalkyl, phenyl, (C₁-C₇)alkylthio, amino, (C₁-C₇)alkylsulfinyl, hydroxy and acetamido, (iii) naphtyl, (iv) dimethylaminonaphtyl, (v) thienyl, (vi) chlorothienyl, (vii) furyl, (viii) imidazolyl, (ix) quinolyl and (x) methylquinolyl;
- R₂ and R₃ are different; one of the two represents W, the other is selected from the group consisting of hydrogen, halogen, trifluoromethyl, (C₁-C₇)alkyl, (C₃-C₁₂)cycloalkyl, (C₁-C₇)alkoxy, (C₁-C₇)alkylthio, (C₁-C₇)alkylsulfinyl, (C₁-C₇)alkylsulfonyl, (C₁-C₇)acyl, (C₁-C₇)thioacyl, hydroxy, amino (C₁-C₇)alkyl substituted amino, di-(C₁-C₇)alkyl substituted amino, nitro, nitrile, and azide;
- W is a group —Z—Ar—(CH₂)_q—A in which A is selected from —CO₂H, —SO₃H, —PO₃H, —CO₂Et, —CO₃Me, hydroxyl, carboxyethylaminocarbonyl, carboxyethylcarbonyl, —CONH₂, diethylaminoethylcarbonyl, carboxyethylcarbonyl, morpholinocarbonyl, tetrazolyl, 4,5-dihydro-3-oxo[2H]pyridazinyl and COCH₃;
- q is selected from 0, 1, 2, 3 and 4; Ar represents phenyl; Z is selected from oxygen, methylene and a bond;
- R₄, R₅ and R₆ independently have the meaning of R₂ or R₃, except W;
- Y is a group —(CH₂)_s—B—(CH₂)_t; s and t are each independently selected from 0, 1 and 2; B is selected from oxygen, carbonyl, —C(Me)₂ and a bond; n is selected from 0 and 1;
- a physiologically acceptable salt thereof, a physiologically acceptable salt in the form of a complex thereof, a physiologically acceptable complex thereof, a physiologically acceptable ester thereof or a physiologically acceptable amide thereof.

2. The compound of claim 1, wherein R₃ is a group W and R is different from W.

3. The compound of claim 1, wherein R₂ is W, and R₃ is different from W.

4. The compound of claim 1, wherein R₃ is a group W, and Z contained in W is an atom of oxygen.

5. The compound of claim 1, wherein R₂ is W, and Z contained in W is a bond.

6. The compound of claim 1, selected from the group consisting of trans-4-[[2-[[(4-chlorophenyl)sulfonyl]amino]cyclopentyl]methyl]-benzeneacetic acid, trans-4-[[2-[[(4-chlorophenyl)sulfonyl]amino]cyclohexyl]methyl]benzeneacetic acid, cis-4-[[2-[[(4-chlorophenyl)sulfonyl]amino]cyclopentyl]methyl]benzeneacetic acid.

7. The compound of claim 1, consisting of 4-[2-[[(4-chlorophenyl)sulfonyl]amino]cyclopentyloxy]benzeneacetic acid.

8. The compound of claim 1, selected from the group consisting of 4-[[1-[[[(4-chlorophenyl)sulfonyl]amino]methyl]cyclopentyl]methyl]benzeneacetic acid, 4-[[1-[[[(4-methylphenyl)sulfonyl]amino]methyl]cyclopentyl]methyl]benzeneacetic acid, 4-[[1-[[[(4-bromophenyl)sulfonyl]amino]methyl]cyclopentyl]methyl]benzeneacetic acid, 4-[[1-[[[(4-chloro-2-fluorophenyl)sulfonyl]amino]methyl]cyclopentyl]methyl]benzeneacetic acid, 4-[[1-[[[(4-chlorophenyl)sulfonyl]amino]methyl]cyclopropyl]methyl]benzeneacetic acid, 4-[[1-[[[(4-chlorophenyl)sulfonyl]amino]methyl]cyclobutyl]methyl]benzeneacetic acid, 4-[[1-[[[(4-bromophenyl)sulfonyl]amino]methyl]cyclobutyl]methyl]benzeneacetic acid, 4-[[1-[[[(4-chlorophenyl]sulfonyl]amino]methyl]-3,3-dimethylcyclobutyl]methyl]benzeneacetic acid.

9. The compound of claim 1, selected from the group consisting of 4-[1-[[[(4-chlorophenyl)sulfonyl]amino]methyl]cyclopentyl]benzeneacetic acid, 4-[1-[[[(4-chlorophenyl)sulfonyl]amino]methyl]cyclobutyl]benzeneacetic acid, 4-[1-[[[(4-chlorophenyl)sulfonyl]amino]methyl]cyclopropyl]benzeneacetic acid.

10. Medicine containing as active ingredient an efficient quantity of at least one compound described in claim 1, in association with a pharmaceutically acceptable carrier.

11. A compound according to claim 1, in which R₂ and R₃ are different, one of the two representing W, the other being selected from the group consisting of hydrogen and (C₁-C₇)alkyl.

12. A compound of formula (1):

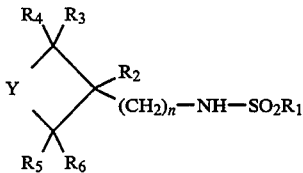

wherein
- R₁ is selected from (i) phenyl, (ii) phenyl substituted by one or more radical (s) selected from the group consisting of halogen, branched or linear (C₁-C₇)alkyl, (C₁-₇)acyl, trifluoromethyl, (C₁-C₇)alkoxy, methylsulfonyl, trifluoromethoxy, nitro, cyano, cyclohexyl, phenyl, methylthio, amino, methylsulfinyl, hydroxy and acetamido, (iii) naphtyl, (iv) dimethylaminoaphtyl, (v) thienyl, (vi) chlorothienyl, (vii) furyl, (viii) imidazolyl, (ix) quinolyl and (x) methylquinolyl;
- R₂ and R₃ are different; one of the two represents W, the other is selected from the group consisting of hydrogen, halogen, trifluoromethyl, (C₁-C₇)alkyl, (C₃-C₁₂)cycloalkyl, (C₁-C₇)alkoxy, (C₁-C₇)alkylthio, (C₁-C₇)alkylsulfinyl, (C₁-C₇)alkylsulfonyl, (C₁-C₇)acyl, (C₁-C₇)thioacyl, hydroxy, amino, (C₁-C₇)alkyl substituted amino, di- (C₁-C₇)alkyl substituted amino, nitro, nitrile and azide;
- W is a group —Z—Ar—(CH₂)_q—A in which A is selected from —CO₂H, —SO₃H, —PO₃H₂, —CO₂Et, —CO₂Me, hydroxyl, carboxyethylaminocarbonyl, carboxyethylcarbonyl, —CONH₂, diethylaminoethylcarbonyl, carboxyethylcarbonyl, morpholinocarbonyl, tetrazolyl, 4,5-dihydro-3-oxo[2H]pyridazinyl and COCH₃;
- q is selected from 0, 1, 2; Ar represents phenyl; Z is selected from oxygen, methylene and a bond;
- R₄, R₅ and R₆ independently have the meaning of R₂ or R₃, except W;

Y is a group $-(CH_2)_s-B-(CH_2)_t$; s and t are each independently selected from 0, 1 and 2; B is selected from oxygen, carbonyl, $-C(Me)_2$ and a bond; n is selected from 0 and 1; a physiologically acceptable salt thereof, a physiologically acceptable salt in the form of a complex thereof, a physiologically acceptable complex thereof, a physiologically acceptable ester thereof, or a physiologically acceptable amide thereof.

* * * * *

UNITED STATES PATENT AND TRADEMARK OFFICE
CERTIFICATE OF CORRECTION

PATENT NO. : 5,387,709
DATED : February 7, 1995
INVENTOR(S) : Claude LARDY, et al.

It is certified that error appears in the above-indentified patent and that said Letters Patent is hereby corrected as shown below:

On the title page, Item [75], the inventorship should read:

--Claude Lardy, Lyon; Daniel Guerrier, Saint Genis Laval; Gilles Chavernac, La Mulatiere; François Collonges, Beynost Miribel, all of France--

Signed and Sealed this

Second Day of May, 1995

BRUCE LEHMAN

*Attest:*

*Attesting Officer*          *Commissioner of Patents and Trademarks*